(12) United States Patent
Philippe et al.

(10) Patent No.: US 11,618,908 B2
(45) Date of Patent: Apr. 4, 2023

(54) MICROBIAL PRODUCTION OF ROTUNDONE

(71) Applicant: MANUS BIO INC., Cambridge, MA (US)

(72) Inventors: Ryan N. Philippe, Cambridge, MA (US); Ajikumar Parayil Kumaran, Cambridge, MA (US); Christine Nicole S. Santos, Cambridge, MA (US); Jason Donald, Cambridge, MA (US); Stephen Sarria, Cambridge, MA (US)

(73) Assignee: MANUS BIO INC., Cambridge, MA (US)

( * ) Notice: Subject to any disclaimer, the term of this patent is extended or adjusted under 35 U.S.C. 154(b) by 0 days.

(21) Appl. No.: 17/273,567

(22) PCT Filed: Sep. 6, 2019

(86) PCT No.: PCT/US2019/050004
§ 371 (c)(1),
(2) Date: Mar. 4, 2021

(87) PCT Pub. No.: WO2020/051488
PCT Pub. Date: Mar. 12, 2020

(65) Prior Publication Data
US 2021/0254107 A1 Aug. 19, 2021

Related U.S. Application Data

(60) Provisional application No. 62/727,815, filed on Sep. 6, 2018.

(51) Int. Cl.
| C12P 7/26 | (2006.01) |
| C12N 9/04 | (2006.01) |
| C12N 9/02 | (2006.01) |
| C12N 9/10 | (2006.01) |
| C12N 9/88 | (2006.01) |
| C12N 15/52 | (2006.01) |

(52) U.S. Cl.
CPC ............. *C12P 7/26* (2013.01); *C12N 9/0006* (2013.01); *C12N 9/0071* (2013.01); *C12N 9/1085* (2013.01); *C12N 9/88* (2013.01); *C12N 15/52* (2013.01); *C12Y 205/0101* (2013.01); *C12Y 402/03087* (2013.01)

(58) Field of Classification Search
None
See application file for complete search history.

(56) References Cited

U.S. PATENT DOCUMENTS

| 9,404,130 | B2 | 8/2016 | Ajikumar et al. |
| 9,796,980 | B2 | 10/2017 | Ajikumar et al. |
| 9,957,527 | B2 | 5/2018 | Ajikumar et al. |
| 10,463,062 | B2 | 11/2019 | Philippe et al. |
| 10,480,015 | B2 | 11/2019 | Kumaran et al. |
| 10,501,760 | B2 | 12/2019 | Kumaran et al. |
| 10,662,442 | B2 | 5/2020 | Kumaran et al. |
| 10,774,314 | B2 | 9/2020 | Donald et al. |
| 10,934,564 | B2 | 3/2021 | Kumaran et al. |
| 2015/0007368 | A1 | 1/2015 | Saran et al. |
| 2015/0218588 | A1* | 8/2015 | Schalk ................. C12N 9/0071 435/189 |
| 2017/0356059 | A1* | 12/2017 | Kino ..................... C12N 15/66 |
| 2018/0135081 | A1 | 5/2018 | Kumaran et al. |
| 2020/0299737 | A1* | 9/2020 | Goeke ..................... C12P 5/002 |
| 2021/0161092 | A1 | 6/2021 | Kumaran et al. |

FOREIGN PATENT DOCUMENTS

| JP | 2017216974 A | 12/2017 | |
| WO | WO-2016029153 A1 * | 2/2016 | ............. A01N 27/00 |

OTHER PUBLICATIONS

European patent application EP 17205361.3 filed Dec. 5, 2017. (Year: 2017).*
GenBank, Accession No. AMQ67166, 2016, www.ncbi.nlm.gov. (Year: 2016).*
Takase et al., Cytochrome P450 CYP71BE5 in grapevine (*Vitis vinifera*) catalyzes the formation of the spicy aroma compound (−)-rotundone, J. Exp. Botany 67, 2016, 787-98. (Year: 2016).*
GenBank, Accession No. XM_002282452, 2016, www.ncbi.nlm.nih.gov. (Year: 2016).*
Uniprot, Accession No. Q46856, 2017, www.uniprot.org. (Year: 2017).*
Kumeta et al., Genomic organization of d-guaiene synthase genes in *Aquilaria crassna* and its possible use for the identification of *Aquilaria* species, J. Nat. Med. 65, 2011, 508-12. (Year: 2011).*
GenBank, Accession No. A0A076U535, 2018, www.ncbi.nlm.nih.gov. (Year: 2018).*
GenBank, Accession No. JF289265, 2011, www.ncbi.nlm.nih.gov. (Year: 2011).*
Degenhardt et al., Monoterpene and sesquiterpene synthases and the origin of terpene skeletal diversity in plants, Phytochemistry 70, 2009. 1621-37. (Year: 2009).*
Drew, et al. 'Two Key Polymorphisms in a Newly Discovered Allele of the Vitis vinifera TPS24 Gene are Responsible for the Production of the Rotundone Precursor alpha-guaiene', Journal of Experimental Botany, 2016, vol. 67, No. 3 pp. 799-808.

* cited by examiner

*Primary Examiner* — Robert B Mondesi
*Assistant Examiner* — Todd M Epstein
(74) *Attorney, Agent, or Firm* — Morgan, Lewis & Bockius LLP

(57) ABSTRACT

The present disclosure provides methods and compositions for producing rotundone. In various aspects, the present disclosure provides enzymes, polynucleotides encoding said enzymes, and recombinant microbial host cells (or microbial host strains) for the production of rotundone. In some embodiments, the present disclosure provides microbial host cells for producing rotundone at high purity and/or yield, from either enzymatic transformation of α-guaiene, or from sugar or other carbon source. The present disclosure further provides methods of making products containing rotundone, including flavor or fragrance products, among others.

25 Claims, 13 Drawing Sheets
Specification includes a Sequence Listing.

FIG. 4

| Mutant | Fold improvement in α-guaiene |
|---|---|
| F406L | 1.71 |
| Y442L | 1.16 |
| I371L | 1.15 |
| M273L | 1.15 |
| S374A | 1.13 |
| I399V | 1.12 |
| R377V | 1.08 |
| L419T | 1.08 |
| F382L | 1.07 |
| R290K | 1.07 |
| F512L | 1.07 |
| K522D | 1.07 |
| F368M | 1.07 |
| T72I | 1.06 |
| E454K | 1.06 |
| V433I | 1.05 |
| Y381W | 1.05 |
| I298V | 1.04 |
| L297I | 1.03 |
| G268C | 1.02 |
| I343V | 1.02 |
| V311L | 1.02 |
| L446I | 1.01 |
| Q447V | 1.01 |
| E457H | 1.00 |
| I291V | 0.98 |
| P508R | 0.98 |
| I265V | 0.98 |
| I229L | 0.98 |
| S503M | 0.97 |
| Q530G | 0.97 |
| A544P | 0.95 |
| I443M | 0.94 |

| Mutant | Fold improvement in α-guaiene |
|---|---|
| V505L | 0.94 |
| W147L | 0.94 |
| V24I | 0.94 |
| A451F | 0.91 |
| Q447K | 0.89 |
| V111L | 0.89 |
| V506L | 0.88 |
| V459A | 0.88 |
| A266V | 0.87 |
| V532K | 0.87 |
| T145G | 0.86 |
| S504P | 0.86 |
| D528H | 0.86 |
| Y270F | 0.85 |
| E517D | 0.82 |
| T448S | 0.81 |
| R414M | 0.81 |
| E453Q | 0.81 |
| S224L | 0.77 |
| S527T | 0.76 |
| G339T | 0.73 |
| T23S | 0.72 |
| E431K | 0.71 |
| del_A354 | 0.67 |
| L423F | 0.67 |
| M519L | 0.64 |
| S400T | 0.58 |
| R490D | 0.49 |
| S397A | 0.40 |
| T295A | 0.39 |
| Y449H | 0.35 |
| M432I | 0.31 |

| Mutant | Fold improvement in α-guaiene |
|---|---|
| G531K | 0.27 |
| G401S | 0.25 |
| Q376F | 0.21 |
| I329L | 0.17 |
| M273H | 0.16 |
| I407A | 0.15 |
| S509I | 0.15 |
| A440C | 0.13 |
| V304A | 0.12 |
| G401C | 0.11 |
| K522D | 0.08 |
| S502P | 0.07 |
| R536F | 0.05 |
| A275V | 0.05 |
| L288F | 0.03 |
| L516I | 0.03 |
| G523E | 0.02 |
| I398L | 0.02 |
| D521K | 0.02 |
| T301I | 0.02 |
| S529V | 0.01 |
| H276Y | 0.01 |
| L297V | 0.01 |
| Y375F | 0.01 |
| ins523_524_N | 0.01 |
| T533A | 0.00 |
| T533L | 0.00 |
| R463E | 0.00 |
| G339A | 0.00 |
| ins526_527_G | 0.00 |
| del_G531 | 0.00 |

FIG. 5

| Mutant | Fold improvement in % α-guaiene |
|---|---|
| I443M | 2.40 |
| F406L | 2.12 |
| F512L | 1.23 |

FIG. 10

```
NtKO     MDAILNLQTVPLGTALTIGGPAVALG-GISLWFLKEYVNDQKRKSSNFLPPLPEVPGLPV
LsKO     MDGVIDMQTIPLRTAIAIGGTAVALVVALYFWFLRSYASP-SHH-SNHLPPVPEVPGVPV
CcKO     ----MDMQSIP---AIAIGSTAVAIALGLFFWFFRRHVPDHIDH-PNHLPSVPEVPGIPV
AaKO     MDALTDMLQIPPATPITVAITTVTIAVAI-FLYIKSHASNHSRR-STHLPPVPEVPGVPV
KOeng    --MAWEYALIGLVVGIIIGAVAMR-------WYLKSYTSARRSQ-SNHLPRVPEVPGVPL
HaKO     MDALTGMLPIPPATALAIGGTAIALAVAISFWFLRSYTSG---E-SNRLPRVPEVPGVPV
                  :   : :.  ::        ::. :.    .. **  :*****:*:

NtKO     IGNLLQLTEKKPHKTFTNWAETYGPIYSIKTGANTIVVLNTNELAKEAMVTRYSAISTRK
LsKO     LGNLLQLKEKKPYMTFTKWAEMYGPIYSIRTGATSMVVVSSNEIAKEVVVTRFPSISTRK
CcKO     LGNLLQLKEKKPYMTFTKWAETYGPIYSIRTGAISMVVVSSNAIAKEALVTRFPSISTRK
AaKO     LGNLLQLKEKKPYLTFTRWAQTYGAIYSIRTGATSMVVVSSSEIAKEAMVTRFSSISTRN
KOeng    LGNLLQLKEKKPYMTFTKWAATYGPIYSIKTGATSVVVVSSNEIAKEALVTRFQSISTRN
HaKO     LGNLLQLKEKKPYMTFTRWAETYGPIYSIRTGATSMVVVSSNEIAKEAFVTRFESISTRN
         :******.****: ***.**  **.****.***  ::**:.:. :***..***.:****:

NtKO     LTNALKILTCDKSIVAISDYDEFHKTVKRHVLTSVLGPNAQKRHRIHRDTLIENVSKQLH
LsKO     LSYAKVLTEDKSMVAMSDYHDYHKTVKRHILTAVLGPNAQKKFRAHRDTMMENVSNELH
CcKO     LSKALEVLTADKTMVAMSDYNDYHKTVKRHILTAVLGPNAQKKHRVHRDIMMQNLSNQLH
AaKO     LSKALTILTADKTMVAMSDYNDYHRTVKRHILTAMLGPNAQRKQRVHRDFMIENISKQLH
KOeng    LSKALKVLTADKQMVAMSDYDDYHKTVKRHILTAVLGPNAQKKHRIHRDIMMDNISTQLH
HaKO     LSKALKILTDDKTMVAMSDYNDYHKTVKRHILTAMLGPNAQKKHRIQRDIMMENLSNRLH
         *:. **  :** ** :**:***  :*.*****:**::******..  * :** :::*:*. **

NtKO     DLVRKYP-NEAVNLRKIFQSELFGLALKQALGKDIESIYVEGLDATLPREDVLKTLVLDI
LsKO     AFFEKNP-NQEVNLRKIFQSQLFGLAMKQALGKDVESIYVEDLETTMKREEIFEVLVVDP
CcKO     TFVQNSP-QEEVNLRKVFQSELFGLAMRQTMGKDVESIYVEDLGTTMNRDEIFQVLVVDP
AaKO     AFVENSP-KEEVDLRKIFQSELFGLAMKQAVGKDVESLNVEDLGVTMKRDEIFQVLVVDP
KOeng    EFVKNNPEQEEVDLRKIFQSELFGLAMRQALGKDVESLYVEDLKITMNRDEILQVLVVDP
HaKO     AFVKTSTEQEEVDLREIFQSELFGLAMRQTMGKDVESIYVEDLKITMKRDEIFQVLVVDP
          :.  .  ::  *:**::***:*****:.*::****:*: *:.*  *:  *:::::..**:*

NtKO     MEGAIDVDWRDFFPYLKWVPNKSFENRIQRKHLRREAVMKALIMEQRKRINSGEKLNSYI
LsKO     MMGAIEVDWRDFFPYLKWVPNKSFENIIHRMYTRREAVMKALIQEHKKRIASGENLNSYI
CcKO     LMGAIEVDWRDFFPYLKWIPNRNFENTIQQMYIRREAVMKALIQEHRKRIASGENLNSYI
AaKO     MMGAIEVDWRDFFPYLKWVPNKKFENTIQQMYIRRKAVMKALIKEHKKRIASGENLNSYI
KOeng    MMGAIDVDWRDFFPYLKWVPNKKFENTIQQMYIRREAVMKSLIKEQKKRIASGEKLNSYI
HaKO     MMGAIDVDWRDFFPYLKWVPNKKFENTIQQMYIRREAVMKALIKQHKERIASGEKLNSYI
         : ***:************:**..*** *:.  : **:****:**  :::.** ***:*****
```

NtKO (SEQ ID NO: 45)
LsKO (SEQ ID NO: 46)
CcKO (SEQ ID NO: 47)
KOeng (SEQ ID NO: 51)
AaKO (SEQ ID NO: 49)
HaKO (SEQ ID NO: 50)

FIG. 10 (contd.)

```
NtKO     MDAILNLQTVPLGTALTIGGPAVALG-GISLWFLKEYVNDQKRKSSNFLPPLPEVPGLPV
LsKO     MDGVIDMQTIPLRTAIAIGGTAVALVVALYFWFLRSYASP-SHH-SNHLPPVPEVPGVPV
CcKO     ----MDMQSIP---AIAIGSTAVAIALGLFFWFFRRHVPDHIDH-PNHLPSVPEVPGIPV
AaKO     MDALTDMLQIPPATPITVAITTVTIAVAI-FLYIKSHASNHSRR-STHLPPVPEVPGVPV
KOeng    --MAWEYALIGLVVGIIIGAVAMR-------WYLKSYTSARRSQ-SNHLPRVPEVPGVPL
HaKO     MDALTGMLPIPPATALAIGGTAIALAVAISFWFLRSYTSG---E-SNRLPRVPEVPGVPV
           :    : :..  ::           ..  ** :*****:*:

NtKO     IGNLLQLTEKKPHKTFTNWAETYGPIYSIKTGANTIVVLNTNELAKEAMVTRYSAISTRK
LsKO     LGNLLQLKEKKPYMTFTKWAEMYGPIYSIRTGATSMVVVSSNEIAKEVVVTRFPSISTRK
CcKO     LGNLLQLKEKKPYMTFTKWAETYGPIYSIRTGAISMVVVSSNAIAKEALVTRFPSISTRK
AaKO     LGNLLQLKEKKPYLTFTRWAQTYGAIYSIRTGATSMVVVSSSEIAKEAMVTRFSSISTRN
KOeng    LGNLLQLKEKKPYMTFTKWAATYGPIYSIKTGATSVVVVSSNEIAKEALVTRFQSISTRN
HaKO     LGNLLQLKEKKPYMTFTRWAETYGPIYSIRTGATSMVVVSSNEIAKEAFVTRFESISTRN
         :******.****:.*** .**  ** ****.*** ::**:.:.  :***..***:  :****:

NtKO     LTNALKILTCDKSIVAISDYDEFHKTVKRHVLTSVLGPNAQKRHRIHRDTLIENVSKQLH
LsKO     LSYALKVLTEDKSMVAMSDYHDYHKTVKRHILTAVLGPNAQKKFRAHRDTMMENVSNELH
CcKO     LSKALEVLTADKTMVAMSDYNDYHKTVKRHILTAVLGPNAQKKHRVHRDIMMQNLSNQLH
AaKO     LSKALTILTADKTMVAMSDYNDYHRTVKRHILTAMLGPNAQRKQRVHRDFMIENISKQLH
KOeng    LSKALKVLTADKQMVAMSDYDDYHKTVKRHILTAVLGPNAQKKHRIHRDIMMDNISTQLH
HaKO     LSKALKILTDDKTMVAMSDYNDYHKTVKRHILTAMLGPNAQKKHRIQRDIMMENLSNRLH
         *:.**  ** **.:*:***  ::*.*****:**:*:**:******  : :** :::**:. **

NtKO     DLVRKYP-NEAVNLRKIFQSELFGLALKQALGKDIESIYVEGLDATLPREDVLKTLVLDI
LsKO     AFFEKNP-NQEVNLRKIFQSQLFGLAMKQALGKDVESIYVKDLETTMKREEIFEVLVVDP
CcKO     TFVQNSP-QEEVNLRKVFQSELFGLAMRQTMGKDVESIYVEDLGTTMNRDEIFQVLVVDP
AaKO     AFVENSP-KEEVDLRKIFQSELFGLAMKQAVGKDVESLNVEDLGVTMKRDEIFQVLVVDP
KOeng    EFVKNNPEQEEVDLRKIFQSELFGLAMRQALGKDVESLYVEDLKITMNRDEILQVLVVDP
HaKO     AFVKTSTEQEEVDLREIFQSELFGLAMRQTMGKDVESIYVEDLKITMKRDEIFQVLVVDP
         :. .  ::  *:**:***:*****. *:;***;**: *:.*  *: :::::.**:*

NtKO     MEGAIDVDWRDFFPYLKWVPNKSFENRIQRKHLRREAVMKALIMEQRKRINSGEKLNSYI
LsKO     MMGAIEVDWRDFFPYLKWVPNKSFENIIHRMYTRREAVMKALIQEHKKRIASGENLNSYI
CcKO     LMGAIEVDWRDFFPYLKWIPNRNFENTIQQMYIRREAVMKALIQEHRKRIASGENLNSYI
AaKO     MMGAIEVDWRDFFPYLKWVPNKKFENTIQQMYIRRKAVMKALIKEHKKRIASGENLNSYI
KOeng    MMGAIDVDWRDFFPYLKWVPNKKFENTIQQMYIRREAVMKSLIKEQKKRIASGEKLNSYI
HaKO     MMGAIDVDWRDFFPYLKWVPNKKFENTIQQMYIRREAVMKALIKQHKERIASGEKLNSYI
         : ***:********* :**..*** *::  : *:****:** ::.:** ***:*****
```

MICROBIAL PRODUCTION OF ROTUNDONE

RELATED APPLICATIONS

This application claims the benefit of U.S. Provisional Application No. 62/727,815, filed Sep. 6, 2018, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MAN-019PC Sequence Listing_ST25; date recorded: Sep. 6, 2019; file size: 235,920 bytes).

BACKGROUND

Rotundone is an oxygenated sesquiterpene (sesquiterpenoid) that is responsible for a pleasing spicy, 'peppery' aroma in various plants, including grapes (especially syrah or shiraz, mourvèdre, durif, vespolina, and grüner veltliner varietals), and a large number of herbs and spices, such as, e.g., black and white pepper, oregano, basil, thyme, marjoram, and rosemary. Given its aroma, rotundone is an attractive molecule for applications in fragrances and flavors.

α-Guaiene is the precursor to (−)-rotundone. α-Guaiene is a sesquiterpene hydrocarbon found in oil extracts from various plants, and is converted to (−)-rotundone by aerial oxidation or enzymatic transformation.

Given the commercial value of rotundone, cost effective, scalable, and/or sustainable processes for its production are needed.

SUMMARY

In various aspects, the present disclosure provides methods and compositions for producing rotundone. In various aspects, the present disclosure provides enzymes, polynucleotides encoding said enzymes, and recombinant microbial host cells (or microbial host strains) for the production of rotundone. In some embodiments, the present disclosure provides microbial host cells for producing rotundone at high purity and/or yield, from either enzymatic transformation of α-guaiene, or from sugar or other carbon source. The present disclosure further provides methods of making products containing rotundone, including flavor or fragrance products, among others.

In some embodiments, the present disclosure provides a microbial host cell expressing an enzyme pathway catalyzing the conversion of farnesyl diphosphate (FPP) to rotundone, the enzymatic pathway comprising an α-guaiene terpene synthase enzyme (αGTPS) and an α-guaiene oxidase (αGOX) enzyme. In these embodiments, the microbial cells can synthesize rotundone product from any suitable carbon source. In some embodiments, the specificity of the α-guaiene synthase enzyme enables production of rotundone at high yield with fewer terpenoid byproducts. In some embodiments, the αGOX produces rotundone as the predominant oxygenated product.

In some embodiments, the microbial host cell further expresses or overexpresses one or more enzymes in the methylerythritol phosphate (MEP) and/or the mevalonic acid (MVA) pathway to catalyze the conversion of glucose or other carbon sources to isopentenyl pyrophosphate (IPP) and/or dimethylallyl pyrophosphate (DMAPP). In some embodiments, the microbial host cell further expresses an enzyme catalyzing the conversion of IPP and/or DMAPP to farnesyl diphosphate (FPP), allowing for rotundone to be produced from sugar or other carbon sources (carbon substrates such as C1, C2, C3, C4, C5, and/or C6 carbon substrates). In some embodiments, the host cell is a bacteria engineered to increase carbon flux through the MEP pathway.

In some embodiments, the microbial host cell expresses an α-guaiene oxidase (αGOX) enzyme, which may be a P450 enzyme, non-heme iron oxygenase (NHIO), or laccase providing for biotransformation of α-guaiene substrate. α-Guaiene substrate can be added to whole cell or cellular extracts or purified enzyme. In some embodiments, the cell further expresses at least one cytochrome P450 reductase to support P450 enzyme activity for whole cell bioconversion processes. In some embodiments, the αGOX produces rotundone as the predominant oxygenated product.

In some embodiments, the microbial host cell further expresses one or more alcohol dehydrogenases. In some embodiments, the alcohol dehydrogenase converts one or more alcohol intermediates, produced by the reaction of α-guaiene with αGOX, to rotundone.

In some embodiments, the microbial host cell is prokaryotic or eukaryotic, and may be a bacteria or yeast.

Other aspects and embodiments of the invention will be apparent from the following detailed disclosure.

BRIEF DESCRIPTION OF THE FIGURES

FIG. 4 shows results from the screening of amino acid substitutions in an exemplary α-guaiene terpene synthase (AcDGuaS3, SEQ ID NO: 8). Derivatives were tested for α-guaiene production in E. coli. The figure shows fold improvement in α-guaiene production.

FIG. 5 lists the altered profile toward production of α-guaiene in E. coli for several amino acid substitutions in AcDGuaS3. Fold improvement of α-guaiene as a % of the total products is listed.

FIG. 8A shows the abundance of rotundone in GC/MS and FIG. 8B shows the gas chromatogram for rotundone.

FIG. 10 shows a multiple sequence alignment of five kaurene oxygenases, including KOeng (SEQ ID NO: 51), which functions as α-guaiene oxidase enzyme. The homologs are HaKO (SEQ ID NO: 50), AaKO (SEQ ID NO: 49), CcKO (SEQ ID NO: 47), LsKO (SEQ ID NO: 46), and NtKO (SEQ ID NO: 45).

DETAILED DESCRIPTION

In various aspects, the present disclosure provides microbial host cells (or microbial host strains) and methods for producing rotundone and methods of making products containing rotundone, such as flavor and fragrance products, among others. In other aspects, the present invention provides enzymes and polynucleotides encoding enzymes for the production of rotundone.

In some embodiments, the present disclosure provides a microbial host cell, including bacteria and yeast, expressing an enzyme pathway catalyzing the conversion of farnesyl diphosphate (FPP) to rotundone. In various embodiments, the enzymatic pathway comprises a α-guaiene synthase enzyme (αGTPS) and an α-guaiene oxidase (αGOX) enzyme. In these embodiments, the microbial cells can synthesize rotundone product from any suitable carbon source. In some embodiments, the specificity of the α-guaiene synthase enzyme enables production of rotundone at high yield with fewer terpenoid byproducts. In some embodiments, the microbial host cell may further expresses one or more alcohol dehydrogenase enzymes (ADH). In some embodiments, the ADH converts one or more alcohol intermediates, produced by the reaction of α-guaiene with αGOX, to rotundone.

In some embodiments, the microbial host cell expresses an α-guaiene oxidase (αGOX) enzyme, providing for biotransformation of α-guaiene substrate. In some embodiments, αGOX is a P450 enzyme, non-heme iron oxygenase (NHIO), or laccase. In some embodiments, the cell may further express a cytochrome P450 reductase to support P450 activity. In some embodiments, the microbial host cell may further express one or more alcohol dehydrogenase enzymes (ADH). In some embodiments, the ADH converts one or more alcohol intermediates, produced by the reaction of α-guaiene with αGOX, to rotundone.

Figure 1:
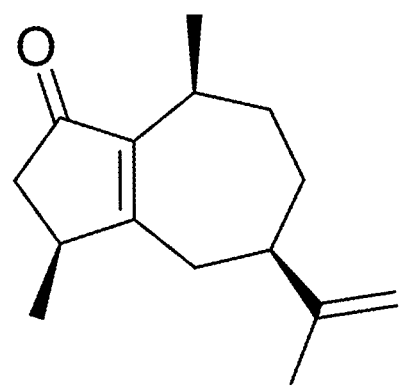
FIG. 1 shows the chemical structure of rotundone.

Rotundone comprises a guaiene carbon skeleton with a single ketone group in the carbon 2 position (see FIG. 1). α-Guaiene is the precursor to rotundone. α-Guaiene is a sesquiterpene hydrocarbon found in oil extracts from various plants. While α-guaiene can be converted to rotundone by aerial oxidation or enzymatic transformation, these processes are not efficient, in part due to the specificity of enzymes used.

Figure 2:
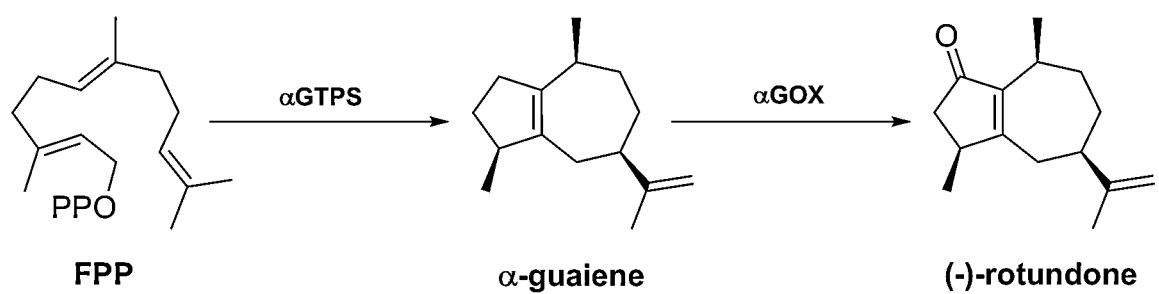
FIG. 2 illustrates a biosynthetic pathway for the production of rotundone. Farnesyl diphosphate is converted to α-guaiene by an α-guaiene terpene synthase (αGTPS) enzyme; and α-guaiene is converted to (−)-rotundone by an α-guaiene oxidase (αGOX) enzyme.

A biosynthetic pathway for rotundone is shown in FIG. 2. The C15 sesquiterpene precursor substrate farnesyl diphosphate (FPP) is cyclized to α-guaiene by an αGTPS terpene synthase enzyme. The α-guaiene (i.e., cyclized FPP) is then oxidized to rotundone via an αGOX enzyme. The production of the ketone moiety in α-guaiene resulting in rotundone can proceed directly, or can alternatively proceed through alcohol intermediates, with either stereochemistry of the alcohol intermediate, i.e., (2R)-rotundol or (2S)-rotundol (see FIG. 3).

The αGTPS enzyme is a terpene synthase enzyme (TPS). TPS enzymes are responsible for the synthesis of the terpene molecules from two isomeric 5-carbon precursor building blocks, leading to 5-carbon isoprene, 10-carbon monoterpenes, 15-carbon sesquiterpenes and 20-carbon diterpenes. The structures and functions of TPS enzymes are described in Chen et al., *The Plant Journal*, 66: 212-229 (2011). Tobacco 5-epi-aristolochene synthase, a terpene synthase, has been described along with structural coordinates, including key active site coordinates. These structural coordinates can be used for constructing homology models of αGTPS enzymes, which are useful for guiding the engineering of αGTPS enzymes with improved specificity and productivity. See, U.S. Pat. Nos. 6,645,762, 6,495,354, and 6,645,762, which are hereby incorporated by reference in their entireties.

In some embodiments, the TPS enzyme is selected from *Vitis vinifera* GuaS (VvGuas) enzyme (SEQ ID NO: 1), patchouli synthase (PcPS) enzyme from *Pogostemon cablin* (Uniprot Q49SP3) (SEQ ID NO: 2), *Vitis vinifera* germacrene D synthase (VvGDS; NCBI Ref #XP_002282488.1) (SEQ ID NO: 21), or a variant thereof. In some embodiments, the TPS enzyme is selected from *Aquilaria crassna*, for example, AcC1 (Uniprot DOVMR5); AcC2 (Uniprot DOVMR6) (SEQ ID NO: 3); AcC3 (Uniprot DOVMR7) (SEQ ID NO: 4); or AcC4 (Uniprot DOVMR8) (SEQ ID NO: 5), or a variant thereof. In some embodiments, the *A. crassna* TPS is a mutant of AcC1, for example AcC1mut1-M42 (SEQ ID NO: 6) and AcC1mut2-M50 (SEQ ID NO: 7). Other TPS enzymes are provided herein as SEQ ID NO:8 (*Aquilaria crassna* AcDGuaS3), SEQ ID NO:9 (*Aquilaria crassna* AcDGuaS4), SEQ ID NO:10 (*Aquilaria crassna* AcDGuaS2), SEQ ID NO:11 (*Aquilaria crassna* AcDGuaS5), SEQ ID NO: 12 (*Aquilaria* spp. AmiDGuaS1), SEQ ID NO: 13 (*Aquilaria* spp. AmiDGuaS2), SEQ ID NO: 14 (*Aquilaria* spp. AmiDGuaS3), SEQ ID NO: 15 (*Aquilaria* spp. AmaDGuaS1), SEQ ID NO: 16 (*Aquilaria* spp. AmaDGuaS2), SEQ ID NO: 17 (*Aquilaria* spp. AsDGuaS1), SEQ ID NO: 18 (*Aquilaria* spp. AsDGuaS2), SEQ ID NO: 19 (*Aquilaria* spp. AsDGuaS3), and SEQ ID NO: 20 (*Aquilaria* spp. AsDGuaS4), or a variant thereof.

Terpene synthase variants include α-guaiene synthase enzymes comprising an amino acid sequence that has 50% or more sequence identity with any one of SEQ ID NOs: 1 to 21. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOs: 1 to 21. In some embodiments, the variant includes from 1 to about 20, or from 1 to about 10, or from 1 to about 5 amino acid modifications independently selected from substitutions, deletions, and insertions to an amino acid sequence selected from SEQ ID NOs: 1 to 21. In some embodiments, the terpene synthase comprises a substitution to one or more of the substrate binding site or active site. In some embodiments, modifications to enzymes can be informed by construction of a homology model. In some embodiments, the amino acid modifications can be selected to improve one or more of: enzyme productivity, selectivity for the desired substrate and/or product, stability, temperature tolerance, and expression.

In some embodiments, the α-guaiene synthase enzyme comprises an amino acid sequence that has at least 50% sequence identity with any one of SEQ ID NOs: 1, 3, 4, 6 to 10, 11 to 15, or 19. In some embodiments, the α-guaiene synthase enzyme comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOs: 1, 3, 4, 6 to 10, 11 to 15, or 19. In some embodiments, the α-guaiene synthase enzyme includes from 1 to about 20, or from 1 to about 10, or from 1 to about 5 amino acid modifications independently selected from substitutions, deletions, and insertions to an amino acid sequence selected from SEQ ID NOs: 1, 3, 4, 6 to 10, 11 to 15, or 19.

In some embodiments, the α-guaiene synthase enzyme comprises an amino acid sequence that has 50% or more sequence identity with SEQ ID NO: 8. In some embodiments, the α-guaiene synthase enzyme comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of SEQ ID NO: 8. In some embodiments, the α-guaiene synthase enzyme includes from 1 to about 20, or from 1 to about 10, or from 1 to about 5 amino acid modifications independently selected from substitutions, deletions, and insertions to the amino acid sequence of SEQ ID NO: 8.

In some embodiments, the α-guaiene synthase may have one, two, three, four, five or more amino acid substitutions at positions corresponding to positions selected from 72, 273, 290, 368, 371, 374, 377, 381, 382, 399, 406, 419, 433, 442, 443, 454, 512, and 522 of SEQ ID NO: 8. For example, in some embodiments the α-GTPS comprises an amino acid sequence having one or more (e.g, 2, 3, 4, 5, or all) of the amino acid substitutions selected from T72I, M273L, R290K, F368M, I371L, S374A, R377V, Y381W, F382L, I399V, F406L, L419T, V433I, Y442L, I443M, E454K, F512L, and K522D relative to SEQ ID NO: 8. In some embodiments, the α-GTPS includes an amino acid substitution at the position corresponding to position 406 of SEQ ID NO: 8, and which is optionally F406L, F406A, F406I, F406V, or F406G. In some embodiments, the α-GTPS enzyme includes an amino acid substitution at the position corresponding to position 443 of SEQ ID NO: 8, which is optionally I443M. In some embodiments, the α-GTPS enzyme includes a mutation at the position corresponding to position 512 of SEQ ID NO: 8, which is optionally F512L, F512A, F512I, F512V, or F512G.

Amino acid substitutions may be conservative or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, Ile;
(2) neutral hydrophilic: Cys, Ser, Thr; Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (iii) Asn and Gln; (iv) Lys and Arg; and (v) Tyr and Phe.

As used herein, "non-conservative substitutions" or "non-conservative amino acid exchanges" are defined as exchanges of an amino acid by another amino acid listed in a different group of the six standard amino acid groups (1) to (6) shown above.

Mutations in α-GTPS enzymes can be guided by homology models using molecular structures/models of sesquiterpene synthase disclosed in Drew et al., J. of Exp. Botany, Vol. 67, No. 3, pp. 799-808 (2015) and/or Kumeta et al., Plant Physiology, Vol. 154, pp. 1998-2007 (2010), which are hereby incorporated by reference in its entirety.

The similarity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST protein searches may be performed with the BLASTP program, score=50, word length=3. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

TPS enzymes can generate multiple products with the guaiene skeleton from FPP with varied amounts of α-guaiene produced by different TPS enzymes. In some embodiments, the α-guaiene synthase (or engineered variant) produces predominantly α-guaiene (e.g., greater than 50%) as the product from FPP substrate. In some embodiments, the α-guaiene synthase produces greater than about 75%, or greater than about 80%, or greater than about 85%, or greater than about 90%, or greater than about 95% α-guaiene as the product from FPP. Enzyme specificity can be determined in host microbial cells producing FPP and expressing the α-guaiene synthase, followed by chemical analysis of total terpenoid products. In some embodiments, the α-guaiene produced in the αGTPS reaction is oxidized to rotundone. In some embodiments, an αGOX enzyme oxidizes α-guaiene to rotundone. In some embodiments, the αGOX oxidizes at least one portion of the α-guaiene to a ketone. In some embodiments, the oxidation of α-guaiene by αGOX results in the production of one or more alcohol intermediates. In some embodiments, the alcohol intermediates are converted to rotundone by one or more alcohol dehydrogenases.

In some embodiments, the αGOX enzyme is a cytochrome P450 (CYP450) enzyme. CYP450 enzymes are involved in the formation (synthesis) and breakdown (metabolism) of various molecules and chemicals within cells. CYP450 enzymes have been identified in all kingdoms of life (i.e., animals, plants, fungi, protists, bacteria, archaea, and even in viruses). Illustrative structure and function of CYP450 enzymes are described in Uracher et al., *TRENDS in Biotechnology*, 24(7): 324-330 (2006). In some embodiments, the P450 enzymes are engineered to have a deletion of all or part of the wild type N-terminal transmembrane region, and the addition of a transmembrane domain derived from an *E. coli* inner membrane cytoplasmic C-terminus protein. In various embodiments, the transmembrane domain is a single-pass transmembrane domain. In various embodiments, the transmembrane domain (or "N-terminal anchor") is derived from an *E. coli* gene selected from waaA, ypfN, yhcB, yhbM, yhhm, zipA, ycgG, djlA, sohB, lpxK, F11O, motA, htpx, pgaC, ygdD, hemr, and ycls. These genes were identified as inner membrane cytoplasmic C-terminus proteins through bioinformatic prediction as well as experimental validation. The invention may employ an N-terminal anchor sequence that is a derivative of the *E. coli* wild-type transmembrane domain, that is, having one or more mutations (e.g., amino acid substitutions) with respect to the wild-type sequence. Methods of making such engineered P450 enzymes as well as engineered P450 enzymes are described in U.S. Patent Publication No. 2018/0251738, which is hereby incorporated by reference in its entirety.

In some embodiments, the CYP450 is selected from the *V. vinifera* VvSTO2 (CYP71BE5; Uniprot F6I534) (SEQ ID NO: 22); *Bacillus subtilis* CYP152A1 (Uniprot O31440) (SEQ ID NO: 23); *B. subtilis* CYP107K1 (Uniprot A5HNX5) (SEQ ID NO: 24); *Bacillus cereus* CYP106 (Uniprot Q737I9) (SEQ ID NO: 25); and *B. cereus* CYP107 (Uniprot Q737F2) (SEQ ID NO: 26); or a variant thereof.

αGOX variants include enzymes comprising an amino acid sequence that has 50% or more sequence identity with any one of SEQ ID NOS: 22 to 26. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOS: 22 to 26. In some embodiments, the variant includes from 1 to about 20, or from 1 to about 10, or from 1 to about 5 amino acid modifications independently selected from substitutions, deletions, and insertions to an amino acid sequence selected from SEQ ID NO: 22 to 26. In some embodiments, the oxygenase comprises a substitution to one or more of the substrate binding site or active site. In some embodiments, modifications to enzymes can be informed by construction of a homology model. In some embodiments, selection and modification of enzymes is informed by assaying activity on α-guaiene substrate. In some embodiments, the amino acid modifications can be selected to improve one or more of: enzyme productivity, selectivity for the desired substrate and/or product, stability, temperature tolerance, and expression.

In some embodiments, the αGOX enzyme is a non-heme iron oxygenase (NHIO) or a laccase. In some embodiments, the laccase is derived from bacteria or fungi (including filamentous fungi and yeasts). By way of example, in some embodiments, the laccase is from a species selected from *Aspergillus*, *Neurospora* (e.g., *N. crassa*), *Podospora*, *Botrytis*, *Collybia*, *Fomes*, *Lentinus*, *Lentinus*, *Pleurotus*, *Trametes*, *Rhizoctonia* (e.g., *R. solani*), *Coprinus* (e.g., *C. plicatilis*), *Psatyrella*, *Mycehophtera* (e.g., *M. thermophila*), *Schytalidium*, and *Polyporus*, (e.g., *P. pinsitus*), *Phiebia*, and *Coriolus*, or is a derivative thereof.

In some embodiments, the CYP450 (αGOX) comprises an amino acid sequence that has at least 50% identity to SEQ ID NO: 51. In some embodiments, the CYP450 enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 51. For example, the CYP450 enzyme may comprise an amino acid sequence having from 1 to 20 or from 1 to 10 amino acid modifications with respect to SEQ ID NO: 51, the amino acid modifications being independently selected from amino acid substitutions, deletions, and insertions with respect to corresponding positions in SEQ ID NO: 51.

In some embodiments, the CYP450 comprises an amino acid sequence that has at least 50% identity to SEQ ID NO: 52. In some embodiments, the CYP450 enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least about 98%, or at least 99% identical to SEQ ID NO: 52. For example, the CYP450 enzyme may comprise an amino acid sequence having from 1 to 20 or from 1 to 10 amino acid modifications with respect to SEQ ID NO: 52, the amino acid modifications being independently selected from amino acid substitutions, deletions, and insertions with respect to corresponding positions in SEQ ID NO: 52.

In some embodiments, the CYP450 comprises an amino acid sequence that has at least 50% identity to SEQ ID NOs: 54, 55, or 56. In some embodiments, the CYP450 enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NOs: 54, 55, or 56. For example, the CYP450 enzyme may comprise an amino acid sequence having from 1 to 20 or from 1 to 10 amino acid modifications with respect to SEQ ID NO: 54, 55, or 56, the amino acid modifications being independently selected from amino acid substitutions, deletions, and insertions with respect to corresponding positions in SEQ ID NO: 54, 55, or 56.

Amino acid modification to CYP450 enzymes can be guided by available structures, including those described in Pallan et al., "Structural and kinetic basis of steroid 17a, 20-lyase activity in teleost fish cytochrome P450 17A1 and its absence in cytochrome P450 17A2," *Journal of Biological Chemistry* 290.6 (2015): 3248-3268, which is hereby incorporated by reference in its entirety. Pallan et al. describe a Zebra fish cytochrome P450 17A2 along with structural coordinates, including key active site coordinates. These structural coordinates can be used for constructing homology models of CYP450 enzymes, which are useful for guiding the engineering of CYP450 enzymes with improved specificity and productivity.

In some embodiments, the CYP450 enzyme requires the presence of an electron transfer protein capable of transferring electrons to the CYP450 protein. In some embodiments, this electron transfer protein is a cytochrome P450 reductase (CPR), which can be expressed by the microbial host cell. Various reductases that may be used are described in U.S.

Patent Publication No. 2018/0135081, which is hereby incorporated by reference in its entirety.

Exemplary P450 reductase enzymes include those shown herein as SEQ ID NOs: 27 to 34 or 53, or a variant thereof. Variants generally include enzymes comprising an amino acid sequence that has 50% or more sequence identity with any one of SEQ ID NOs: 27 to 34 or 53. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOs: 27 to 34 or 53. In some embodiments, the variant includes from 1 to about 20, or from 1 to about 10, or from 1 to about 5 amino acid modifications independently selected from substitutions, deletions, and insertions to an amino acid sequence selected from SEQ ID NOs: 27 to 34 or 53.

In some embodiments, the CPR comprises an amino acid sequence that has at least 50% identity to SEQ ID NO: 53 (CaCPR). In some embodiments, the CPR enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 53. For example, the CPR enzyme may comprise an amino acid sequence having from 1 to 20 or from 1 to 10 amino acid modifications with respect to SEQ ID NO: 53, the amino acid modifications being independently selected from amino acid substitutions, deletions, and insertions with respect to corresponding positions in SEQ ID NO: 53.

Figure 3:
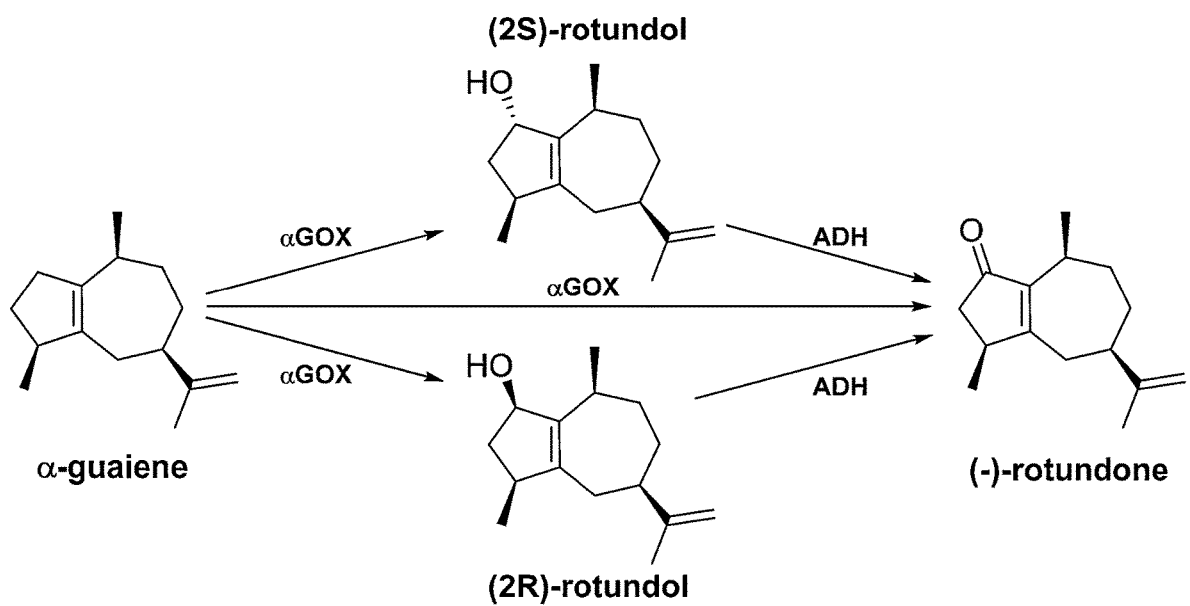
FIG. 3 illustrates that the production of (−)-rotundone from α-guaiene can proceed directly from the sesquiterpene precursor, or can involve the production of one or both alcohol intermediates which are subsequently converted to the ketone by an enzyme with alcohol dehydrogenase activity.

In some embodiments, the αGOX reaction results in hydroxylation of α-guaiene, thereby producing one or more alcohol intermediates, e.g., (2R)-rotundol or (2S)-rotundol (see FIG. 3). In some embodiments, the αGOX further oxidizes at least a portion of the α-guaiene to a ketone. In some embodiments, the alcohol intermediates (e.g., (2R)-rotundol or (2S)-rotundol) are converted to rotundone by one or more alcohol dehydrogenases (ADHs). Thus, in some embodiments, the microbial host cell expresses one or more alcohol dehydrogenases (ADH). By way of example, in some embodiments, the ADH is selected from an enzyme comprising an amino acid sequence selected from SEQ ID NOs: 35 to 44, or a variant thereof. Variants generally include enzymes comprising an amino acid sequence that has 50% or more sequence identity with any one of SEQ ID NOs: 35 to 44. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOS: 35 to 44. In some embodiments, the variant includes from 1 to about 20, or from 1 to about 10, or from 1 to about 5 amino acid modifications independently selected from substitutions, deletions, and insertions to an amino acid sequence selected from SEQ ID NO: 35 to 44. In some embodiments, the amino acid modifications can be selected to improve one or more of: enzyme productivity, selectivity for the desired substrate and/or product, stability, temperature tolerance, and expression.

In some embodiments, the ADH comprises an amino acid sequence that has at least 50% identity to SEQ ID NO: 43 (VvDH). In some embodiments, the ADH enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 43. For example, the ADH enzyme may comprise an amino acid sequence having from 1 to 20 or from 1 to 10 amino acid modifications with respect to SEQ ID NO: 43, the amino acid modifications being independently selected from amino acid substitutions, deletions, and insertions with respect to corresponding positions in SEQ ID NO: 43.

In some embodiments, the microbial cell expresses an αGOX, and produces predominately rotundone (e.g., at least 75% of the oxygenated product is rotundone), without expression of an ADH enzyme.

In various embodiments, the αGTPS and αGOX are expressed together in an operon, or are expressed individually. The enzymes may be expressed from extrachromosomal elements such as plasmids, or bacterial artificial chromosomes, or may be chromosomally integrated.

In some embodiments, the cell does not express an αGTPS, but expresses an α-guaiene oxidase (αGOX), allowing enzymatic biotransformation of α-guaiene, which can take place with whole cells or whole or partially purified extracts of cells.

In some embodiments, the αGOX and/or the ADH are provided in a purified recombinant form for production of rotundone from α-guaiene, or (2R)-rotundol or (2S)-rotundol, in a cell free system.

In some embodiments, the microbial host cell is also engineered to express or overexpress one or more enzymes in the methylerythritol phosphate (MEP) and/or the mevalonic acid (MVA) pathway to catalyze isopentenyl pyrophosphate (IPP) and dimethylallyl pyrophosphate (DMAPP) from glucose or other carbon source.

In some embodiments, the microbial host cell is engineered to express or overexpress one or more enzymes of the MEP pathway. In some embodiments, the MEP pathway is increased and balanced with downstream pathways by providing duplicate copies of certain rate-limiting enzymes. The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA. In some embodiments, the microbial host cell expresses or overexpresses of one or more of dxs, ispC, ispD, ispE, ispF, ispG, ispH, idi, ispA, or modified variants thereof, which results in the increased production of IPP and DMAPP. In some embodiments, rotundone is produced at least in part by metabolic flux through an MEP pathway, and wherein the microbial host cell has at least one additional gene copy of one or more of dxs, ispC, ispD, ispE, ispF, ispG, ispH, idi, ispA, or modified variants thereof.

In some embodiments, the microbial host cell is engineered to express or overexpress one or more enzymes of the MVA pathway. The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MVA pathway, are described in U.S. Pat. No. 7,667,017, which is hereby incorporated by reference in its entirety. In some embodiments, the microbial host cell expresses or overexpresses one or more of acetoacetyl-CoA thiolase, HMGS, HMGR, MK, PMK, and MPD or modified variants thereof, which results in the increased production of IPP and DMAPP. In some embodiments, rotundone is produced at least in part by metabolic flux through an MVA pathway, and wherein the microbial host cell has at least one additional gene copy of one or more of acetoacetyl-CoA thiolase, HMGS, HMGR, MK, PMK, MPD, or modified variants thereof.

In some embodiments, the microbial host cell is engineered to increase production of IPP and DMAPP from glucose as described in PCT Application Nos. PCT/US2018/016848 and PCT/US2018/015527, the contents of which are hereby incorporated by reference in their entireties. For example, in some embodiments the microbial host cell overexpresses MEP pathway enzymes, with balanced expression to push/pull carbon flux to IPP and DMAPP. In some embodiments, the microbial host cell is engineered to increase the availability or activity of Fe—S cluster proteins, so as to support higher activity of IspG and IspH, which are Fe—S enzymes. In some embodiments, the host cell is engineered to overexpress IspG and IspH, so as to provide increased carbon flux to 1-hydroxy-2-methyl-2-(E)-butenyl 4-diphosphate (HMBPP) intermediate, but with balanced expression to prevent accumulation of HMBPP at an amount that reduces cell growth or viability, or at an amount that inhibits MEP pathway flux.

Conversion of IPP and DMAPP precursors to farnesyl diphosphate (FPP) is typically through the action of a farnesyl diphosphate synthase (FPPS). Exemplary FPPS enzymes are disclosed in US 2018/0135081, which is hereby incorporated by reference in its entirety.

In some embodiments, the host cell is engineered to downregulate the ubiquinone biosynthesis pathway, e.g., by reducing the expression or activity of IspB, which uses IPP and FPP substrate.

In some embodiments, the microbial host cell is a bacteria selected from *Escherichia* spp., *Bacillus* spp., *Corynebacterium* spp., *Rhodobacter* spp., *Zymomonas* spp., *Vibrio* spp., and *Pseudomonas* spp. For example, in some embodiments, the bacterial host cell is a species selected from *Escherichia coli*, *Bacillus subtilis*, *Corynebacterium glutamicum*, *Rhodobacter capsulatus*, *Rhodobacter sphaeroides*, *Zymomonas mobilis*, *Vibrio natriegens*, or *Pseudomonas putida*. In some embodiments, the bacterial host cell is *E. coli*.

In some embodiments, the microbial host cell is a species of *Saccharomyces*, *Pichia*, or *Yarrowia*, including, but not limited to, *Saccharomyces cerevisiae*, *Pichia pastoris*, and *Yarrowia lipolytica*.

In another aspect, the present disclosure provides a method for making rotundone. The method comprises providing a microbial host cell (or microbial host strain) as disclosed herein. The microbial host cell expresses an αGOX enzyme, and optionally an αGTPS enzyme as described herein. Cells expressing an αGOX enzyme can be used for bioconversion of α-guaiene using whole cells or cell extracts. Cells expressing an αGOX enzyme and an αGTPS enzyme can produce rotundone from a carbon source.

In some embodiments, the microbial host cell further expresses one or more alcohol dehydrogenases (ADHs) disclosed herein. Cells expressing ADHs can convert alcohol intermediates produced by the αGOX reaction into rotundone.

In some embodiments, the host cell is cultured to produce rotundone. In some embodiments, microbial cells are cultured with carbon substrates (sources) such as C1, C2, C3, C4, C5, and/or C6 carbon substrates. In exemplary embodiments, the carbon source is glucose, sucrose, fructose, xylose, and/or glycerol. Culture conditions are generally selected from aerobic, microaerobic, and anerobic.

In various embodiments, the host cell is cultured at a temperature between 22° C. and 37° C. While commercial biosynthesis in bacteria such as *E. coli* can be limited by the temperature at which overexpressed and/or foreign enzymes (e.g., enzymes derived from plants) are stable, recombinant enzymes (including the terpenoid synthase) may be engineered to allow for cultures to be maintained at higher temperatures, resulting in higher yields and higher overall productivity. In some embodiments, the host cell is a bacterial host cell, and culturing is conducted at about 22° C. or greater, about 23° C. or greater, about 24° C. or greater, about 25° C. or greater, about 26° C. or greater, about 27° C. or greater, about 28° C. or greater, about 29° C. or greater, about 30° C. or greater, about 31° C. or greater, about 32° C. or greater, about 33° C. or greater, about 34° C. or greater, about 35° C. or greater, about 36° C. or greater, or about 37° C.

Rotundone can be extracted from media and/or whole cells, and recovered. In some embodiments, the oxygenated rotundone product is recovered and optionally enriched by fractionation (e.g. fractional distillation). The oxygenated product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, oxidized oil is extracted from aqueous reaction medium, which may be done by partitioning into an organic phase, followed by fractional distillation. Sesquiterpene and sesquiterpenoid components of fractions may be measured quantitatively by GC/MS, followed by blending of the fractions.

In some embodiments, the microbial host cells and methods disclosed herein are suitable for commercial production of rotundone, that is, the microbial host cells and methods are productive at commercial scale. In some embodiments, the size of the culture is at least about 100 L, at least about 200 L, at least about 500 L, at least about 1,000 L, at least about 10,000 L, at least about 100,000 L, or at least about 1,000,000 L. In some embodiment, the culturing may be conducted in batch culture, continuous culture, or semi-continuous culture.

In some aspects, the present disclosure provides methods for making a product comprising rotundone, including flavor and fragrance compositions or products. In some embodiments, the method comprises producing rotundone as described herein through microbial culture, recovering the rotundone, and incorporating the rotundone into the flavor or fragrance composition, or a consumable product (e.g., a food product).

As used in this specification and the appended claims, the singular forms "a", "an" and "the" include plural referents unless the content clearly dictates otherwise. For example, reference to "a cell" includes a combination of two or more cells, and the like.

As used herein, the term "about" in reference to a number is generally taken to include numbers that fall within a range of 10% in either direction (greater than or less than) of the number.

EXAMPLES

Rotundone is a bicyclic sesquiterpene (FIG. 1) and is responsible for pepper aromas in grapes and wine and in herbs and spices, especially black and white pepper, where it has a high odor activity value (OAV). The biosynthesis of rotundone involves cyclization of the C15 sesquiterpene precursor substrate farnesyl diphosphate (FPP) to α-guaiene by an α-GTPS terpene synthase (FIG. 2). Enzymatic oxygenation of α-guaiene can produce rotundone, and may proceed through an alcohol intermediate (FIGS. 2 and 3). For example, α-guaiene may be converted to (2S)-rotundol or (2R)-rotundol by the action of αGOX, and the alcohol intermediate(s) (rotundol) can be converted to rotundone by the action of the αGOX or an alcohol dehydrogenase.

Example 1: Engineering α-Guaiene Synthase to Improve α-Guaiene Production

The α-guaiene precursor, rotundol, or rotundone can be produced by biosynthetic fermentation processes, using microbial strains that produce high levels of MEP pathway products, along with heterologous expression of rotundone biosynthesis enzymes, including, enzymes that catalyze 1) cyclization of FPP to α-guaiene; 2) oxidation of α-guaiene to rotundone, which can include 3) dehydrogenation of rotundol to rotundone. For example, in bacteria such as E. coli, isopentenyl pyrophosphate (IPP) and dimethylallyl pyrophosphate (DMAPP) can be produced from glucose or other carbon source, and which can be converted to farnesyl diphosphate (FPP) by recombinant farnesyl diphosphate synthase (FPPS). FPP is converted to α-guaiene by α-guaiene synthase (αGTPS) by cyclization. The α-guaiene is converted to rotundol or rotundone by oxygenation reaction catalyzed by an α-guaiene oxidase (αGOX). In instances where the αGOX enzyme catalyzes the production of (2S)-rotundol or (2R)-rotundol from α-guaiene, the conversion of rotundol to rotundone may be catalyzed by a dehydrogenase.

Using an E. coli background strain that produces high levels of the MEP pathway products IPP and DMAPP (see US 2018/0245103 and US 2018/0216137, which are hereby incorporated by reference), candidate αGTPS enzymes were screened by co-expression with FPPS. Fermentation was performed in 96 well plates for 48 hours. The following synthase enzymes demonstrated production of α-guaiene in E. coli: AcC1mut1_M42, AcC1mut2 M50, AcC2, AcC3, AcDGuaS2, AcDGuaS3, AcDGuaS4, AcDGuaS5, AmaDGuaS1, AmiDGuaS1, AmiDGuaS2, AmiDGuaS3, AsDGuaS3, PcPS, and VvGuaS. In addition to the desired α-guaiene product, active enzymes had varying product profiles. For example, all active Aquilaria enzymes showed α-bulnesene as a major product with α-guaiene. VvGuaS accumulated α-bulnesene and globulol in similar levels to α-guaiene. AcDGuaS3 was selected for subsequent studies based on its productivity and product profile.

Figure 6:
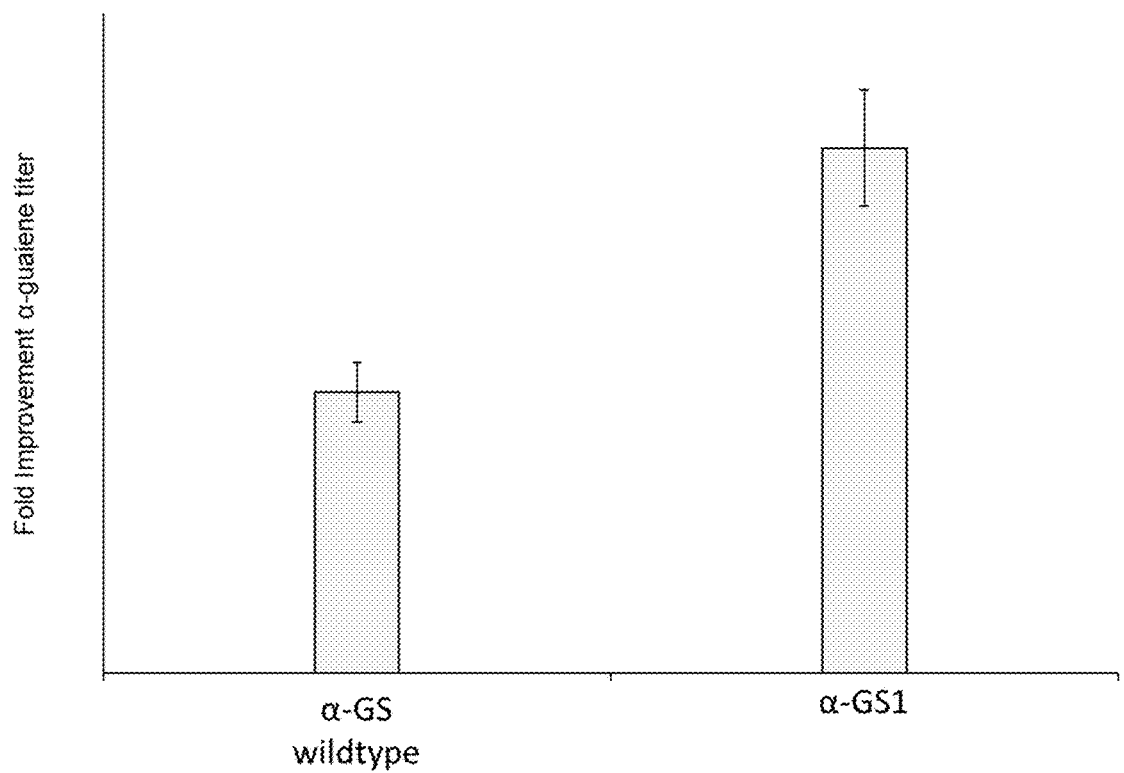
FIG. 6 shows production of α-guaiene with expression of wild-type AcDGuaS3 (α-GS) and mutant AcDGuaS3 having an F406L mutation (α-GS1) in E. coli.

A panel of amino acid substitutions to the AcDGuaS3 sequence were screened for their ability to convert FPP to α-guaiene in E. coli. The fermentation was conducted in 96 well plates for 48 hours. FIG. 4 shows several mutants (i.e., amino acid substitutions) and the associated fold-improvement in α-guaiene production. For example, F406L substitution in AcDGuaS3 demonstrated a significantly improved titer of α-guaiene (1.71 fold higher than wild-type). Amino acid substitutions were further evaluated for substitutions that shift the product profile toward α-guaiene. See FIG. 5. As shown, a single substitution in wild-type AcDGuaS3 (I443M) shows a 2.4 fold improvement in % α-guaiene relative to other products. Similarly, a F406L substitution shows a 2.12 fold improvement in % α-guaiene relative to other products. A F512 mutation demonstrated a 1.23 fold improvement in % α-guaiene relative to other products. FIG. 6 shows the fold improvement in titer of α-guaiene, based on expression of a variant having an F406L substitution in AcDGuaS3 (α-GS1) as compared to the parent enzyme.

Example 2: Production of Rotundone

Figure 7A:
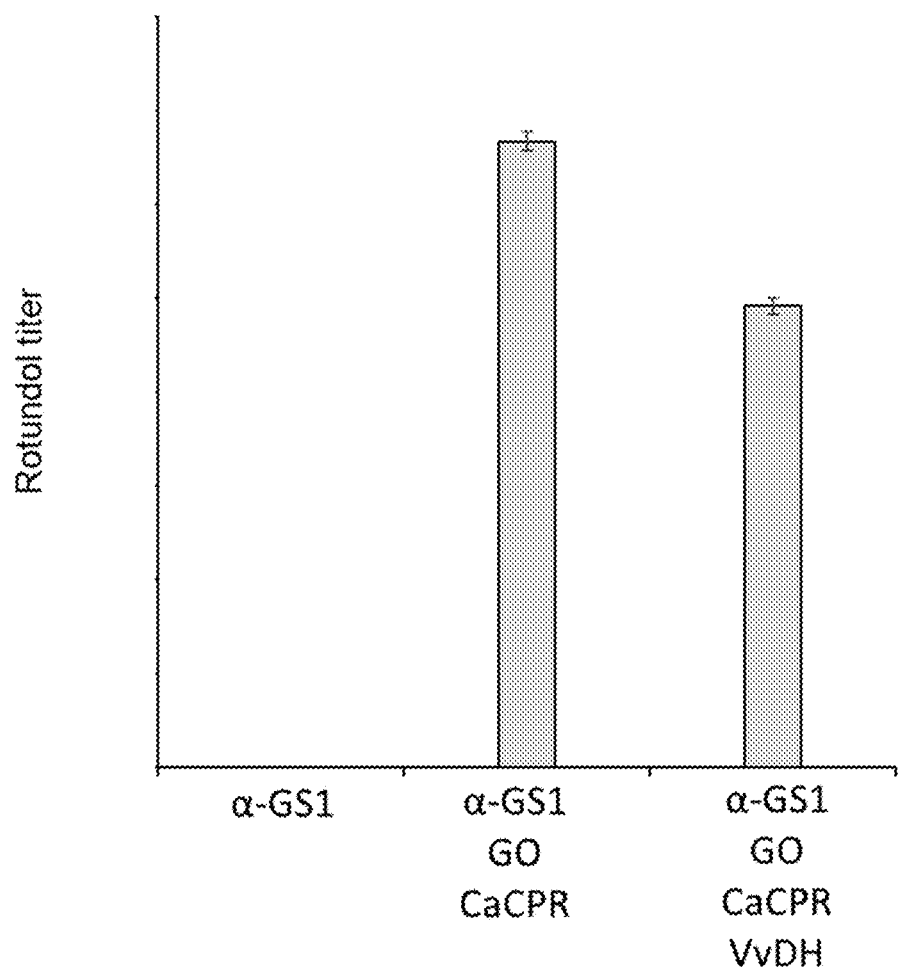
FIGS. 7A and 7B show production of rotundol and rotundone in E. coli expressing α-GS1 and an exemplary CYP450 system (engineered kaurene oxidase; KOeng). Expression of Vitis vinifera dehydrogenase (VvDH) along with α-GS1, KOeng as the α-guaiene oxidase, and Camptotheca acuminata cytochrome P450 reductase (CaCPR) reduces the titer of rotundol (FIG. 7A) and increases rotundone titer (FIG. 7B).
Figure 7B:
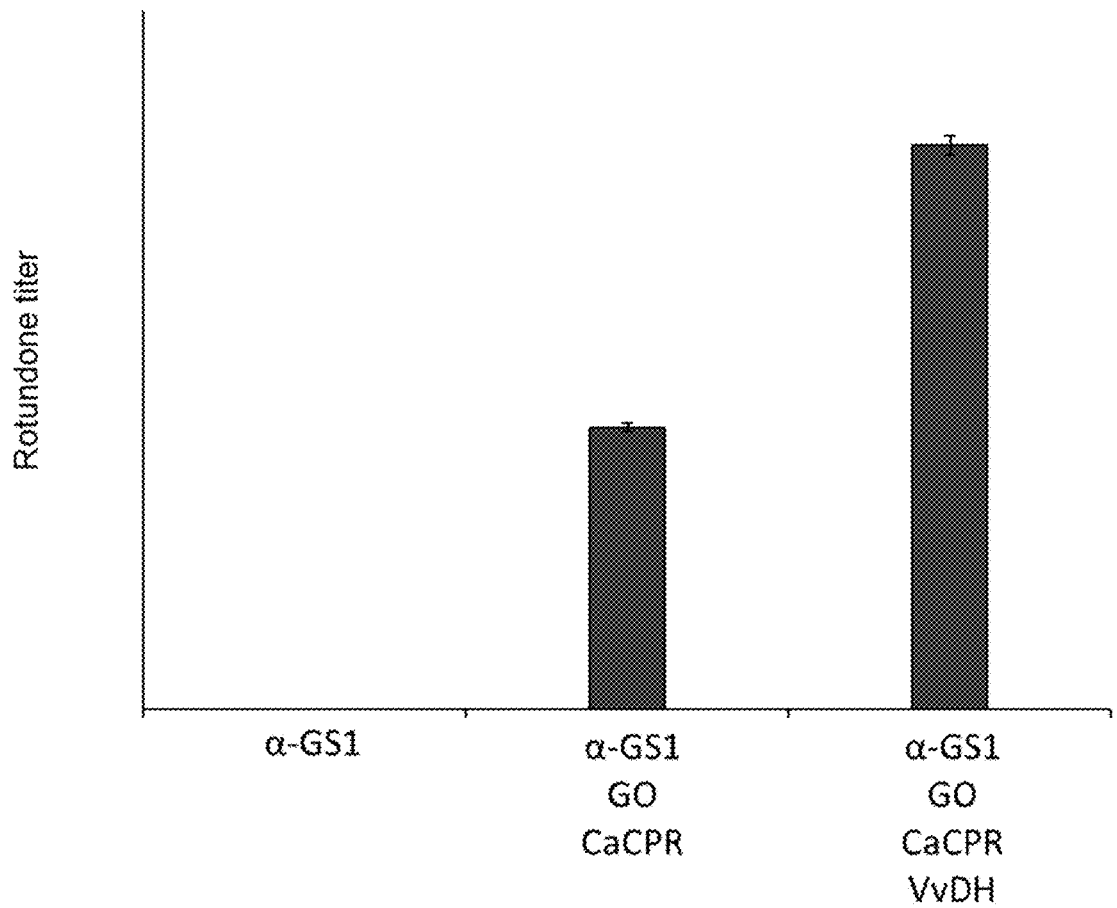
Figure 8A:
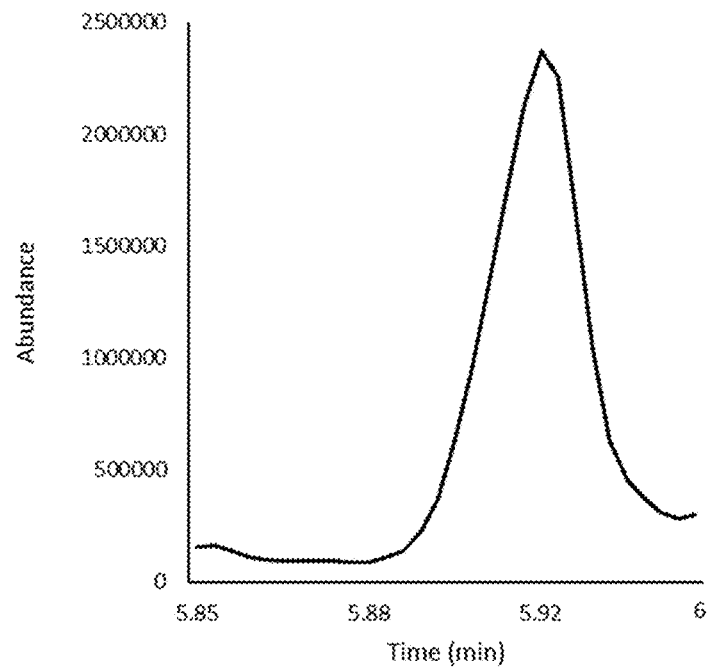
FIGS. 8A and B show Gas-Chromatography/Mass Spectrometry (GC/MS) confirmation of production of rotundone from E. coli strain expressing α-GS1, KOeng, CaCPR, and VvDH.
Figure 8B:
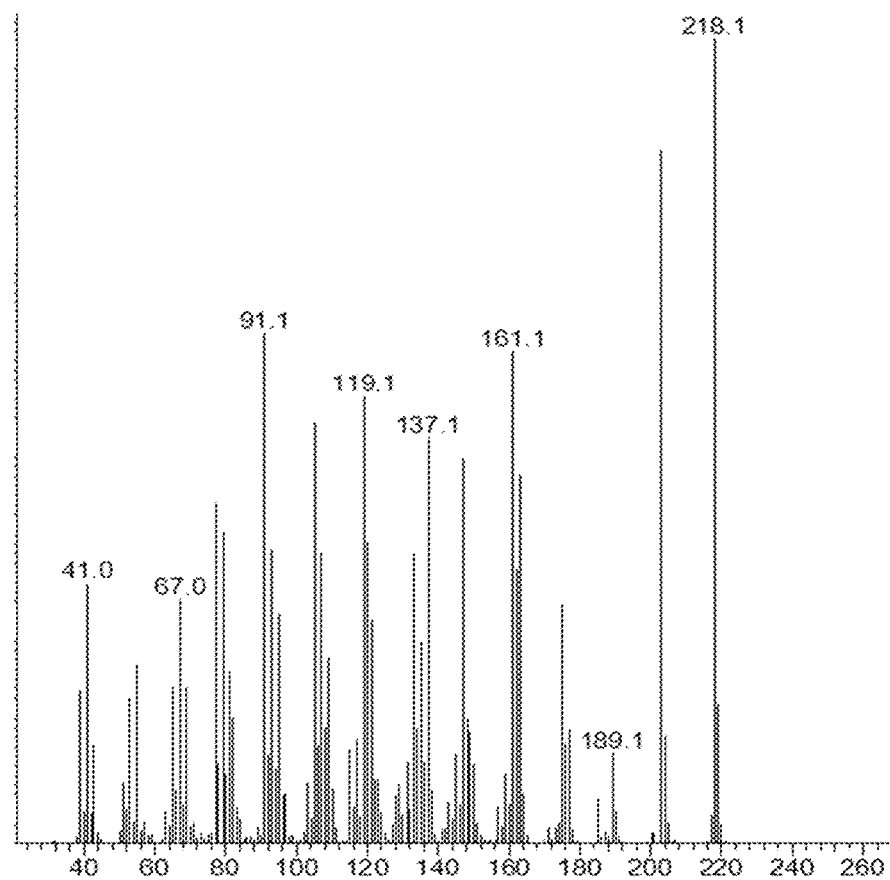

Candidate α-guaiene oxidase enzymes where screened by co-expression in E. coli with FPPS and α-GS1. Production of rotundol and rotundone were observed with expression of an engineered Kaurene Oxidase (KOeng). See, US 2018/0135081, which is hereby incorporated by reference in its entirety. Co-expression of Vitis vinifera dehydrogenase (VvDH) along with α-GS1, KOeng, and Camptotheca acuminata cytochrome P450 reductase (CaCPR) reduces the titer of rotundol (FIG. 7A) and increases rotundone titer (FIG. 7B). Rotundone derived from oxidation of α-guaiene by cytochrome P450 was confirmed by GC/MS (FIGS. 8A and 8B). The KOeng can be further engineered to improve specificity for the α-guaiene substrate. An alignment with wild-type kaurene oxidase enzymes is shown in Example 10, which can assist this engineering.

Figure 9:
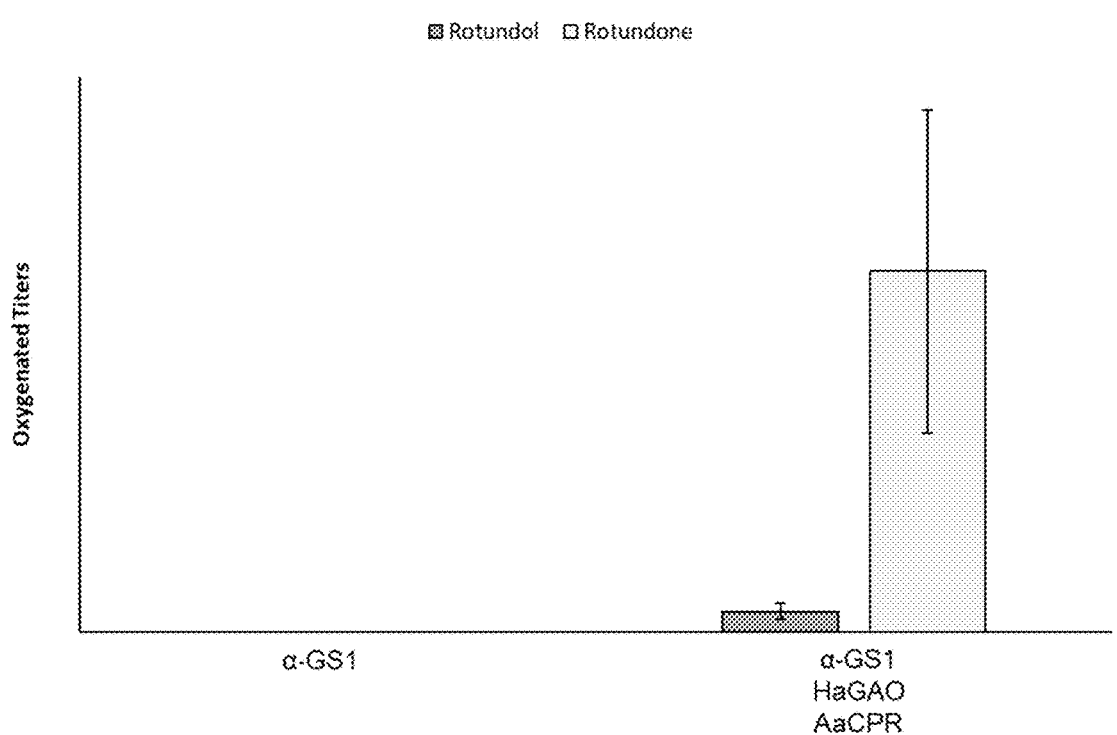
FIG. 9 shows production of rotundol and rotundone in *E. coli* expressing α-GS1 and an alternative CYP450 system. Expression of α-GS1, *Helianthus annuus* germacrene A monooxygenase engineered for expression in *E. coli* (HaGAO), and AaCPR (*Artemisia annua* cytochrome P450 reductase) produces primarily rotundone.

FIG. 9 shows in vivo production of rotundol and rotundone using an alternative CYP450 system, based on expression of Helianthus annuus germacrene A monooxygenase (HaGAO). The E. coli strain included expression of α-GS1, engineered HaGAO for expression in E. coli (SEQ ID NO:52), and AaCPR (Artemisia annua cytochrome P450 reductase; SEQ ID NO: 33). The fermentation was conducted in 96 well plates for 48 hours. As shown in FIG. 9, the oxygenated product was substantially rotundone, with only minor amounts of the rotundol intermediate.

What is claimed is:

1. A microbial host cell for producing rotundone, the microbial cell expressing a heterologous α-guaiene synthase enzyme (αGTPS) and a heterologous α-guaiene oxidase (αGOX) enzyme;
   wherein the αGTPS comprises an amino acid sequence that is at least 80% identical to SEQ ID NO: 8, and having one or more of the following substitutions relative to SEQ ID NO: 8: F406L, I443M, and F512L.

2. The microbial cell of claim 1, further expressing a farnesyl diphosphate synthase.

3. The microbial cell of claim 1, wherein the αGTPS enzyme comprises an amino acid sequence having 90% or more sequence identity to SEQ ID NO: 8.

4. The microbial cell of claim 1, wherein the α-guaiene synthase produces predominantly α-guaiene as a product from farnesyl diphosphate (FPP) substrate.

5. The microbial cell of claim 1, wherein the αGOX enzyme is a cytochrome P450 (CYP450) enzyme.

6. The microbial cell of claim 5, wherein the CYP450 comprises an amino acid sequence that has 95% or more sequence identity with SEQ ID NO: 51 or 52.

7. The microbial cell of claim 6, wherein the microbial cell further expresses a cytochrome P450 reductase comprising an amino acid sequence that is at least 95% identical to SEQ ID NO: 53.

8. The microbial cell of claim 5, wherein the CYP450 comprises an amino acid sequence having 90% or more sequence identity to SEQ ID NO: 51.

9. The microbial cell of claim 5, wherein the CYP450 comprises an amino acid sequence having 90% or more sequence identity to SEQ ID NO: 52.

10. The microbial cell of claim 1, wherein the microbial host cell expresses a cytochrome P450 reductase enzyme.

11. The microbial cell of claim 1, wherein the αGTPS and αGOX are expressed together in an operon.

12. The microbial cell of claim 1, wherein the microbial host cell further expresses one or more alcohol dehydrogenases (ADHs).

13. The microbial cell of claim 12, wherein the ADH comprises an amino acid sequence of any one of SEQ ID NOs: 35-44, or a variant thereof.

14. The microbial cell of claim 12, wherein the ADH comprises an amino acid sequence having 90% or more sequence identity to SEQ ID NO: 43.

15. The microbial cell of claim 1, wherein the microbial host cell overexpresses one or more enzymes in a methylerythritol phosphate (MEP) or a mevalonic acid (MVA) pathway.

16. The microbial cell of claim 1, wherein the microbial cell is a bacterium, optionally selected from *Escherichia* spp., *Bacillus* spp., *Corynebacterium* spp., *Rhodobacter* spp., *Zymomonas* spp., *Vibrio* spp., and *Pseudomonas* spp.

17. The microbial cell of claim 16, wherein the bacterium is *Escherichia coli*.

18. The microbial cell of claim 1, wherein the microbial host cell is a yeast, optionally selected from *Saccharomyces, Pichia*, or *Yarrowia*.

19. The microbial cell of claim 1, wherein the αGTPS enzyme comprises an amino acid sequence having 95% or more sequence identity to SEQ ID NO: 8.

20. A method for making rotundone, comprising: culturing the microbial cell of claim 1, and recovering the rotundone.

21. A method for producing rotundone, comprising feeding α-guaiene to a microbial cell expressing an α-guaiene oxidase (αGOX), or to an extract of the cell, or to a reaction vessel comprising recombinant αGOX, wherein the αGOX comprises an amino acid sequence that has at least 90% sequence identity to SEQ ID NO: 51 or SEQ ID NO: 52.

22. The method of claim 21, wherein the microbial cell is a bacterium.

23. The method of claim 22, wherein the bacterium is *Escherichia coli*.

24. The method of claim 21, wherein the wherein the αGOX comprises an amino acid sequence that has at least 95% sequence identity to SEQ ID NO: 51.

25. The method of claim 24, wherein the microbial cell further expresses a cytochrome P450 reductase comprising an amino acid sequence that is at least 95% identical to SEQ ID NO: 53.

* * * * *

SEQUENCE LISTING

<160> NUMBER OF SEQ ID NOS: 56

<210> SEQ ID NO 1
<211> LENGTH: 561
<212> TYPE: PRT
<213> ORGANISM: Vitis vinifera

<400> SEQUENCE: 1

Met Ser Val Pro Leu Ser Val Ser Val Thr Pro Ile Leu Ser Gln Arg
1               5                   10                  15

Ile Asp Pro Glu Val Ala Arg His Glu Ala Thr Tyr His Pro Asn Phe
            20                  25                  30

Trp Gly Asp Arg Phe Leu His Tyr Asn Pro Asp Asp Asp Phe Cys Gly
        35                  40                  45

Thr His Ala Cys Lys Glu Gln Gln Ile Gln Glu Leu Lys Glu Val
    50                  55                  60

Arg Lys Ser Leu Glu Ala Thr Ala Gly Asn Thr Ser Gln Leu Leu Lys
65                  70                  75                  80

Leu Ile Asp Ser Ile Gln Arg Leu Gly Leu Ala Tyr His Phe Glu Arg
                85                  90                  95

Glu Ile Glu Glu Ala Leu Lys Ala Met Tyr Gln Thr Tyr Thr Leu Val
            100                 105                 110

Asp Asp Asn Asp His Leu Thr Thr Val Ser Leu Leu Phe Arg Leu Leu
        115                 120                 125

Arg Gln Glu Gly Tyr His Ile Pro Ser Asp Val Phe Lys Lys Phe Met
    130                 135                 140

Asp Glu Gly Gly Asn Phe Lys Glu Ser Leu Val Gly Asp Leu Pro Gly
145                 150                 155                 160

Met Leu Ala Leu Tyr Glu Ala Ala His Leu Met Val His Gly Glu Asp
                165                 170                 175

Ile Leu Asp Glu Ala Leu Gly Phe Thr Thr Ala His Leu Gln Ser Met
            180                 185                 190

Ala Ile Asp Ser Asp Asn Pro Leu Thr Lys Gln Val Ile Arg Ala Leu
        195                 200                 205

Lys Arg Pro Ile Arg Lys Gly Leu Pro Arg Val Glu Ala Arg His Tyr
    210                 215                 220

Ile Thr Ile Tyr Gln Glu Asp Asp Ser His Asn Glu Ser Leu Leu Lys
225                 230                 235                 240

Leu Ala Lys Leu Asp Tyr Asn Met Leu Gln Ser Leu His Arg Lys Glu
                245                 250                 255

Leu Ser Glu Ile Thr Lys Trp Trp Lys Gly Leu Asp Phe Ala Thr Lys
            260                 265                 270

Leu Pro Phe Ala Arg Asp Arg Ile Val Glu Gly Tyr Phe Trp Ile Leu
        275                 280                 285

Gly Val Tyr Phe Glu Pro Gln Tyr Tyr Leu Ala Arg Arg Ile Leu Met
    290                 295                 300

Lys Val Phe Gly Val Leu Ser Ile Val Asp Asp Ile Tyr Asp Ala Tyr
305                 310                 315                 320

Gly Thr Phe Glu Glu Leu Lys Leu Phe Thr Glu Ala Ile Glu Arg Trp
                325                 330                 335

Asp Ala Ser Ser Ile Asp Gln Leu Pro Asp Tyr Met Lys Val Cys Tyr
            340                 345                 350

Gln Ala Leu Leu Asp Val Tyr Glu Glu Met Glu Glu Met Thr Lys
        355                 360                 365

-continued

```
Gln Gly Lys Leu Tyr Arg Val His Tyr Ala Gln Ala Ala Leu Lys Arg
        370                 375                 380

Gln Val Gln Ala Tyr Leu Leu Glu Ala Lys Trp Leu Lys Gln Glu Tyr
385                 390                 395                 400

Ile Pro Thr Met Glu Glu Tyr Met Ser Asn Ala Leu Val Thr Ser Ala
                405                 410                 415

Cys Ser Met Leu Thr Thr Thr Ser Phe Val Gly Met Gly Asp Met Val
                420                 425                 430

Thr Lys Glu Ala Phe Asp Trp Val Phe Ser Asp Pro Lys Met Ile Arg
                435                 440                 445

Ala Ser Asn Val Ile Cys Arg Leu Met Asp Asp Ile Val Ser His Glu
            450                 455                 460

Phe Glu Gln Lys Arg Gly His Val Ala Ser Ala Val Glu Cys Tyr Met
465                 470                 475                 480

Lys Gln Tyr Gly Val Ser Lys Glu Glu Ala Tyr Asp Glu Phe Lys Lys
                485                 490                 495

Gln Val Glu Ser Ala Trp Lys Asp Asn Glu Glu Val Leu Gln Pro
                500                 505                 510

Thr Ala Val Pro Val Pro Leu Leu Thr Arg Val Leu Asn Phe Ser Arg
                515                 520                 525

Met Val Asp Val Leu Tyr Lys Asp Glu Asp Glu Tyr Thr Leu Val Gly
            530                 535                 540

Pro Leu Met Lys Asp Leu Val Ala Gly Met Leu Ile Asp Pro Val Pro
545                 550                 555                 560

Met
```

<210> SEQ ID NO 2
<211> LENGTH: 552
<212> TYPE: PRT
<213> ORGANISM: Pogostemnon cablin

<400> SEQUENCE: 2

```
Met Glu Leu Tyr Ala Gln Ser Val Gly Val Gly Ala Ala Ser Arg Pro
1               5                   10                  15

Leu Ala Asn Phe His Pro Cys Val Trp Gly Asp Lys Phe Ile Val Tyr
                20                  25                  30

Asn Pro Gln Ser Cys Gln Ala Gly Glu Arg Glu Glu Ala Glu Glu Leu
            35                  40                  45

Lys Val Glu Leu Lys Arg Glu Leu Lys Glu Ala Ser Asp Asn Tyr Met
        50                  55                  60

Arg Gln Leu Lys Met Val Asp Ala Ile Gln Arg Leu Gly Ile Asp Tyr
65                  70                  75                  80

Leu Phe Val Glu Asp Val Asp Glu Ala Leu Lys Asn Leu Phe Glu Met
                85                  90                  95

Phe Asp Ala Phe Cys Lys Asn Asn His Asp Met His Ala Thr Ala Leu
                100                 105                 110

Ser Phe Arg Leu Leu Arg Gln His Gly Tyr Arg Val Ser Cys Glu Val
            115                 120                 125

Phe Glu Lys Phe Lys Asp Gly Lys Asp Gly Phe Lys Val Pro Asn Glu
        130                 135                 140

Asp Gly Ala Val Ala Val Leu Glu Phe Phe Glu Ala Thr His Leu Arg
145                 150                 155                 160

Val His Gly Glu Asp Val Leu Asp Asn Ala Phe Asp Phe Thr Arg Asn
                165                 170                 175
```

Tyr Leu Glu Ser Val Tyr Ala Thr Leu Asn Asp Pro Thr Ala Lys Gln
            180                 185                 190

Val His Asn Ala Leu Asn Glu Phe Ser Phe Arg Arg Gly Leu Pro Arg
            195                 200                 205

Val Glu Ala Arg Lys Tyr Ile Ser Ile Tyr Glu Gln Tyr Ala Ser His
            210                 215                 220

His Lys Gly Leu Leu Lys Leu Ala Lys Leu Asp Phe Asn Leu Val Gln
225                 230                 235                 240

Ala Leu His Arg Arg Glu Leu Ser Glu Asp Ser Arg Trp Trp Lys Thr
            245                 250                 255

Leu Gln Val Pro Thr Lys Leu Ser Phe Val Arg Asp Arg Leu Val Glu
            260                 265                 270

Ser Tyr Phe Trp Ala Ser Gly Ser Tyr Phe Glu Pro Asn Tyr Ser Val
            275                 280                 285

Ala Arg Met Ile Leu Ala Lys Gly Leu Ala Val Leu Ser Leu Met Asp
            290                 295                 300

Asp Val Tyr Asp Ala Tyr Gly Thr Phe Glu Glu Leu Gln Met Phe Thr
305                 310                 315                 320

Asp Ala Ile Glu Arg Trp Asp Ala Ser Cys Leu Asp Lys Leu Pro Asp
            325                 330                 335

Tyr Met Lys Ile Val Tyr Lys Ala Leu Leu Asp Val Phe Glu Glu Val
            340                 345                 350

Asp Glu Glu Leu Ile Lys Leu Gly Ala Pro Tyr Arg Ala Tyr Tyr Gly
            355                 360                 365

Lys Glu Ala Met Lys Tyr Ala Ala Arg Ala Tyr Met Glu Glu Ala Gln
            370                 375                 380

Trp Arg Glu Gln Lys His Lys Pro Thr Thr Lys Glu Tyr Met Lys Leu
385                 390                 395                 400

Ala Thr Lys Thr Cys Gly Tyr Ile Thr Leu Ile Ile Leu Ser Cys Leu
            405                 410                 415

Gly Val Glu Glu Gly Ile Val Thr Lys Glu Ala Phe Asp Trp Val Phe
            420                 425                 430

Ser Arg Pro Pro Phe Ile Glu Ala Thr Leu Ile Ile Ala Arg Leu Val
            435                 440                 445

Asn Asp Ile Thr Gly His Glu Phe Glu Lys Lys Arg Glu His Val Arg
450                 455                 460

Thr Ala Val Glu Cys Tyr Met Glu Glu His Lys Val Gly Lys Gln Glu
465                 470                 475                 480

Val Val Ser Glu Phe Tyr Asn Gln Met Glu Ser Ala Trp Lys Asp Ile
            485                 490                 495

Asn Glu Gly Phe Leu Arg Pro Val Glu Phe Pro Ile Pro Leu Leu Tyr
            500                 505                 510

Leu Ile Leu Asn Ser Val Arg Thr Leu Glu Val Ile Tyr Lys Glu Gly
            515                 520                 525

Asp Ser Tyr Thr His Val Gly Pro Ala Met Gln Asn Ile Ile Lys Gln
            530                 535                 540

Leu Tyr Leu His Pro Val Pro Tyr
545                 550

<210> SEQ ID NO 3
<211> LENGTH: 547
<212> TYPE: PRT
<213> ORGANISM: Aquilaria crassna

<400> SEQUENCE: 3

-continued

```
Met Ser Ser Ala Lys Leu Gly Ser Ala Ser Glu Asp Val Asn Arg Arg
1               5                   10                  15

Asp Ala Asn Tyr His Pro Thr Val Trp Gly Asp Phe Phe Leu Thr His
            20                  25                  30

Ser Ser Asn Phe Leu Glu Asn Asn Asp Ser Ile Leu Glu Lys His Glu
        35                  40                  45

Glu Leu Lys Gln Glu Val Arg Asn Leu Leu Val Val Glu Thr Ser Asp
    50                  55                  60

Leu Pro Ser Lys Ile Gln Leu Thr Asp Glu Ile Ile Arg Leu Gly Val
65                  70                  75                  80

Gly Tyr His Phe Glu Thr Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Pro Thr Lys Ile Glu Ser Leu Ser
    210                 215                 220

Leu Phe Ala Lys Ile Asp Phe Asn Met Leu Gln Ala Leu His Gln Arg
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415
```

```
Phe Glu Leu Lys Glu Thr Leu Asp Trp Ala Ser Thr Ile Pro Glu Met
                420                 425                 430

Val Glu Ala Ser Ser Leu Ile Ala Arg Tyr Ile Asp Asp Leu Gln Thr
            435                 440                 445

Tyr Lys Ala Glu Glu Arg Gly Glu Thr Val Ser Ala Val Arg Cys
        450                 455                 460

Tyr Met Arg Glu Phe Gly Val Ser Glu Glu Gln Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Ser Val Val Ile Pro Ser Leu Asn Phe
            500                 505                 510

Thr Arg Val Leu Glu Val Met Tyr Asp Lys Gly Asp Gly Tyr Ser Asp
        515                 520                 525

Ser Gln Gly Val Thr Lys Asp Arg Ile Ala Ala Leu Leu Arg His Ala
        530                 535                 540

Ile Glu Ile
545

<210> SEQ ID NO 4
<211> LENGTH: 547
<212> TYPE: PRT
<213> ORGANISM: Aquilaria crassna

<400> SEQUENCE: 4

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
                20                  25                  30

Ser Ser Asn Phe Leu Glu Asn Asn Asp Ser Ile Leu Glu Lys His Glu
            35                  40                  45

Glu Leu Lys Gln Glu Val Arg Asn Leu Leu Val Val Glu Thr Ser Asp
        50                  55                  60

Leu Pro Ser Lys Ile Gln Leu Thr Asp Glu Ile Ile Arg Leu Gly Val
65                  70                  75                  80

Gly Tyr His Phe Glu Thr Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Pro Ser Asp Val Phe
        115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Arg Leu Glu Ala
                165                 170                 175

Leu Leu Pro Lys Leu Ser Phe Pro Leu Ser Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Gln Thr Lys Ile Glu Ser Leu Ser
    210                 215                 220

Leu Phe Ala Lys Ile Asp Phe Asn Met Leu Gln Ala Leu His Gln Ser
225                 230                 235                 240
```

```
Glu Leu Arg Glu Ala Ser Arg Trp Trp Lys Glu Phe Asp Phe Pro Ser
            245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
            275                 280                 285

Asn Arg Ile Val Gly Ile Thr Ser Leu Ile Asp Asp Thr Tyr Asp Val
            290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Ile Gly Met Leu Gly Ile Phe Glu Asp Phe Lys Asp Asn Leu Ile
                340                 345                 350

Asn Ala Arg Gly Lys Asp Tyr Cys Ile Asp Tyr Ala Ile Glu Val Phe
            355                 360                 365

Lys Glu Ile Val Arg Ser Tyr Gln Arg Glu Ala Glu Tyr Phe His Thr
            370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
            435                 440                 445

Tyr Lys Ala Glu Glu Arg Gly Glu Thr Val Ser Ala Val Arg Cys
450                 455                 460

Tyr Met Arg Glu Phe Gly Val Ser Glu Gln Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Ser Val Val Ile Pro Ser Leu Asn Phe
                500                 505                 510

Thr Arg Val Leu Glu Val Met Tyr Asp Lys Gly Asp Gly Tyr Ser Asp
            515                 520                 525

Ser Gln Gly Val Thr Lys Asp Arg Ile Ala Ala Leu Leu Arg His Ala
530                 535                 540

Ile Glu Ile
545

<210> SEQ ID NO 5
<211> LENGTH: 547
<212> TYPE: PRT
<213> ORGANISM: Aquilaria crassna

<400> SEQUENCE: 5

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
            20                  25                  30

Ser Ser Asp Phe Leu Glu Asn Asn Asp Ser Ile Leu Glu Lys His Glu
            35                  40                  45

Glu Leu Lys Gln Glu Val Arg Asn Leu Leu Val Val Glu Thr Ser Asp
```

```
            50                  55                  60
Leu Pro Ser Lys Ile Gln Leu Thr Asp Asp Ile Ile Arg Leu Gly Val
 65                  70                  75                  80

Gly Tyr His Phe Glu Thr Glu Ile Lys Ala Gln Leu Glu Lys Leu His
                     85                  90                  95

Asp His Gln Leu His Leu Asn Phe Asp Leu Leu Thr Thr Ser Val Trp
                    100                 105                 110

Phe Arg Leu Leu Arg Gly His Gly Phe Ser Ile Ser Ser Asp Val Phe
                    115                 120                 125

Lys Arg Phe Lys Asn Thr Lys Gly Glu Phe Glu Thr Glu Asp Ala Arg
                    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                    165                 170                 175

Leu Leu Pro Glu Leu Ser Phe Pro Leu Asn Glu Cys Val Arg Asp Ala
                    180                 185                 190

Leu His Ile Pro Tyr His Arg Asn Val Gln Arg Leu Ala Ala Arg Gln
                    195                 200                 205

Tyr Ile Pro Gln Tyr Asp Ala Glu Pro Thr Lys Ile Glu Ser Leu Ser
                    210                 215                 220

Leu Phe Ala Lys Ile Asp Phe Asn Met Leu Gln Ala Leu His Gln Arg
225                 230                 235                 240

Glu Leu Arg Glu Ala Ser Arg Trp Trp Lys Glu Phe Asp Phe Pro Ser
                    245                 250                 255

Lys Leu Pro Tyr Ala Arg Asp Arg Ile Ala Glu Gly Tyr Tyr Trp Met
                    260                 265                 270

Met Gly Ala His Phe Glu Pro Lys Phe Ser Leu Ser Arg Lys Phe Leu
                    275                 280                 285

Asn Arg Ile Ile Gly Ile Thr Ser Leu Ile Asp Asp Thr Tyr Asp Val
                    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                    325                 330                 335

Tyr Ile Gly Met Leu Gly Ile Phe Glu Asp Phe Lys Asp Asn Leu Ile
                    340                 345                 350

Asn Ala Arg Gly Lys Asp Tyr Cys Ile Asp Tyr Ala Ile Glu Val Phe
                    355                 360                 365

Lys Glu Ile Val Arg Ser Tyr Gln Arg Glu Ala Glu Tyr Phe His Thr
                    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                    405                 410                 415

Phe Glu Leu Lys Glu Thr Leu Asp Trp Ala Ser Thr Ile Pro Glu Met
                    420                 425                 430

Val Lys Ala Ser Ser Leu Ile Ala Arg Tyr Ile Asp Asp Leu Gln Thr
                    435                 440                 445

Tyr Lys Ala Glu Glu Glu Arg Gly Glu Thr Val Ser Ala Val Arg Cys
                    450                 455                 460

Tyr Met Arg Glu Tyr Asp Val Ser Glu Glu Ala Cys Lys Lys Met
465                 470                 475                 480
```

Arg Glu Met Ile Glu Ile Glu Trp Lys Arg Leu Asn Lys Thr Thr Leu
            485                 490                 495

Glu Ala Asp Glu Val Ser Ser Val Val Ile Pro Ser Leu Asn Phe
            500                 505                 510

Thr Arg Val Leu Glu Val Met Tyr Asp Lys Gly Asp Gly Tyr Ser Asp
            515                 520                 525

Ser Gln Gly Val Thr Lys Asp Arg Ile Ala Ala Leu Leu Arg His Ala
            530                 535                 540

Ile Glu Ile
545

<210> SEQ ID NO 6
<211> LENGTH: 547
<212> TYPE: PRT
<213> ORGANISM: Aquilaria crassna

<400> SEQUENCE: 6

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
            20                  25                  30

Ser Ser Asn Phe Leu Glu Asn Asn Asp Ser Ile Leu Glu Lys His Glu
        35                  40                  45

Glu Leu Lys Gln Glu Val Arg Asn Leu Val Val Glu Thr Ser Asp
    50                  55                  60

Leu Pro Ser Lys Ile Gln Leu Thr Asp Glu Ile Ile Arg Leu Gly Val
65                  70                  75                  80

Gly Tyr His Phe Glu Thr Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
            115                 120                 125

Lys Arg Phe Lys Asn Thr Lys Gly Glu Phe Glu Thr Glu Asp Ala Trp
        130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
            195                 200                 205

Tyr Ile Pro Gln Tyr Asp Ala Glu Pro Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
            275                 280                 285

Asn Arg Ile Ile Gly Ile Thr Ser Leu Ile Asp Asp Thr Tyr Asp Val

```
            290                 295                 300
Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
        435                 440                 445

Tyr Lys Ala Glu Glu Glu Arg Gly Glu Thr Val Ser Ala Val Arg Cys
    450                 455                 460

Tyr Met Arg Glu Phe Gly Val Ser Glu Glu Gln Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
            500                 505                 510

Thr Arg Val Leu Glu Val Met Tyr Asp Lys Gly Asp Gly Tyr Ser Asp
        515                 520                 525

Ser Gln Gly Val Thr Lys Asp Arg Ile Ala Ala Leu Leu Arg His Ala
    530                 535                 540

Ile Glu Ile
545
```

<210> SEQ ID NO 7
<211> LENGTH: 547
<212> TYPE: PRT
<213> ORGANISM: Aquilaria crassna

<400> SEQUENCE: 7

```
Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
            20                  25                  30

Ser Ser Asn Phe Leu Glu Asn Asn Asp Ser Ile Leu Glu Lys His Glu
        35                  40                  45

Glu Leu Lys Gln Glu Val Arg Asn Leu Leu Val Glu Thr Ser Asp
    50                  55                  60

Leu Pro Ser Lys Ile Gln Leu Thr Asp Glu Ile Ile Arg Leu Gly Val
65                  70                  75                  80

Gly Tyr His Phe Glu Thr Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110
```

```
Phe Arg Leu Leu Arg Gly His Gly Phe Ser Ile Ser Ser Asp Val Phe
            115                 120                 125

Lys Arg Phe Lys Asn Thr Lys Gly Glu Phe Glu Thr Glu Asp Ala Arg
        130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Pro Thr Lys Ile Glu Ser Leu Ser
210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
        435                 440                 445

Tyr Lys Ala Glu Glu Glu Arg Gly Glu Thr Val Ser Ala Val Arg Cys
450                 455                 460

Tyr Met Arg Glu Phe Gly Val Ser Glu Glu Gln Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
            500                 505                 510

Thr Arg Val Leu Glu Val Met Tyr Asp Lys Gly Asp Gly Tyr Ser Asp
        515                 520                 525

Ser Gln Gly Val Thr Lys Asp Arg Ile Ala Ala Leu Leu Arg His Ala
```

```
            530             535             540

Ile Glu Ile
545

<210> SEQ ID NO 8
<211> LENGTH: 547
<212> TYPE: PRT
<213> ORGANISM: Aquilaria crassna

<400> SEQUENCE: 8

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
            20                  25                  30

Ser Ser Asn Phe Leu Glu Asn Asn Asp Ser Ile Leu Glu Lys His Glu
        35                  40                  45

Glu Leu Lys Gln Glu Val Arg Asn Leu Leu Val Val Glu Thr Ser Asp
    50                  55                  60

Leu Pro Ser Lys Ile Gln Leu Thr Asp Glu Ile Ile Arg Leu Gly Val
65                  70                  75                  80

Gly Tyr His Phe Glu Thr Glu Ile Lys Ala Gln Leu Gly Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Pro Thr Lys Ile Glu Ser Leu Ser
    210                 215                 220

Leu Phe Ala Lys Ile Asp Phe Asn Met Leu Gln Ala Leu His Gln Arg
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350
```

```
Asn Ala Arg Gly Lys Asp Tyr Cys Ile Asp Tyr Ala Ile Glu Val Phe
            355                 360                 365
Lys Glu Ile Val Arg Ser Tyr Gln Arg Glu Ala Glu Tyr Phe His Thr
    370                 375                 380
Gly Tyr Val Pro Ser Tyr Asp Glu Tyr Met Glu Asn Ser Ile Ile Ser
385                 390                 395                 400
Gly Gly Tyr Lys Met Phe Ile Ile Leu Met Leu Ile Gly Arg Gly Glu
                405                 410                 415
Phe Glu Leu Lys Glu Thr Leu Asp Trp Ala Ser Thr Ile Pro Glu Met
                420                 425                 430
Val Lys Ala Ser Ser Leu Ile Ala Arg Tyr Ile Asp Asp Leu Gln Thr
            435                 440                 445
Tyr Lys Ala Glu Glu Arg Gly Glu Thr Val Ser Ala Val Arg Cys
    450                 455                 460
Tyr Met Arg Glu Phe Gly Val Ser Glu Glu Gln Ala Cys Lys Lys Met
465                 470                 475                 480
Arg Glu Met Ile Glu Ile Glu Trp Lys Arg Leu Asn Lys Thr Thr Leu
                485                 490                 495
Glu Ala Asp Glu Ile Ser Ser Val Val Ile Pro Ser Leu Asn Phe
            500                 505                 510
Thr Arg Val Leu Glu Val Met Tyr Asp Lys Gly Asp Gly Tyr Ser Asp
    515                 520                 525
Ser Gln Gly Val Thr Lys Asp Arg Ile Ala Ala Leu Leu Arg His Ala
            530                 535                 540
Ile Glu Ile
545
```

<210> SEQ ID NO 9
<211> LENGTH: 547
<212> TYPE: PRT
<213> ORGANISM: Aquilaria crassna

<400> SEQUENCE: 9

```
Met Ser Ser Ala Lys Leu Gly Ser Ala Ser Glu Asp Val Ser Arg Arg
1               5                   10                  15
Asp Ala Asn Tyr His Pro Thr Val Trp Gly Asp Phe Phe Leu Thr His
                20                  25                  30
Ser Ser Asn Phe Leu Glu Asn Asn Asp Asn Ile Leu Glu Lys His Glu
            35                  40                  45
Glu Leu Lys Gln Glu Val Arg Asn Leu Leu Val Glu Thr Ser Asp
    50                  55                  60
Leu Pro Ser Lys Ile Gln Leu Thr Asp Glu Ile Ile Arg Leu Gly Val
65                  70                  75                  80
Gly Tyr His Phe Glu Met Glu Ile Lys Ala Gln Leu Glu Lys Leu His
                85                  90                  95
Asp His Gln Leu His Leu Asn Phe Asp Leu Leu Thr Thr Ser Val Trp
                100                 105                 110
Phe Arg Leu Leu Arg Gly His Gly Phe Ser Ile Ser Ser Asp Val Phe
            115                 120                 125
Lys Arg Phe Lys Asn Thr Lys Gly Glu Phe Glu Thr Glu Asp Ala Arg
    130                 135                 140
Thr Leu Trp Cys Leu Tyr Glu Ala Thr His Leu Arg Val Asp Gly Glu
145                 150                 155                 160
Asp Ile Leu Glu Glu Ala Ile Gln Phe Ser Arg Lys Arg Leu Glu Ala
                165                 170                 175
```

Leu Leu Pro Lys Leu Ser Phe Pro Leu Ser Glu Cys Val Arg Asp Ala
            180                 185                 190

Leu His Ile Pro Tyr His Arg Asn Val Gln Arg Leu Ala Ala Arg Gln
            195                 200                 205

Tyr Ile Pro Gln Tyr Asp Ala Glu Gln Thr Lys Ile Glu Ser Leu Ser
            210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
            275                 280                 285

Asn Arg Ile Ile Gly Ile Thr Ser Leu Ile Asp Asp Thr Tyr Asp Val
            290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Ile Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
            355                 360                 365

Lys Glu Ile Val Arg Ser Tyr Gln Arg Glu Ala Glu Tyr Phe His Thr
            370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
            435                 440                 445

Tyr Lys Ala Glu Glu Arg Gly Glu Thr Val Ser Ala Val Arg Cys
            450                 455                 460

Tyr Met Arg Glu Tyr Asp Val Ser Glu Glu Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Val Ser Ser Ser Val Val Ile Pro Ser Leu Asn Phe
            500                 505                 510

Thr Arg Val Leu Glu Val Met Tyr Asp Lys Gly Asp Gly Tyr Ser Asp
            515                 520                 525

Ser Gln Gly Val Thr Lys Asp Arg Ile Ala Ala Leu Leu Arg His Ala
            530                 535                 540

Ile Glu Ile
545

<210> SEQ ID NO 10
<211> LENGTH: 547
<212> TYPE: PRT
<213> ORGANISM: Aquilaria crassna -continued

<400> SEQUENCE: 10

```
Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
                20                  25                  30

Ser Ser Asn Phe Leu Glu Asn Asn Asp Ser Ile Leu Glu Lys His Glu
            35                  40                  45

Glu Leu Lys Gln Glu Val Arg Asn Leu Val Val Glu Thr Ile Asp
    50                  55                  60

Leu Pro Ser Lys Ile Gln Leu Thr Asp Glu Ile Ile Arg Leu Gly Val
65                  70                  75                  80

Gly Tyr His Phe Glu Met Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Leu Asn Val Gln Arg Leu Ala Ala Arg Gln
        195                 200                 205

Tyr Ile Pro Gln Tyr Asp Ala Glu Pro Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415
```

```
Phe Glu Leu Lys Glu Thr Leu Asp Trp Ala Ser Thr Ile Pro Glu Met
                420                 425                 430

Val Lys Ala Ser Ser Leu Ile Ala Arg Tyr Ile Asp Leu Gln Thr
            435                 440                 445

Tyr Lys Ala Glu Glu Arg Gly Glu Thr Val Ser Ala Val Arg Cys
    450                 455                 460

Tyr Met Arg Glu Tyr Gly Val Ser Glu Glu Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
                500                 505                 510

Thr Arg Val Leu Glu Val Met Tyr Asp Lys Gly Asp Gly Tyr Ser Asp
            515                 520                 525

Ser Gln Gly Val Thr Lys Asp Arg Ile Ala Ala Leu Leu Arg His Ala
            530                 535                 540

Ile Glu Ile
545

<210> SEQ ID NO 11
<211> LENGTH: 547
<212> TYPE: PRT
<213> ORGANISM: Aquilaria crassna

<400> SEQUENCE: 11

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
                20                  25                  30

Ser Ser Asn Phe Leu Glu Asn Asn Asp Asn Ile Leu Glu Lys His Glu
            35                  40                  45

Glu Leu Lys Gln Glu Val Arg Asn Leu Leu Val Val Glu Thr Ser Asp
        50                  55                  60

Leu Pro Ser Lys Ile Gln Leu Thr Asp Glu Ile Ile Arg Leu Gly Val
65                  70                  75                  80

Gly Tyr His Phe Glu Met Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Glu Asp Ala Arg
130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Arg Leu Glu Ala
                165                 170                 175

Leu Leu Pro Lys Leu Ser Phe Pro Leu Ser Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Gln Thr Lys Ile Glu Ser Leu Ser
    210                 215                 220

Leu Phe Ala Lys Ile Asp Phe Asn Met Leu Gln Ala Leu His Gln Ser
```

```
            225                 230                 235                 240
    Glu Leu Arg Glu Ala Ser Arg Trp Trp Lys Glu Phe Asp Phe Pro Ser
                    245                 250                 255

Lys Leu Pro Tyr Ala Arg Asp Arg Ile Ala Glu Gly Tyr Tyr Trp Met
                    260                 265                 270

Met Gly Ala His Phe Glu Pro Lys Phe Ser Leu Ser Arg Lys Phe Leu
                    275                 280                 285

Asn Arg Ile Ile Gly Ile Thr Ser Leu Ile Asp Asp Thr Tyr Asp Val
                    290                 295                 300

Tyr Gly Thr Leu Glu Glu Val Thr Leu Phe Thr Glu Ala Val Glu Arg
    305                 310                 315                 320

Trp Asp Ile Glu Ala Val Lys Asp Ile Pro Lys Tyr Met Gln Val Ile
                    325                 330                 335

Tyr Ile Gly Met Leu Gly Ile Phe Glu Asp Phe Lys Asp Asn Leu Ile
                    340                 345                 350

Asn Ala Arg Gly Lys Asp Tyr Cys Ile Asp Tyr Ala Ile Glu Val Phe
                    355                 360                 365

Lys Glu Ile Val Arg Ser Tyr Gln Arg Glu Ala Glu Tyr Phe His Thr
                    370                 375                 380

Gly Tyr Val Pro Ser Tyr Asp Glu Tyr Met Glu Asn Ser Ile Ile Ser
    385                 390                 395                 400

Gly Gly Tyr Lys Met Phe Ile Ile Leu Met Leu Ile Gly Arg Gly Glu
                    405                 410                 415

Phe Glu Leu Lys Gln Thr Leu Asp Trp Ala Ser Thr Ile Pro Glu Met
                    420                 425                 430

Val Lys Ala Ser Ser Leu Ile Ala Arg Tyr Ile Asp Asp Leu Gln Thr
                    435                 440                 445

Tyr Lys Ala Glu Glu Arg Gly Glu Thr Val Ser Ala Val Arg Cys
                    450                 455                 460

Tyr Met Arg Glu Tyr Asp Val Ser Glu Glu Ala Cys Lys Lys Met
    465                 470                 475                 480

Arg Glu Met Ile Glu Ile Glu Trp Lys Arg Leu Asn Lys Thr Thr Leu
                    485                 490                 495

Glu Ala Asp Glu Val Ser Ser Val Val Ile Pro Ser Leu Asn Phe
                    500                 505                 510

Thr Arg Val Leu Glu Val Met Tyr Asp Lys Gly Asp Gly Tyr Ser Asp
                    515                 520                 525

Ser Gln Gly Val Thr Lys Asp Arg Ile Ala Ala Leu Leu Arg His Ala
                    530                 535                 540

Ile Glu Ile
    545

<210> SEQ ID NO 12
<211> LENGTH: 547
<212> TYPE: PRT
<213> ORGANISM: Aquilaria spp.

<400> SEQUENCE: 12

Met Ser Ser Ala Lys Leu Gly Ser Ala Ser Glu Asp Val Ser Arg Arg
    1               5                   10                  15

Asp Ala Asn Tyr His Pro Thr Val Trp Gly Asp Phe Phe Leu Thr His
                    20                  25                  30

Ser Ser Asn Phe Leu Glu Asn Asn Asp Asn Ile Leu Glu Lys His Glu
                    35                  40                  45
```

-continued

Glu Leu Lys Gln Glu Val Arg Asn Leu Val Val Glu Thr Ser Asp
 50                  55                  60

Leu Pro Ser Lys Ile Gln Leu Thr Asp Lys Ile Ile Arg Leu Gly Val
 65                  70                  75                  80

Gly Tyr His Phe Glu Met Glu Ile Lys Ala Gln Leu Glu Lys Leu His
                 85                  90                  95

Asp His Gln Leu His Leu Asn Phe Asp Leu Leu Thr Thr Ser Val Trp
             100                 105                 110

Phe Arg Leu Leu Arg Gly His Gly Phe Ser Ile Ser Ser Asp Val Phe
             115                 120                 125

Lys Arg Phe Lys Asn Thr Lys Gly Glu Phe Glu Thr Glu Asp Ala Arg
         130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                 165                 170                 175

Leu Leu Pro Glu Leu Ser Phe Pro Leu Asn Glu Cys Val Arg Asp Ala
             180                 185                 190

Leu His Ile Pro Tyr His Arg Asn Val Gln Arg Leu Ala Ala Arg Gln
         195                 200                 205

Tyr Ile Pro Gln Tyr Asp Ala Glu Leu Thr Lys Ile Glu Ser Leu Ser
210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                 245                 250                 255

Lys Leu Pro Tyr Ala Arg Asp Arg Ile Ala Glu Gly Tyr Tyr Trp Met
             260                 265                 270

Met Gly Ala His Phe Glu Pro Lys Phe Ser Leu Ser Arg Lys Phe Leu
         275                 280                 285

Asn Arg Ile Ile Gly Ile Thr Ser Leu Ile Asp Asp Thr Tyr Asp Val
290                 295                 300

Tyr Gly Thr Leu Glu Glu Val Thr Leu Phe Thr Lys Ala Val Glu Arg
305                 310                 315                 320

Trp Asp Ile Glu Ala Val Gln Asp Ile Pro Lys Tyr Met Gln Val Ile
                 325                 330                 335

Tyr Thr Gly Met Leu Gly Ile Phe Glu Asp Phe Lys Asp Asn Leu Ile
             340                 345                 350

Asn Ala Arg Gly Lys Asp Tyr Cys Ile Asp Tyr Ala Ile Glu Val Phe
         355                 360                 365

Lys Glu Ile Val Arg Ser Tyr Gln Arg Glu Ala Glu Tyr Phe His Thr
370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                 405                 410                 415

Phe Glu Leu Lys Glu Thr Leu Asp Trp Ala Ser Thr Ile Pro Glu Met
             420                 425                 430

Val Lys Ala Ser Ser Leu Ile Ala Arg Tyr Ile Asp Asp Leu Gln Thr
         435                 440                 445

Tyr Lys Ala Glu Glu Lys Arg Gly Glu Thr Val Ser Ala Val Arg Cys
450                 455                 460

Tyr Met Arg Glu Tyr Gly Val Ser Glu Glu Glu Ala Cys Lys Lys Met

```
            465                 470                 475                 480
Arg Glu Met Ile Glu Ile Glu Trp Lys Lys Leu Asn Lys Thr Thr Leu
                        485                 490                 495

Glu Ala Asn Glu Ile Ser Ser Val Val Ile Pro Ser Leu Asn Phe
                500                 505                 510

Thr Arg Val Leu Glu Val Met Tyr Asp Lys Gly Asp Gly Tyr Ser Asp
                515                 520                 525

Ser Gln Gly Val Thr Lys Asp Arg Ile Ala Ala Leu Leu Arg His Ala
            530                 535                 540

Ile Glu Ile
545

<210> SEQ ID NO 13
<211> LENGTH: 547
<212> TYPE: PRT
<213> ORGANISM: Aquilaria spp.

<400> SEQUENCE: 13

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
                20                  25                  30

Ser Ser Asn Phe Leu Glu Asn Asn Asp Asn Ile Leu Glu Lys His Glu
            35                  40                  45

Glu Leu Lys Gln Glu Val Thr Asn Leu Leu Val Val Glu Thr Ser Asp
        50                  55                  60

Leu Pro Ser Lys Ile Gln Leu Thr Asp Glu Ile Ile Arg Leu Gly Val
65                  70                  75                  80

Gly Tyr His Phe Glu Met Glu Ile Lys Ala Gln Leu Gly Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Gly Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Leu Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285
```

```
Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
                340                 345                 350

Asn Ala Arg Gly Lys Asp Tyr Cys Ile Asp Tyr Ala Ile Glu Val Phe
                355                 360                 365

Lys Glu Ile Val Arg Ser Tyr Gln Arg Glu Ala Glu Tyr Phe His Thr
370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Ala Glu
                405                 410                 415

Phe Glu Leu Lys Glu Thr Leu Asp Trp Ala Ser Thr Ile Pro Glu Met
                420                 425                 430

Val Lys Ala Ser Ser Leu Ile Ala Arg Tyr Ile Asp Asp Leu Gln Thr
                435                 440                 445

Tyr Lys Ala Glu Glu Arg Gly Glu Thr Val Ser Ala Val Arg Cys
450                 455                 460

Tyr Met Arg Glu Tyr Gly Val Ser Glu Glu Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
                500                 505                 510

Thr Arg Val Leu Glu Val Met Tyr Asp Lys Gly Asp Gly Tyr Ser Asp
                515                 520                 525

Ser Gln Gly Val Thr Lys Gly Arg Ile Ala Ala Leu Leu Arg His Ala
530                 535                 540

Ile Glu Ile
545

<210> SEQ ID NO 14
<211> LENGTH: 547
<212> TYPE: PRT
<213> ORGANISM: Aquilaria spp.

<400> SEQUENCE: 14

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
                20                  25                  30

Ser Ser Asn Phe Leu Glu Asn Asn His Ser Ile Leu Glu Lys His Glu
                35                  40                  45

Glu Leu Lys Gln Glu Val Arg Asn Leu Val Val Glu Thr Ser Asp
50                  55                  60

Leu Pro Ser Lys Ile Gln Leu Thr Asp Lys Ile Ile Arg Leu Gly Val
65                  70                  75                  80

Gly Tyr His Phe Glu Met Glu Ile Lys Ala Gln Leu Glu Lys Leu His
                85                  90                  95

Asp His Gln Leu His Leu Asn Phe Asp Leu Leu Thr Thr Ser Val Trp
                100                 105                 110
```

-continued

Phe Arg Leu Leu Arg Gly His Gly Phe Ser Ile Ser Ser Asp Val Phe
            115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
            195                 200                 205

Tyr Ile Pro Gln Tyr Asp Ala Glu Leu Thr Lys Ile Glu Ser Leu Ser
        210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
            275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
            355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Ala Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
            435                 440                 445

Tyr Lys Ala Glu Glu Glu Arg Gly Glu Thr Val Ser Ala Val Arg Cys
    450                 455                 460

Tyr Met Arg Glu Tyr Gly Val Ser Glu Glu Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
            500                 505                 510

Thr Arg Val Leu Glu Val Met Tyr Asp Lys Gly Asp Gly Tyr Ser Asp
            515                 520                 525

Ser Gln Gly Val Thr Lys Asp Arg Ile Ala Ala Leu Arg His Ala
530                 535                 540

Ile Glu Ile
545

<210> SEQ ID NO 15
<211> LENGTH: 547
<212> TYPE: PRT
<213> ORGANISM: Aquilaria spp.

<400> SEQUENCE: 15

Met Ser Ser Ala Lys Leu Gly Ser Ala Pro Glu Asp Val Ser Arg Arg
1               5                   10                  15

Asp Ala Asn Tyr His Pro Thr Val Trp Gly Asp Phe Phe Leu Thr His
            20                  25                  30

Ser Ser Asn Phe Leu Glu Asn Asn His Ser Ile Leu Glu Lys His Glu
        35                  40                  45

Glu Leu Lys Gln Glu Val Arg Asn Leu Leu Val Val Glu Thr Ser Asp
    50                  55                  60

Leu Pro Ser Lys Ile Gln Leu Thr Asp Lys Ile Ile Arg Leu Gly Val
65                  70                  75                  80

Gly Tyr His Phe Glu Met Glu Ile Lys Ala Gln Leu Glu Lys Leu Gln
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
                165                 170                 175

Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Leu Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

```
Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Ala Glu
                405                 410                 415

Phe Glu Leu Lys Glu Thr Leu Asp Trp Ala Ser Thr Ile Pro Glu Met
                420                 425                 430

Val Lys Ala Ser Ser Leu Ile Ala Arg Tyr Ile Asp Asp Leu Gln Thr
                435                 440                 445

Tyr Lys Ala Glu Glu Glu Arg Gly Glu Thr Val Ser Ala Val Arg Cys
    450                 455                 460

Tyr Met Arg Glu Tyr Gly Val Ser Glu Glu Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Ser Val Val Ile Pro Ser Leu Asn Phe
                500                 505                 510

Thr Arg Val Leu Glu Val Met Tyr Asp Lys Gly Asp Gly Tyr Ser Asp
                515                 520                 525

Ser Gln Gly Val Thr Lys Asp Arg Ile Ala Thr Leu Leu Arg His Ala
                530                 535                 540

Ile Glu Ile
545

<210> SEQ ID NO 16
<211> LENGTH: 538
<212> TYPE: PRT
<213> ORGANISM: Aquilaria spp.

<400> SEQUENCE: 16

Met Ser Ser Ala Lys Leu Gly Ser Ala Ser Glu Asp Val Ser Arg Arg
1               5                   10                  15

Asp Ala Asp Tyr His Pro Thr Val Trp Gly Asp Phe Phe Leu Thr His
                20                  25                  30

Ser Ser Asn Phe Leu Glu Asn Asn His Ser Ile Leu Glu Lys His Glu
            35                  40                  45

Glu Leu Lys Gln Glu Val Arg Asn Leu Leu Val Glu Thr Ser Asp
    50                  55                  60

Leu Pro Ser Lys Ile Gln Leu Thr Asp Lys Ile Ile Arg Leu Gly Val
65                  70                  75                  80

Gly Tyr His Phe Glu Met Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Glu Thr Glu Asp Ala Arg
    130                 135                 140

Thr Ser Trp Cys Leu Tyr Glu Ala Thr His Leu Arg Val Asp Gly Glu
145                 150                 155                 160

Asp Ile Leu Glu Glu Ala Ile Gln Phe Ser Arg Lys Lys Leu Glu Ala
```

```
                165                 170                 175
Leu Leu Pro Glu Leu Ser Phe Pro Leu Asn Glu Cys Val Arg Asp Ala
            180                 185                 190

Leu His Ile Pro Tyr His Arg Asn Val Gln Arg Leu Ala Ala Arg Gln
        195                 200                 205

Tyr Ile Ser Gln Tyr Asp Ala Glu Leu Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Ala Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
        435                 440                 445

Tyr Lys Ala Glu Glu Arg Gly Glu Thr Val Ser Ala Val Arg Cys
    450                 455                 460

Tyr Met Arg Glu Tyr Gly Val Ser Glu Glu Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
            500                 505                 510

Thr Arg Val Leu Glu Val Met Tyr Asp Lys Gly Asp Gly Tyr Ser Asp
        515                 520                 525

Ser Gln Gly Val Thr Lys Asp Arg Ile Ala
    530                 535

<210> SEQ ID NO 17
<211> LENGTH: 547
<212> TYPE: PRT
<213> ORGANISM: Aquilaria spp.

<400> SEQUENCE: 17
```

```
Met Ser Ser Ala Lys Leu Gly Ser Thr Ser Glu Asp Val Ser Arg
1               5                   10                  15

Arg Asp Ala Asn Tyr His Pro Thr Val Trp Gly Asp Phe Phe Leu
                20                  25                  30

Thr His Ser Ser Asn Phe Leu Glu Asn Asn Asp Ser Ile Leu Glu
                35                  40                  45

Lys His Glu Glu Leu Lys Gln Glu Val Arg Asn Leu Leu Val Val
                50                  55                  60

Glu Thr Ser Asp Leu Pro Ser Lys Ile Gln Leu Thr Asp Glu Ile
65                  70                  75                  80

Ile Arg Leu Gly Val Gly Tyr His Phe Glu Thr Glu Ile Lys Ala
                85                  90                  95

Gln Leu Gly Lys Leu His Asp His Gln Leu His Leu Asn Phe Asp
                100                 105                 110

Leu Leu Thr Thr Ser Val Trp Phe Arg Leu Leu Arg Gly His Gly
                115                 120                 125

Phe Ser Ile Ser Ser Asp Val Phe Lys Arg Phe Lys Asn Thr Lys
130                 135                 140

Gly Glu Phe Lys Thr Glu Asp Ala Arg Thr Leu Trp Cys Leu Tyr
                145                 150                 155

Glu Ala Thr His Leu Arg Val Asp Gly Glu Asp Val Leu Glu Glu
160                 165                 170                 175

Ala Ile Gln Phe Ser Arg Lys Lys Leu Glu Ala Leu Leu Pro Glu
                180                 185                 190

Leu Ser Phe Pro Leu Ser Glu Cys Val Arg Asp Ala Leu His Ile
                195                 200                 205

Pro Tyr His Arg Asn Val Gln Arg Leu Ala Ala Arg Gln Tyr Ile
210                 215                 220

Pro Gln Tyr Asp Ala Glu Pro Thr Lys Ile Glu Ser Leu Ser Leu
                225                 230                 235                 240

Phe Ala Lys Ile Asp Phe Asn Met Leu Gln Ala Leu His Gln Ser
                245                 250                 255

Glu Leu Arg Glu Ala Ser Arg Trp Trp Lys Phe Asp Phe Pro Ser
                260                 265                 270

Lys Leu Pro Tyr Ala Arg Asp Ser Ile Ala Glu Gly Tyr Tyr Trp
275                 280                 285

Met Met Gly Ala His Phe Glu Pro Lys Phe Ser Leu Ser Arg Lys
                290                 295                 300

Phe Leu Asn Arg Ile Ile Gly Ile Thr Ser Leu Ile Asp Asp Thr
                305                 310                 315

Tyr Asp Val Tyr Gly Thr Leu Glu Glu Val Thr Leu Phe Thr Glu
320                 325                 330                 335

Ala Val Glu Arg Trp Asp Ile Glu Ala Val Lys Asp Ile Pro Lys
                340                 345                 350

Tyr Met Gln Val Ile Tyr Thr Gly Met Leu Gly Ile Phe Glu Asp
                355                 360                 365

Phe Lys Asp Asn Leu Ile Asn Ala Arg Gly Lys Asp Tyr Cys Ile
370                 375                 380

Asp Tyr Ala Ile Glu Val Phe Lys Glu Ile Val Arg Ser Tyr Gln
                385                 390                 395                 400

Arg Glu Ala Glu Tyr Phe His Thr Gly Tyr Val Pro Ser Tyr Asp
                405                 410                 415

Glu Tyr Met Glu Asn Ser Ile Ile Ser Gly Gly Tyr Lys Met Phe
420                 425                 430

Ile Ile Leu Met Leu Ile Gly Arg Gly Glu Phe Glu Leu Lys Glu
                435                 440                 445

Thr Leu Asp Trp Ala Ser Thr Ile Pro Glu Met
```

```
                420             425             430
Val Lys Ala Ser Ser Leu Ile Ala Arg Tyr Ile Asp Asp Leu Gln Thr
            435                 440                 445
Tyr Lys Ala Glu Glu Lys Arg Gly Glu Thr Val Ser Ala Val Arg Cys
        450                 455                 460
Tyr Met Arg Glu Tyr Gly Val Ser Glu Glu Ala Cys Lys Lys Met
465                 470                 475                 480
Lys Glu Met Ile Glu Ile Glu Trp Lys Arg Leu Asn Lys Thr Thr Leu
                485                 490                 495
Glu Ala Asp Glu Ile Ser Ser Val Val Ile Pro Ser Leu Asn Phe
            500                 505                 510
Thr Arg Val Leu Glu Val Met Tyr Asp Lys Gly Asp Gly Tyr Ser Asp
        515                 520                 525
Ser Gln Gly Val Thr Lys Asp Arg Ile Ala Ala Leu Leu Arg His Ala
        530                 535                 540
Ile Glu Ile
545

<210> SEQ ID NO 18
<211> LENGTH: 547
<212> TYPE: PRT
<213> ORGANISM: Aquilaria spp.

<400> SEQUENCE: 18

Met Ser Ser Ala Lys Leu Gly Ser Ala Ser Glu Asp Val Ser Arg Arg
1               5                   10                  15
Asp Ala Asn Tyr His Pro Thr Val Trp Gly Asp Phe Phe Leu Thr His
                20                  25                  30
Ser Ser Asn Phe Leu Glu Asn Asn Asp Ser Ile Leu Glu Lys His Glu
            35                  40                  45
Glu Leu Lys Gln Glu Val Arg Asn Leu Leu Val Val Glu Thr Ser Asp
        50                  55                  60
Leu Pro Ser Lys Ile Gln Leu Thr Asp Glu Ile Ile Arg Leu Gly Val
65                  70                  75                  80
Gly Tyr His Phe Glu Thr Glu Ile Lys Ala Gln Leu Glu Lys Leu His
                85                  90                  95
Asp His Gln Leu His Leu Asn Phe Asp Leu Leu Thr Thr Ser Val Trp
            100                 105                 110
Phe Arg Leu Leu Arg Gly His Gly Phe Ser Ile Ser Ser Asp Val Phe
        115                 120                 125
Lys Arg Phe Lys Asn Thr Lys Gly Glu Phe Lys Thr Glu Asp Ala Arg
        130                 135                 140
Thr Leu Trp Cys Leu Tyr Glu Ala Thr His Leu Arg Val Asp Gly Glu
145                 150                 155                 160
Asp Val Leu Glu Glu Ala Ile Gln Phe Ser Arg Lys Lys Leu Glu Ala
                165                 170                 175
Leu Leu Pro Glu Leu Ser Phe Pro Leu Ser Glu Cys Val Arg Asp Ala
            180                 185                 190
Leu His Ile Pro Tyr His Arg Asn Val Gln Arg Leu Ala Ala Arg Gln
        195                 200                 205
Tyr Ile Pro Gln Tyr Asp Ala Glu Pro Thr Lys Ile Glu Ser Leu Ser
        210                 215                 220
Leu Phe Ala Lys Ile Asp Phe Asn Met Leu Gln Ala Leu His Gln Ser
225                 230                 235                 240
```

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
        435                 440                 445

Tyr Lys Ala Glu Glu Lys Arg Gly Glu Thr Val Ser Ala Val Arg Cys
    450                 455                 460

Tyr Met Arg Glu Tyr Gly Val Ser Glu Glu Ala Cys Lys Lys Met
465                 470                 475                 480

Lys Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
            500                 505                 510

Thr Arg Val Leu Glu Val Met Tyr Asp Lys Gly Asp Gly Tyr Ser Asp
        515                 520                 525

Ser Gln Gly Val Thr Lys Asp Arg Ile Ala Ala Leu Leu Arg His Ala
    530                 535                 540

Ile Glu Ile
545

<210> SEQ ID NO 19
<211> LENGTH: 547
<212> TYPE: PRT
<213> ORGANISM: Aquilaria spp.

<400> SEQUENCE: 19

Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
            20                  25                  30

Ser Ser Asn Phe Leu Glu Asn Asn Asp Ser Ile Leu Glu Lys His Glu
        35                  40                  45

Glu Leu Lys Gln Glu Val Arg Asn Leu Leu Val Val Glu Thr Ser Asp
    50                  55                  60

```
Leu Pro Ser Lys Ile Gln Leu Thr Asp Glu Ile Ile Arg Leu Gly Val
 65                  70                  75                  80

Gly Tyr His Phe Glu Thr Glu Ile Lys Ala Gln Leu Glu Lys Leu His
                 85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Ser Ser Asp Val Phe
        115                 120                 125

Lys Arg Phe Lys Asn Thr Lys Gly Glu Phe Lys Thr Glu Asp Ala Arg
    130                 135                 140

Thr Leu Trp Cys Leu Tyr Glu Ala Thr His Leu Arg Val Asp Gly Glu
145                 150                 155                 160

Asp Val Leu Glu Glu Ala Ile Gln Phe Ser Arg Lys Lys Leu Glu Ala
                165                 170                 175

Leu Leu Pro Glu Leu Ser Phe Pro Leu Ser Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Pro Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Ile Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365

Lys Glu Ile Val Arg Ser Tyr Gln Arg Glu Ala Glu Tyr Phe His Thr
    370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
        435                 440                 445

Tyr Lys Ala Glu Glu Glu Arg Gly Glu Thr Val Ser Ala Val Arg Cys
    450                 455                 460

Tyr Met Arg Glu Tyr Gly Val Ser Glu Glu Glu Ala Cys Lys Lys Met
465                 470                 475                 480
```

```
Arg Glu Met Ile Glu Ile Glu Trp Lys Arg Leu Asn Lys Thr Thr Leu
                485                 490                 495
Glu Ala Asp Glu Ile Ser Ser Val Val Ile Pro Ser Leu Asn Phe
            500                 505                 510
Thr Arg Val Leu Glu Val Met Tyr Asp Lys Gly Asp Gly Tyr Ser Asp
        515                 520                 525
Ser Gln Gly Val Thr Lys Asp Arg Ile Ala Ala Leu Leu Arg His Ala
    530                 535                 540
Ile Glu Ile
545
```

<210> SEQ ID NO 20
<211> LENGTH: 547
<212> TYPE: PRT
<213> ORGANISM: Aquilaria spp.

<400> SEQUENCE: 20

```
Met Ser Ser Ala Lys Leu Gly Ser Ala Ser Glu Asp Val Ser Arg Arg
1               5                   10                  15
Asp Ala Asn Tyr His Pro Thr Val Trp Gly Asp Phe Phe Leu Thr His
            20                  25                  30
Ser Ser Asn Phe Leu Glu Asn Asn Asp Asn Ile Leu Glu Lys His Glu
        35                  40                  45
Glu Leu Lys Gln Glu Val Arg Asn Leu Val Val Glu Thr Ser Asp
    50                  55                  60
Leu Pro Ser Lys Ile Gln Leu Thr Asp Glu Ile Ile Arg Leu Gly Val
65                  70                  75                  80
Gly Tyr His Phe Glu Met Glu Ile Lys Ala Gln Leu Glu Lys Leu His
                85                  90                  95
Asp His Gln Leu His Leu Asn Phe Asp Leu Leu Thr Thr Ser Val Trp
            100                 105                 110
Phe Arg Leu Leu Arg Gly His Gly Phe Ser Ile Ser Ser Asp Val Phe
        115                 120                 125
Lys Arg Phe Lys Asn Thr Lys Gly Glu Phe Glu Thr Glu Asp Ala Arg
    130                 135                 140
Thr Leu Trp Cys Leu Tyr Glu Ala Thr His Leu Arg Val Asp Gly Glu
145                 150                 155                 160
Asp Ile Leu Glu Glu Ala Ile Gln Phe Ser Arg Lys Arg Leu Glu Ala
                165                 170                 175
Leu Leu Pro Lys Leu Ser Phe Pro Leu Ser Glu Cys Val Arg Asp Ala
            180                 185                 190
Leu His Ile Pro Tyr His Arg Asn Val Gln Arg Leu Ala Ala Arg Gln
        195                 200                 205
Tyr Ile Pro Gln Tyr Asp Ala Glu Gln Thr Lys Ile Glu Ser Leu Ser
    210                 215                 220
Leu Phe Ala Lys Ile Asp Phe Asn Met Leu Gln Ala Leu Arg Gln Ser
225                 230                 235                 240
Glu Leu Arg Glu Ala Ser Arg Trp Trp Lys Glu Phe Asp Phe Pro Ser
                245                 250                 255
Lys Leu Pro Tyr Ala Arg Asp Arg Ile Ala Glu Gly Tyr Tyr Trp Met
            260                 265                 270
Met Gly Ala His Phe Glu Pro Lys Phe Ser Leu Ser Arg Lys Phe Leu
        275                 280                 285
Asn Arg Ile Ile Gly Ile Thr Ser Leu Ile Asp Asp Thr Tyr Asp Val
    290                 295                 300
```

```
Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
            325                 330                 335

Tyr Thr Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
            355                 360                 365

Lys Glu Ile Val Arg Ser Tyr Gln Arg Glu Ala Glu Tyr Phe His Thr
            370                 375                 380

Gly Tyr Val Pro Ser Tyr Asp Glu Tyr Met Glu Asn Ser Ile Ile Ser
385                 390                 395                 400

Gly Gly Tyr Lys Met Phe Ile Ile Leu Met Leu Ile Gly Arg Gly Glu
                405                 410                 415

Phe Glu Leu Lys Glu Thr Leu Asp Trp Ala Ser Thr Ile Pro Glu Met
            420                 425                 430

Val Lys Ala Ser Ser Leu Ile Ala Arg Tyr Ile Asp Asp Leu Gln Thr
            435                 440                 445

Tyr Lys Ala Glu Glu Arg Gly Glu Thr Val Ser Ala Val Arg Cys
            450                 455                 460

Tyr Met Arg Glu Phe Gly Val Ser Glu Gln Ala Cys Lys Lys Met
465                 470                 475                 480

Arg Glu Met Ile Glu Ile Glu Trp Lys Arg Leu Asn Lys Thr Thr Leu
                485                 490                 495

Glu Ala Asp Glu Ile Ser Ser Val Val Ile Pro Ser Leu Asn Phe
            500                 505                 510

Thr Arg Val Leu Glu Val Met Tyr Asp Lys Gly Asp Gly Tyr Ser Asp
            515                 520                 525

Ser Gln Gly Val Thr Lys Asp Arg Ile Ala Ala Leu Leu Arg His Ala
            530                 535                 540

Ile Glu Ile
545

<210> SEQ ID NO 21
<211> LENGTH: 561
<212> TYPE: PRT
<213> ORGANISM: Vitis vinifera

<400> SEQUENCE: 21

Met Ser Val Pro Leu Ser Val Ser Val Thr Pro Ile Leu Ser Gln Arg
1               5                   10                  15

Ile Asp Pro Glu Val Ala Arg His Glu Ala Thr Tyr His Pro Asn Phe
            20                  25                  30

Trp Gly Asp Arg Phe Leu His Tyr Asn Pro Asp Asp Phe Cys Gly
            35                  40                  45

Thr His Ala Cys Lys Glu Gln Gln Ile Gln Glu Leu Lys Glu Glu Val
        50                  55                  60

Arg Lys Ser Leu Glu Ala Thr Ala Gly Asn Thr Ser Gln Leu Leu Lys
65                  70                  75                  80

Leu Ile Asp Ser Ile Gln Arg Leu Gly Leu Ala Tyr His Phe Glu Arg
                85                  90                  95

Glu Ile Glu Glu Ala Leu Lys Ala Met Tyr Gln Thr Tyr Thr Leu Val
            100                 105                 110

Asp Asp Asn Asp His Leu Thr Thr Val Ser Leu Leu Phe Arg Leu Leu
```

```
            115                 120                 125
Arg Gln Glu Gly Tyr His Ile Pro Ser Asp Val Phe Lys Lys Phe Met
    130                 135                 140

Asp Glu Gly Gly Asn Phe Lys Glu Ser Leu Val Gly Asp Leu Pro Gly
145                 150                 155                 160

Met Leu Ala Leu Tyr Glu Ala Ala His Leu Met Val His Gly Glu Asp
                165                 170                 175

Ile Leu Asp Glu Ala Leu Gly Phe Thr Thr Ala His Leu Gln Ser Met
                180                 185                 190

Ala Ile Asp Ser Asp Asn Pro Leu Thr Lys Gln Val Ile Arg Ala Leu
            195                 200                 205

Lys Arg Pro Ile Arg Lys Gly Leu Pro Arg Val Glu Ala Arg His Tyr
    210                 215                 220

Ile Thr Ile Tyr Gln Glu Asp Ser His Asn Glu Ser Leu Leu Lys
225                 230                 235                 240

Leu Ala Lys Leu Asp Tyr Asn Met Leu Gln Ser Leu His Arg Lys Glu
                245                 250                 255

Leu Ser Glu Ile Thr Lys Trp Trp Lys Gly Leu Asp Phe Ala Thr Lys
            260                 265                 270

Leu Pro Phe Ala Arg Asp Arg Ile Val Glu Gly Tyr Phe Trp Ile Leu
    275                 280                 285

Gly Val Tyr Phe Glu Pro Gln Tyr Tyr Leu Ala Arg Arg Ile Leu Met
290                 295                 300

Lys Val Phe Gly Val Leu Ser Ile Val Asp Asp Ile Tyr Asp Ala Tyr
305                 310                 315                 320

Gly Thr Phe Glu Glu Leu Lys Leu Phe Thr Glu Ala Ile Glu Arg Trp
                325                 330                 335

Asp Ala Ser Ser Ile Asp Gln Leu Pro Asp Tyr Met Lys Val Cys Tyr
            340                 345                 350

Gln Ala Leu Leu Asp Val Tyr Glu Glu Met Glu Glu Met Thr Lys
    355                 360                 365

Gln Gly Lys Leu Tyr Arg Val His Tyr Ala Gln Ala Ala Leu Lys Arg
    370                 375                 380

Gln Val Gln Ala Tyr Leu Leu Glu Ala Lys Trp Leu Lys Gln Glu Tyr
385                 390                 395                 400

Ile Pro Arg Met Asp Glu Tyr Met Ser Asn Ala Leu Val Ser Ser Ala
                405                 410                 415

Cys Ser Met Leu Thr Thr Thr Ser Phe Val Gly Met Gly Asp Ile Val
            420                 425                 430

Thr Lys Glu Ala Phe Asp Trp Val Phe Ser Asp Pro Lys Met Ile Arg
    435                 440                 445

Ala Ser Asn Val Ile Cys Arg Leu Met Asp Asp Ile Val Ser His Glu
        450                 455                 460

Phe Glu Gln Lys Arg Gly His Val Ala Ser Ala Val Glu Cys Tyr Met
465                 470                 475                 480

Lys Gln Tyr Gly Val Ser Lys Glu Glu Ala Tyr Asp Glu Phe Lys Lys
                485                 490                 495

Gln Val Glu Ser Ala Trp Lys Asp Asn Asn Glu Glu Phe Leu Gln Pro
            500                 505                 510

Thr Ala Val Pro Val Pro Leu Leu Thr Arg Val Leu Asn Phe Ser Arg
    515                 520                 525

Met Met Asp Val Leu Tyr Lys Asp Glu Asp Glu Tyr Thr Leu Val Gly
    530                 535                 540
```

```
Pro Leu Met Lys Asp Leu Val Ala Gly Met Leu Ile Asp Pro Val Pro
545                 550                 555                 560

Met
```

```
<210> SEQ ID NO 22
<211> LENGTH: 508
<212> TYPE: PRT
<213> ORGANISM: Vitis vinifera

<400> SEQUENCE: 22
```

```
Met Glu Leu Gln Phe Ser Phe Pro Ile Leu Cys Thr Phe Leu Leu
1               5                   10                  15

Phe Ile Tyr Leu Leu Lys Arg Leu Gly Lys Pro Ser Arg Thr Asn His
                20                  25                  30

Pro Ala Pro Lys Leu Pro Pro Gly Pro Trp Lys Leu Pro Ile Ile Gly
            35                  40                  45

Asn Met His Gln Leu Val Gly Ser Leu Pro His Arg Ser Leu Arg Ser
50                  55                  60

Leu Ala Lys Lys His Gly Pro Leu Met His Leu Gln Leu Gly Glu Val
65                  70                  75                  80

Ser Ala Ile Val Val Ser Ser Arg Glu Met Ala Lys Glu Val Met Lys
                85                  90                  95

Thr His Asp Ile Ile Phe Ser Gln Arg Pro Cys Ile Leu Ala Ala Ser
            100                 105                 110

Ile Val Ser Tyr Asp Cys Thr Asp Ile Ala Phe Ala Pro Tyr Gly Gly
        115                 120                 125

Tyr Trp Arg Gln Ile Arg Lys Ile Ser Val Leu Glu Leu Leu Ser Ala
130                 135                 140

Lys Arg Val Gln Ser Phe Arg Ser Val Arg Glu Glu Val Leu Asn
145                 150                 155                 160

Leu Val Arg Ser Val Ser Leu Gln Glu Gly Val Leu Ile Asn Leu Thr
                165                 170                 175

Lys Ser Ile Phe Ser Leu Thr Phe Ser Ile Ile Ser Arg Thr Ala Phe
            180                 185                 190

Gly Lys Lys Cys Lys Asp Gln Glu Ala Phe Ser Val Thr Leu Asp Lys
        195                 200                 205

Phe Ala Asp Ser Ala Gly Gly Phe Thr Ile Ala Asp Val Phe Pro Ser
210                 215                 220

Ile Lys Leu Leu His Val Val Ser Gly Met Arg Arg Lys Leu Glu Lys
225                 230                 235                 240

Val His Lys Lys Leu Asp Arg Ile Leu Gly Asn Ile Ile Asn Glu His
                245                 250                 255

Lys Ala Arg Ser Ala Ala Lys Glu Thr Cys Glu Ala Glu Val Asp Asp
            260                 265                 270

Asp Leu Val Asp Val Leu Leu Lys Val Gln Lys Gln Gly Asp Leu Glu
        275                 280                 285

Phe Pro Leu Thr Met Asp Asn Ile Lys Ala Val Leu Leu Asp Leu Phe
290                 295                 300

Val Ala Gly Thr Glu Thr Ser Ser Thr Ala Val Glu Trp Ala Met Ala
305                 310                 315                 320

Glu Met Leu Lys Asn Pro Arg Val Met Ala Lys Ala Gln Ala Glu Val
                325                 330                 335

Arg Asp Ile Phe Ser Arg Lys Gly Asn Ala Asp Glu Thr Val Val Arg
            340                 345                 350
```

Glu Leu Lys Phe Leu Lys Leu Val Ile Lys Glu Thr Leu Arg Leu His
            355                 360                 365

Pro Pro Val Pro Leu Leu Ile Pro Arg Glu Ser Arg Glu Arg Cys Ala
    370                 375                 380

Ile Asn Gly Tyr Glu Ile Pro Val Lys Thr Arg Val Ile Ile Asn Ala
385                 390                 395                 400

Trp Ala Ile Ala Arg Asp Pro Lys Tyr Trp Thr Asp Ala Glu Ser Phe
                405                 410                 415

Asn Pro Glu Arg Phe Leu Asp Ser Ser Ile Asp Tyr Gln Gly Thr Asn
            420                 425                 430

Phe Glu Tyr Ile Pro Phe Gly Ala Gly Arg Arg Met Cys Pro Gly Ile
            435                 440                 445

Leu Phe Gly Met Ala Asn Val Glu Leu Ala Leu Ala Gln Leu Leu Tyr
        450                 455                 460

His Phe Asp Trp Lys Leu Pro Asn Gly Ala Arg His Glu Glu Leu Asp
465                 470                 475                 480

Met Thr Glu Gly Phe Arg Thr Ser Thr Lys Arg Lys Gln Asp Leu Tyr
                485                 490                 495

Leu Ile Pro Ile Thr Tyr Arg Pro Leu Pro Val Glu
            500                 505

<210> SEQ ID NO 23
<211> LENGTH: 417
<212> TYPE: PRT
<213> ORGANISM: Bacillus subtilis

<400> SEQUENCE: 23

Met Asn Glu Gln Ile Pro His Asp Lys Ser Leu Asp Asn Ser Leu Thr
1               5                   10                  15

Leu Leu Lys Glu Gly Tyr Leu Phe Ile Lys Asn Arg Thr Glu Arg Tyr
            20                  25                  30

Asn Ser Asp Leu Phe Gln Ala Arg Leu Leu Gly Lys Asn Phe Ile Cys
        35                  40                  45

Met Thr Gly Ala Glu Ala Ala Lys Val Phe Tyr Asp Thr Asp Arg Phe
    50                  55                  60

Gln Arg Gln Asn Ala Leu Pro Lys Arg Val Gln Lys Ser Leu Phe Gly
65                  70                  75                  80

Val Asn Ala Ile Gln Gly Met Asp Gly Ser Ala His Ile His Arg Lys
                85                  90                  95

Met Leu Phe Leu Ser Leu Met Thr Pro Pro His Gln Lys Arg Leu Ala
            100                 105                 110

Glu Leu Met Thr Glu Glu Trp Lys Ala Ala Val Thr Arg Trp Glu Lys
        115                 120                 125

Ala Asp Glu Val Val Leu Phe Glu Glu Ala Lys Glu Ile Leu Cys Arg
    130                 135                 140

Val Ala Cys Tyr Trp Ala Gly Val Pro Leu Lys Glu Thr Glu Val Lys
145                 150                 155                 160

Glu Arg Ala Asp Asp Phe Ile Asp Met Val Asp Ala Phe Gly Ala Val
                165                 170                 175

Gly Pro Arg His Trp Lys Gly Arg Arg Ala Arg Pro Arg Ala Glu Glu
            180                 185                 190

Trp Ile Glu Val Met Ile Glu Asp Ala Arg Ala Gly Leu Leu Lys Thr
        195                 200                 205

Thr Ser Gly Thr Ala Leu His Glu Met Ala Phe His Thr Gln Glu Asp

```
                210                 215                 220
Gly Ser Gln Leu Asp Ser Arg Met Ala Ala Ile Glu Leu Ile Asn Val
225                 230                 235                 240

Leu Arg Pro Ile Val Ala Ile Ser Tyr Phe Leu Val Phe Ser Ala Leu
                245                 250                 255

Ala Leu His Glu His Pro Lys Tyr Lys Glu Trp Leu Arg Ser Gly Asn
            260                 265                 270

Ser Arg Glu Arg Glu Met Phe Val Gln Glu Val Arg Arg Tyr Tyr Pro
        275                 280                 285

Phe Gly Pro Phe Leu Gly Ala Leu Val Lys Lys Asp Phe Val Trp Asn
290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                325                 330                 335

Glu Arg Phe Ala Glu Arg Glu Asn Leu Phe Asp Met Ile Pro Gln
            340                 345                 350

Gly Gly Gly His Ala Glu Lys Gly His Arg Cys Pro Gly Glu Gly Ile
        355                 360                 365

Thr Ile Glu Val Met Lys Ala Ser Leu Asp Phe Leu Val His Gln Ile
    370                 375                 380

Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
                405                 410                 415

Ser

<210> SEQ ID NO 24
<211> LENGTH: 407
<212> TYPE: PRT
<213> ORGANISM: Bacillus subtilis

<400> SEQUENCE: 24

Met Gln Met Glu Lys Leu Met Phe His Pro His Gly Lys Glu Phe His
1               5                   10                  15

His Asn Pro Phe Ser Val Leu Gly Arg Phe Arg Glu Glu Pro Ile
            20                  25                  30

His Arg Phe Glu Leu Lys Arg Phe Gly Ala Thr Tyr Pro Ala Trp Leu
        35                  40                  45

Ile Thr Arg Tyr Asp Asp Cys Met Ala Phe Leu Lys Asp Asn Arg Ile
    50                  55                  60

Thr Arg Asp Val Lys Asn Val Met Asn Gln Glu Gln Ile Lys Met Leu
65                  70                  75                  80

Asn Val Ser Glu Asp Ile Asp Phe Val Ser Asp His Met Leu Ala Lys
                85                  90                  95

Asp Thr Pro Asp His Thr Arg Leu Arg Ser Leu Val His Gln Ala Phe
            100                 105                 110

Thr Pro Arg Thr Ile Glu Asn Leu Arg Gly Ser Ile Glu Gln Ile Ala
        115                 120                 125

Glu Gln Leu Leu Asp Glu Met Glu Lys Glu Asn Lys Ala Asp Ile Met
    130                 135                 140

Lys Ser Phe Ala Ser Pro Leu Pro Phe Val Ile Ser Glu Leu Met
145                 150                 155                 160

Gly Ile Pro Lys Glu Asp Arg Ser Gln Phe Gln Ile Trp Thr Asn Ala
```

```
                165                 170                 175
Met Val Asp Thr Ser Glu Gly Asn Arg Glu Leu Thr Asn Gln Ala Leu
            180                 185                 190

Arg Glu Phe Lys Asp Tyr Ile Ala Lys Leu Ile His Asp Arg Arg Ile
        195                 200                 205

Lys Pro Lys Asp Asp Leu Ile Ser Lys Leu Val His Ala Glu Glu Asn
    210                 215                 220

Gly Ser Lys Leu Ser Glu Lys Glu Leu Tyr Ser Met Leu Phe Leu Leu
225                 230                 235                 240

Val Val Ala Gly Leu Glu Thr Thr Val Asn Leu Leu Gly Ser Gly Thr
                245                 250                 255

Leu Ala Leu Leu Gln His Lys Lys Glu Cys Glu Lys Leu Lys Gln Gln
            260                 265                 270

Pro Glu Met Ile Ala Thr Ala Val Glu Glu Leu Leu Arg Tyr Thr Ser
        275                 280                 285

Pro Val Val Met Met Ala Asn Arg Trp Ala Ile Glu Asp Phe Thr Tyr
    290                 295                 300

Lys Gly His Ser Ile Lys Arg Gly Asp Met Ile Phe Ile Gly Ile Gly
305                 310                 315                 320

Ser Ala Asn Arg Asp Pro Asn Phe Phe Glu Asn Pro Glu Ile Leu Asn
                325                 330                 335

Ile Asn Arg Ser Pro Asn Arg His Ile Ser Phe Gly Phe Gly Ile His
            340                 345                 350

Phe Cys Leu Gly Ala Pro Leu Ala Arg Leu Glu Gly His Ile Ala Phe
        355                 360                 365

Lys Ala Leu Leu Lys Arg Phe Pro Asp Ile Glu Leu Ala Val Ala Pro
    370                 375                 380

Asp Asp Ile Gln Trp Arg Lys Asn Val Phe Leu Arg Gly Leu Glu Ser
385                 390                 395                 400

Leu Pro Val Ser Leu Ser Lys
                405

<210> SEQ ID NO 25
<211> LENGTH: 404
<212> TYPE: PRT
<213> ORGANISM: Bacillus cereus

<400> SEQUENCE: 25

Met Ala Ser Pro Glu Asn Val Ile Leu Val His Glu Ile Ser Lys Leu
1               5                   10                  15

Lys Thr Lys Glu Glu Leu Trp Asn Pro Tyr Glu Trp Tyr Gln Phe Met
            20                  25                  30

Arg Asp Asn His Pro Val His Tyr Asp Glu Glu Gln Asp Val Trp Asn
        35                  40                  45

Val Phe Leu Tyr Glu Asp Val Asn Arg Val Leu Ser Asp Tyr Arg Leu
    50                  55                  60

Phe Ser Ser Arg Arg Glu Arg Arg Gln Phe Ser Ile Pro Pro Leu Glu
65                  70                  75                  80

Thr Arg Ile Asn Ile Asn Ser Thr Asp Pro Pro Glu His Arg Asn Val
                85                  90                  95

Arg Ser Ile Val Ser Lys Ala Phe Thr Pro Arg Ser Leu Glu Gln Trp
            100                 105                 110

Lys Pro Arg Ile Gln Ala Ile Ala Asn Glu Leu Val Gln His Ile Gly
        115                 120                 125
```

-continued

```
Lys Tyr Ser Glu Val Asn Ile Val Glu Glu Phe Ala Ala Pro Leu Pro
    130                 135                 140

Val Thr Val Ile Ser Asp Leu Leu Gly Val Pro Thr Thr Asp Arg Lys
145                 150                 155                 160

Lys Ile Lys Ala Trp Ser Asp Ile Leu Phe Met Pro Tyr Ser Lys Glu
                165                 170                 175

Lys Phe Asn Asp Leu Asp Val Glu Lys Gly Ile Ala Leu Asn Glu Phe
            180                 185                 190

Lys Ala Tyr Leu Leu Pro Ile Val Gln Glu Lys Arg Tyr His Leu Thr
        195                 200                 205

Asp Asp Ile Ile Ser Asp Leu Ile Arg Ala Glu Tyr Glu Gly Glu Arg
    210                 215                 220

Leu Thr Asp Glu Glu Ile Val Thr Phe Ser Leu Gly Leu Leu Ala Ala
225                 230                 235                 240

Gly Asn Glu Thr Thr Thr Asn Leu Ile Ile Asn Ser Phe Tyr Cys Phe
                245                 250                 255

Leu Val Asp Ser Pro Gly Thr Tyr Lys Glu Leu Arg Glu Glu Pro Thr
            260                 265                 270

Leu Ile Ser Lys Ala Ile Glu Glu Val Leu Arg Tyr Arg Phe Pro Ile
        275                 280                 285

Thr Leu Ala Arg Arg Ile Thr Glu Asp Thr Asn Ile Phe Gly Pro Leu
    290                 295                 300

Met Lys Lys Asp Gln Met Val Val Ala Trp Val Ser Ala Ala Asn Leu
305                 310                 315                 320

Asp Glu Lys Lys Phe Ser Gln Ala Ser Lys Phe Asn Ile His Arg Ile
                325                 330                 335

Gly Asn Glu Lys His Leu Thr Phe Gly Lys Gly Pro His Phe Cys Leu
            340                 345                 350

Gly Ala Pro Leu Ala Arg Leu Glu Ala Glu Ile Ala Leu Thr Thr Phe
        355                 360                 365

Ile Asn Ala Phe Glu Lys Ile Ala Leu Ser Pro Ser Phe Asn Leu Glu
    370                 375                 380

Gln Cys Ile Leu Glu Asn Glu Gln Thr Leu Lys Phe Leu Pro Ile Cys
385                 390                 395                 400

Leu Lys Thr Gln

<210> SEQ ID NO 26
<211> LENGTH: 410
<212> TYPE: PRT
<213> ORGANISM: Bacillus cereus

<400> SEQUENCE: 26

Met Lys Lys Leu Thr Phe Asn Asp Leu Asn Ser Pro Glu Thr Met Arg
1               5                   10                  15

Asn Pro Ile Met Phe Tyr Lys Asn Leu Met Glu Gln Lys Glu Arg Phe
            20                  25                  30

Phe His Ile Asp Asp Phe Tyr Gly Met Gly Gly Ala Trp Val Val Phe
        35                  40                  45

His Tyr Asp Asp Val Val Ala Ile Leu Lys Asp Ser Arg Phe Ile Lys
    50                  55                  60

Asp Leu Arg Lys Phe Thr Pro Pro His Tyr Lys Gln Asn Pro Ile Glu
65                  70                  75                  80

Glu Asn Thr Ala Val Ser Lys Leu Phe Glu Trp Leu Met Asn Met Pro
                85                  90                  95
```

```
Asn Met Leu Thr Val Asp Pro Pro Asp His Thr Arg Leu Arg Arg Leu
            100                 105                 110

Val Ser Lys Ser Phe Thr Pro Arg Met Ile Glu Asp Leu Arg Pro Arg
        115                 120                 125

Ile Gln Gln Ile Ala Asp Glu Leu Leu Asp Val Val Gln Glu Gln Arg
    130                 135                 140

Lys Met Glu Ile Ile Ala Asp Phe Ala Tyr Pro Leu Pro Ile Ile Val
145                 150                 155                 160

Ile Ser Glu Met Leu Gly Ile Pro Ala Thr Asp Arg Asn Gln Phe Arg
                165                 170                 175

Ala Trp Thr Gln Glu Leu Met Lys Ala Ser Val Asp Pro Gly Gln Gly
            180                 185                 190

Thr Thr Val Thr Ala Thr Leu Glu Lys Phe Ile Asn Tyr Ile Glu Ile
        195                 200                 205

Leu Phe Asn Glu Lys His Leu Asn Pro Ser Asp Asp Leu Ile Ser Ala
    210                 215                 220

Leu Val Gln Ala Lys Glu Gln Glu Asp Lys Leu Ser Lys Asn Glu Leu
225                 230                 235                 240

Leu Ser Thr Ile Trp Leu Leu Ile Ile Ala Gly His Glu Thr Thr Val
                245                 250                 255

Asn Leu Ile Ser Asn Gly Val Leu Ala Leu Leu Gln His Pro Glu Gln
            260                 265                 270

Met Asn Leu Leu Arg Gln Asp Pro Ser Leu Leu Ala Ser Ala Val Asp
        275                 280                 285

Glu Leu Leu Arg Tyr Ala Gly Pro Ile Met Phe Ser Ser Arg Phe Ala
    290                 295                 300

Ser Glu Asp Val Thr Ile His Gly Asn Arg Ile Arg Lys Gly Glu Leu
305                 310                 315                 320

Val Leu Leu Ser Leu Thr Ala Ala Asn Ile Asp Pro Asn Ile Phe Pro
                325                 330                 335

Tyr Pro Glu Glu Leu Asn Ile Ser Arg Glu Gly Asn Asn His Leu Ala
            340                 345                 350

Phe Gly Ala Gly Ile His Gln Cys Leu Gly Ala Pro Leu Ala Arg Leu
        355                 360                 365

Glu Gly Gln Ile Ala Leu Asp Thr Leu Leu Lys Arg Leu Pro Asn Leu
    370                 375                 380

Arg Leu Ala Ile Glu Ala Asp Gln Leu Ile Tyr Asn His Ser Lys Ile
385                 390                 395                 400

Arg Ser Leu Ala Ser Leu Pro Val Ile Phe
                405                 410

<210> SEQ ID NO 27
<211> LENGTH: 711
<212> TYPE: PRT
<213> ORGANISM: Stevia rebaudiana

<400> SEQUENCE: 27

Met Ala Gln Ser Asp Ser Val Lys Val Ser Pro Phe Asp Leu Val Ser
1               5                   10                  15

Ala Ala Met Asn Gly Lys Ala Met Glu Lys Leu Asn Ala Ser Glu Ser
                20                  25                  30

Glu Asp Pro Thr Thr Leu Pro Ala Leu Lys Met Leu Val Glu Asn Arg
            35                  40                  45

Glu Leu Leu Thr Leu Phe Thr Thr Ser Phe Ala Val Leu Ile Gly Cys
        50                  55                  60
```

```
Leu Val Phe Leu Met Trp Arg Arg Ser Ser Lys Lys Leu Val Gln
 65                  70                  75                  80

Asp Pro Val Pro Gln Val Ile Val Val Lys Lys Glu Lys Glu Ser
                 85                  90                  95

Glu Val Asp Asp Gly Lys Lys Lys Val Ser Ile Phe Tyr Gly Thr Gln
             100                 105                 110

Thr Gly Thr Ala Glu Gly Phe Ala Lys Ala Leu Val Glu Glu Ala Lys
         115                 120                 125

Val Arg Tyr Glu Lys Thr Ser Phe Lys Val Ile Asp Leu Asp Asp Tyr
         130                 135                 140

Ala Ala Asp Asp Glu Tyr Glu Glu Lys Leu Lys Lys Glu Ser Leu
145                 150                 155                 160

Ala Phe Phe Phe Leu Ala Thr Tyr Gly Asp Gly Glu Pro Thr Asp Asn
                 165                 170                 175

Ala Ala Asn Phe Tyr Lys Trp Phe Thr Glu Gly Asp Asp Lys Gly Glu
             180                 185                 190

Trp Leu Lys Lys Leu Gln Tyr Gly Val Phe Gly Leu Gly Asn Arg Gln
             195                 200                 205

Tyr Glu His Phe Asn Lys Ile Ala Ile Val Val Asp Asp Lys Leu Thr
         210                 215                 220

Glu Met Gly Ala Lys Arg Leu Val Pro Val Gly Leu Gly Asp Asp Asp
225                 230                 235                 240

Gln Cys Ile Glu Asp Asp Phe Thr Ala Trp Lys Glu Leu Val Trp Pro
                 245                 250                 255

Glu Leu Asp Gln Leu Leu Arg Asp Glu Asp Thr Ser Val Thr Thr
             260                 265                 270

Pro Tyr Thr Ala Ala Val Leu Glu Tyr Arg Val Val Tyr His Asp Lys
         275                 280                 285

Pro Ala Asp Ser Tyr Ala Glu Asp Gln Thr His Thr Asn Gly His Val
         290                 295                 300

Val His Asp Ala Gln His Pro Ser Arg Ser Asn Val Ala Phe Lys Lys
305                 310                 315                 320

Glu Leu His Thr Ser Gln Ser Asp Arg Ser Cys Thr His Leu Glu Phe
                 325                 330                 335

Asp Ile Ser His Thr Gly Leu Ser Tyr Glu Thr Gly Asp His Val Gly
             340                 345                 350

Val Tyr Ser Glu Asn Leu Ser Glu Val Val Asp Glu Ala Leu Lys Leu
         355                 360                 365

Leu Gly Leu Ser Pro Asp Thr Tyr Phe Ser Val His Ala Asp Lys Glu
         370                 375                 380

Asp Gly Thr Pro Ile Gly Gly Ala Ser Leu Pro Pro Phe Pro Pro
385                 390                 395                 400

Cys Thr Leu Arg Asp Ala Leu Thr Arg Tyr Ala Asp Val Leu Ser Ser
                 405                 410                 415

Pro Lys Lys Val Ala Leu Leu Ala Leu Ala Ala His Ala Ser Asp Pro
             420                 425                 430

Ser Glu Ala Asp Arg Leu Lys Phe Leu Ala Ser Pro Ala Gly Lys Asp
             435                 440                 445

Glu Tyr Ala Gln Trp Ile Val Ala Asn Gln Arg Ser Leu Leu Glu Val
         450                 455                 460

Met Gln Ser Phe Pro Ser Ala Lys Pro Pro Leu Gly Val Phe Phe Ala
465                 470                 475                 480
```

```
Ala Val Ala Pro Arg Leu Gln Pro Arg Tyr Tyr Ser Ile Ser Ser Ser
            485                 490                 495

Pro Lys Met Ser Pro Asn Arg Ile His Val Thr Cys Ala Leu Val Tyr
            500                 505                 510

Glu Thr Thr Pro Ala Gly Arg Ile His Arg Gly Leu Cys Ser Thr Trp
            515                 520                 525

Met Lys Asn Ala Val Pro Leu Thr Glu Ser Pro Asp Cys Ser Gln Ala
            530                 535                 540

Ser Ile Phe Val Arg Thr Ser Asn Phe Arg Leu Pro Val Asp Pro Lys
545                 550                 555                 560

Val Pro Val Ile Met Ile Gly Pro Gly Thr Gly Leu Ala Pro Phe Arg
                565                 570                 575

Gly Phe Leu Gln Glu Arg Leu Ala Leu Lys Glu Ser Gly Thr Glu Leu
            580                 585                 590

Gly Ser Ser Ile Phe Phe Gly Cys Arg Asn Arg Lys Val Asp Phe
            595                 600                 605

Ile Tyr Glu Asp Glu Leu Asn Asn Phe Val Glu Thr Gly Ala Leu Ser
            610                 615                 620

Glu Leu Ile Val Ala Phe Ser Arg Glu Gly Thr Ala Lys Glu Tyr Val
625                 630                 635                 640

Gln His Lys Met Ser Gln Lys Ala Ser Asp Ile Trp Lys Leu Leu Ser
            645                 650                 655

Glu Gly Ala Tyr Leu Tyr Val Cys Gly Asp Ala Lys Gly Met Ala Lys
            660                 665                 670

Asp Val His Arg Thr Leu His Thr Ile Val Gln Glu Gln Gly Ser Leu
            675                 680                 685

Asp Ser Ser Lys Ala Glu Leu Tyr Val Lys Asn Leu Gln Met Ser Gly
            690                 695                 700

Arg Tyr Leu Arg Asp Val Trp
705                 710

<210> SEQ ID NO 28
<211> LENGTH: 693
<212> TYPE: PRT
<213> ORGANISM: Arabidopsis thaliana

<400> SEQUENCE: 28

Met Ala Thr Ser Ala Leu Tyr Ser Asp Leu Phe Lys Gln Leu Lys
1               5                   10                  15

Ser Ile Met Gly Thr Asp Ser Leu Ser Asp Val Val Leu Val Ile
                20                  25                  30

Ala Thr Thr Ser Leu Ala Leu Val Ala Gly Phe Val Val Leu Leu Trp
            35                  40                  45

Lys Lys Thr Thr Ala Asp Arg Ser Gly Glu Leu Lys Pro Leu Met Ile
50                  55                  60

Pro Lys Ser Leu Met Ala Lys Asp Glu Asp Asp Leu Asp Leu Gly
65                  70                  75                  80

Ser Gly Lys Thr Arg Val Ser Ile Phe Phe Gly Thr Gln Thr Gly Thr
                85                  90                  95

Ala Glu Gly Phe Ala Lys Ala Leu Ser Glu Glu Ile Lys Ala Arg Tyr
            100                 105                 110

Glu Lys Ala Ala Val Lys Val Ile Asp Leu Asp Asp Tyr Ala Ala Asp
        115                 120                 125

Asp Asp Gln Tyr Glu Glu Lys Leu Lys Lys Glu Thr Leu Ala Phe Phe
    130                 135                 140
```

-continued

```
Cys Val Ala Thr Tyr Gly Asp Gly Glu Pro Thr Asp Asn Ala Ala Arg
145                 150                 155                 160

Phe Tyr Lys Trp Phe Thr Glu Glu Asn Glu Arg Asp Ile Lys Leu Gln
                165                 170                 175

Gln Leu Ala Tyr Gly Val Phe Ala Leu Gly Asn Arg Gln Tyr Glu His
            180                 185                 190

Phe Asn Lys Ile Gly Ile Val Leu Asp Glu Glu Leu Cys Lys Lys Gly
        195                 200                 205

Ala Lys Arg Leu Ile Glu Val Gly Leu Gly Asp Asp Gln Ser Ile
210                 215                 220

Glu Asp Asp Phe Asn Ala Trp Lys Glu Ser Leu Trp Ser Glu Leu Asp
225                 230                 235                 240

Lys Leu Leu Lys Asp Glu Asp Asp Lys Ser Val Ala Thr Pro Tyr Thr
                245                 250                 255

Ala Val Ile Pro Glu Tyr Arg Val Val Thr His Asp Pro Arg Phe Thr
            260                 265                 270

Thr Gln Lys Ser Met Glu Ser Asn Val Ala Asn Gly Asn Thr Thr Ile
        275                 280                 285

Asp Ile His His Pro Cys Arg Val Asp Val Ala Val Gln Lys Glu Leu
290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335

Ala Glu Asn His Val Glu Ile Val Glu Ala Gly Lys Leu Leu Gly
            340                 345                 350

His Ser Leu Asp Leu Val Phe Ser Ile His Ala Asp Lys Glu Asp Gly
        355                 360                 365

Ser Pro Leu Glu Ser Ala Val Pro Pro Phe Pro Gly Pro Cys Thr
370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
                405                 410                 415

Ala Glu Lys Leu Lys His Leu Thr Ser Pro Asp Gly Lys Asp Glu Tyr
            420                 425                 430

Ser Gln Trp Ile Val Ala Ser Gln Arg Ser Leu Leu Glu Val Met Ala
        435                 440                 445

Ala Phe Pro Ser Ala Lys Pro Pro Leu Gly Val Phe Phe Ala Ala Ile
450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
                485                 490                 495

Thr Pro Thr Gly Arg Ile His Lys Gly Val Cys Ser Thr Trp Met Lys
            500                 505                 510

Asn Ala Val Pro Ala Glu Lys Ser His Glu Cys Ser Gly Ala Pro Ile
        515                 520                 525

Phe Ile Arg Ala Ser Asn Phe Lys Leu Pro Ser Asn Pro Ser Thr Pro
530                 535                 540

Ile Val Met Val Gly Pro Gly Thr Gly Leu Ala Pro Phe Arg Gly Phe
545                 550                 555                 560
```

Leu Gln Glu Arg Met Ala Leu Lys Glu Asp Gly Glu Leu Gly Ser
              565             570             575

Ser Leu Leu Phe Phe Gly Cys Arg Asn Arg Gln Met Asp Phe Ile Tyr
        580                 585                 590

Glu Asp Glu Leu Asn Asn Phe Val Asp Gln Gly Val Ile Ser Glu Leu
            595                 600                 605

Ile Met Ala Phe Ser Arg Glu Gly Ala Gln Lys Glu Tyr Val Gln His
    610                 615                 620

Lys Met Met Glu Lys Ala Ala Gln Val Trp Asp Leu Ile Lys Glu Glu
625                 630                 635                 640

Gly Tyr Leu Tyr Val Cys Gly Asp Ala Lys Gly Met Ala Arg Asp Val
                645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
        675                 680                 685

Leu Arg Asp Val Trp
        690

<210> SEQ ID NO 29
<211> LENGTH: 712
<212> TYPE: PRT
<213> ORGANISM: Arabidopsis thaliana

<400> SEQUENCE: 29

Met Ala Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
                20                  25                  30

Ala Ser Ala Tyr Glu Ser Val Ala Ala Glu Leu Ser Ser Met Leu Ile
            35                  40                  45

Glu Asn Arg Gln Phe Ala Met Ile Val Thr Thr Ser Ile Ala Val Leu
        50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
        115                 120                 125

Lys Ala Arg Tyr Glu Lys Thr Arg Phe Lys Ile Val Asp Leu Asp Asp
    130                 135                 140

Tyr Ala Ala Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
        195                 200                 205

Gln Tyr Glu His Phe Asn Lys Val Ala Lys Val Val Asp Asp Ile Leu
    210                 215                 220

Val Glu Gln Gly Ala Gln Arg Leu Val Gln Val Gly Leu Gly Asp Asp
225                 230                 235                 240

```
Asp Gln Cys Ile Glu Asp Asp Phe Thr Ala Trp Arg Glu Ala Leu Trp
            245                 250                 255

Pro Glu Leu Asp Thr Ile Leu Arg Glu Gly Asp Thr Ala Val Ala
        260                 265                 270

Thr Pro Tyr Thr Ala Ala Val Leu Glu Tyr Arg Val Ser Ile His Asp
        275                 280                 285

Ser Glu Asp Ala Lys Phe Asn Asp Ile Asn Met Ala Asn Gly Asn Gly
    290                 295                 300

Tyr Thr Val Phe Asp Ala Gln His Pro Tyr Lys Ala Asn Val Ala Val
305                 310                 315                 320

Lys Arg Glu Leu His Thr Pro Glu Ser Asp Arg Ser Cys Ile His Leu
                325                 330                 335

Glu Phe Asp Ile Ala Gly Ser Gly Leu Thr Tyr Glu Thr Gly Asp His
                340                 345                 350

Val Gly Val Leu Cys Asp Asn Leu Ser Glu Thr Val Asp Glu Ala Leu
            355                 360                 365

Arg Leu Leu Asp Met Ser Pro Asp Thr Tyr Phe Ser Leu His Ala Glu
    370                 375                 380

Lys Glu Asp Gly Thr Pro Ile Ser Ser Ser Leu Pro Pro Pro Phe Pro
385                 390                 395                 400

Pro Cys Asn Leu Arg Thr Ala Leu Thr Arg Tyr Ala Cys Leu Leu Ser
                405                 410                 415

Ser Pro Lys Lys Ser Ala Leu Val Ala Leu Ala Ala His Ala Ser Asp
                420                 425                 430

Pro Thr Glu Ala Glu Arg Leu Lys His Leu Ala Ser Pro Ala Gly Lys
            435                 440                 445

Asp Glu Tyr Ser Lys Trp Val Val Glu Ser Gln Arg Ser Leu Leu Glu
    450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
        515                 520                 525

Trp Met Lys Asn Ala Val Pro Tyr Glu Lys Ser Glu Asn Cys Ser Ser
530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
        610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655
```

```
Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
            675                 680                 685

Met Asp Ser Thr Lys Ala Glu Gly Phe Val Lys Asn Leu Gln Thr Ser
            690                 695                 700

Gly Arg Tyr Leu Arg Asp Val Trp
705                 710

<210> SEQ ID NO 30
<211> LENGTH: 713
<212> TYPE: PRT
<213> ORGANISM: Arabidopsis thaliana

<400> SEQUENCE: 30

Met Ala Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
            20                  25                  30

Ala Ser Ala Tyr Glu Ser Val Ala Ala Glu Leu Ser Ser Met Leu Ile
            35                  40                  45

Glu Asn Arg Gln Phe Ala Met Ile Val Thr Thr Ser Ile Ala Val Leu
50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
            115                 120                 125

Lys Ala Arg Tyr Glu Lys Thr Arg Phe Lys Ile Val Asp Leu Asp Asp
            130                 135                 140

Tyr Ala Ala Asp Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
            195                 200                 205

Gln Tyr Glu His Phe Asn Lys Val Ala Lys Val Val Asp Asp Ile Leu
            210                 215                 220

Val Glu Gln Gly Ala Gln Arg Leu Val Gln Val Gly Leu Gly Asp Asp
225                 230                 235                 240

Asp Gln Cys Ile Glu Asp Asp Phe Thr Ala Trp Arg Glu Ala Leu Trp
                245                 250                 255

Pro Glu Leu Asp Thr Ile Leu Arg Glu Glu Gly Asp Thr Ala Val Ala
            260                 265                 270

Thr Pro Tyr Thr Ala Ala Val Leu Glu Tyr Arg Val Ser Ile His Asp
            275                 280                 285

Ser Glu Asp Ala Lys Phe Asn Asp Ile Thr Leu Ala Asn Gly Asn Gly
            290                 295                 300

Tyr Thr Val Phe Asp Ala Gln His Pro Tyr Lys Ala Asn Val Ala Val
305                 310                 315                 320
```

```
Lys Arg Glu Leu His Thr Pro Glu Ser Asp Arg Ser Cys Ile His Leu
                325             330             335

Glu Phe Asp Ile Ala Gly Ser Gly Leu Thr Met Lys Leu Gly Asp His
            340             345             350

Val Gly Val Leu Cys Asp Asn Leu Ser Glu Thr Val Asp Glu Ala Leu
        355             360             365

Arg Leu Leu Asp Met Ser Pro Asp Thr Tyr Phe Ser Leu His Ala Glu
    370             375             380

Lys Glu Asp Gly Thr Pro Ile Ser Ser Ser Leu Pro Pro Phe Pro
385             390             395             400

Pro Cys Asn Leu Arg Thr Ala Leu Thr Arg Tyr Ala Cys Leu Leu Ser
                405             410             415

Ser Pro Lys Lys Ser Ala Leu Val Ala Leu Ala Ala His Ala Ser Asp
            420             425             430

Pro Thr Glu Ala Glu Arg Leu Lys His Leu Ala Ser Pro Ala Gly Lys
        435             440             445

Asp Glu Tyr Ser Lys Trp Val Val Glu Ser Gln Arg Ser Leu Leu Glu
    450             455             460

Val Met Ala Glu Phe Pro Ser Ala Lys Pro Pro Leu Gly Val Phe Phe
465             470             475             480

Ala Gly Val Ala Pro Arg Leu Gln Pro Arg Phe Tyr Ser Ile Ser Ser
                485             490             495

Ser Pro Lys Ile Ala Glu Thr Arg Ile His Val Thr Cys Ala Leu Val
            500             505             510

Tyr Glu Lys Met Pro Thr Gly Arg Ile His Lys Gly Val Cys Ser Thr
        515             520             525

Trp Met Lys Asn Ala Val Pro Tyr Glu Lys Ser Glu Lys Leu Phe Leu
    530             535             540

Gly Arg Pro Ile Phe Val Arg Gln Ser Asn Phe Lys Leu Pro Ser Asp
545             550             555             560

Ser Lys Val Pro Ile Ile Met Ile Gly Pro Gly Thr Gly Leu Ala Pro
                565             570             575

Phe Arg Gly Phe Leu Gln Glu Arg Leu Ala Leu Val Glu Ser Gly Val
            580             585             590

Glu Leu Gly Pro Ser Val Leu Phe Phe Gly Cys Arg Asn Arg Arg Met
        595             600             605

Asp Phe Ile Tyr Glu Glu Leu Gln Arg Phe Val Glu Ser Gly Ala
    610             615             620

Leu Ala Glu Leu Ser Val Ala Phe Ser Arg Glu Gly Pro Thr Lys Glu
625             630             635             640

Tyr Val Gln His Lys Met Met Asp Lys Ala Ser Asp Ile Trp Asn Met
                645             650             655

Ile Ser Gln Gly Ala Tyr Leu Tyr Val Cys Gly Asp Ala Lys Gly Met
            660             665             670

Ala Arg Asp Val His Arg Ser Leu His Thr Ile Ala Gln Glu Gln Gly
        675             680             685

Ser Met Asp Ser Thr Lys Ala Glu Gly Phe Val Lys Asn Leu Gln Thr
    690             695             700

Ser Gly Arg Tyr Leu Arg Asp Val Trp
705             710

<210> SEQ ID NO 31
```

<400> SEQUENCE: 31

000

<210> SEQ ID NO 32
<211> LENGTH: 708
<212> TYPE: PRT
<213> ORGANISM: Stevia rebaudiana

<400> SEQUENCE: 32

```
Met Ala Gln Ser Asn Ser Val Lys Ile Ser Pro Leu Asp Leu Val Thr
 1               5                  10                  15

Ala Leu Phe Ser Gly Lys Val Leu Asp Thr Ser Asn Ala Ser Glu Ser
            20                  25                  30

Gly Glu Ser Ala Met Leu Pro Thr Ile Ala Met Ile Met Glu Asn Arg
        35                  40                  45

Glu Leu Leu Met Ile Leu Thr Thr Ser Val Ala Val Leu Ile Gly Cys
    50                  55                  60

Val Val Val Leu Val Trp Arg Arg Ser Ser Thr Lys Lys Ser Ala Leu
65                  70                  75                  80

Glu Pro Pro Val Ile Val Pro Lys Arg Val Gln Glu Glu Glu Glu Val
                85                  90                  95

Asp Asp Gly Lys Lys Lys Val Thr Val Phe Phe Gly Thr Gln Thr Gly
            100                 105                 110

Thr Ala Glu Gly Phe Ala Lys Ala Leu Val Glu Glu Ala Lys Ala Arg
        115                 120                 125

Tyr Glu Lys Ala Val Phe Lys Val Ile Asp Leu Asp Asp Tyr Ala Ala
    130                 135                 140

Asp Asp Asp Glu Tyr Glu Glu Lys Leu Lys Lys Glu Ser Leu Ala Phe
145                 150                 155                 160

Phe Phe Leu Ala Thr Tyr Gly Asp Gly Glu Pro Thr Asp Asn Ala Ala
                165                 170                 175

Arg Phe Tyr Lys Trp Phe Thr Glu Gly Asp Ala Lys Gly Glu Trp Leu
            180                 185                 190

Asn Lys Leu Gln Tyr Gly Val Phe Gly Leu Gly Asn Arg Gln Tyr Glu
        195                 200                 205

His Phe Asn Lys Ile Ala Lys Val Val Asp Asp Gly Leu Val Glu Gln
    210                 215                 220

Gly Ala Lys Arg Leu Val Pro Val Gly Leu Gly Asp Asp Asp Gln Cys
225                 230                 235                 240

Ile Glu Asp Asp Phe Thr Ala Trp Lys Glu Leu Val Trp Pro Glu Leu
                245                 250                 255

Asp Gln Leu Leu Arg Asp Glu Asp Asp Thr Thr Val Ala Thr Pro Tyr
            260                 265                 270

Thr Ala Ala Val Ala Glu Tyr Arg Val Val Phe His Glu Lys Pro Asp
        275                 280                 285

Ala Leu Ser Glu Asp Tyr Ser Tyr Thr Asn Gly His Ala Val His Asp
    290                 295                 300

Ala Gln His Pro Cys Arg Ser Asn Val Ala Val Lys Lys Glu Leu His
305                 310                 315                 320

Ser Pro Glu Ser Asp Arg Ser Cys Thr His Leu Glu Phe Asp Ile Ser
                325                 330                 335

Asn Thr Gly Leu Ser Tyr Glu Thr Gly Asp His Val Gly Val Tyr Cys
            340                 345                 350

Glu Asn Leu Ser Glu Val Val Asn Asp Ala Glu Arg Leu Val Gly Leu
```

355                 360                 365
Pro Pro Asp Thr Tyr Phe Ser Ile His Thr Asp Ser Glu Asp Gly Ser
370                 375                 380

Pro Leu Gly Gly Ala Ser Leu Pro Pro Phe Pro Pro Cys Thr Leu
385                 390                 395                 400

Arg Lys Ala Leu Thr Cys Tyr Ala Asp Val Leu Ser Ser Pro Lys Lys
                405                 410                 415

Ser Ala Leu Leu Ala Leu Ala Ala His Ala Thr Asp Pro Ser Glu Ala
                420                 425                 430

Asp Arg Leu Lys Phe Leu Ala Ser Pro Ala Gly Lys Asp Glu Tyr Ser
                435                 440                 445

Gln Trp Ile Val Ala Ser Gln Arg Ser Leu Leu Glu Val Met Glu Ala
                450                 455                 460

Phe Pro Ser Ala Lys Pro Ser Leu Gly Val Phe Phe Ala Ser Val Ala
465                 470                 475                 480

Pro Arg Leu Gln Pro Arg Tyr Tyr Ser Ile Ser Ser Ser Pro Lys Met
                485                 490                 495

Ala Pro Asp Arg Ile His Val Thr Cys Ala Leu Val Tyr Glu Lys Thr
                500                 505                 510

Pro Ala Gly Arg Ile His Lys Gly Val Cys Ser Thr Trp Met Lys Asn
                515                 520                 525

Ala Val Pro Met Thr Glu Ser Gln Asp Cys Ser Trp Ala Pro Ile Tyr
                530                 535                 540

Val Arg Thr Ser Asn Phe Arg Leu Pro Ser Asp Pro Lys Val Pro Val
545                 550                 555                 560

Ile Met Ile Gly Pro Gly Thr Gly Leu Ala Pro Phe Arg Gly Phe Leu
                565                 570                 575

Gln Glu Arg Leu Ala Leu Lys Glu Ala Gly Thr Asp Leu Gly Leu Ser
                580                 585                 590

Ile Leu Phe Phe Gly Cys Arg Asn Arg Lys Val Asp Phe Ile Tyr Glu
                595                 600                 605

Asn Glu Leu Asn Asn Phe Val Glu Thr Gly Ala Leu Ser Glu Leu Ile
                610                 615                 620

Val Ala Phe Ser Arg Glu Gly Pro Thr Lys Glu Tyr Val Gln His Lys
625                 630                 635                 640

Met Ser Glu Lys Ala Ser Asp Ile Trp Asn Leu Leu Ser Glu Gly Ala
                645                 650                 655

Tyr Leu Tyr Val Cys Gly Asp Ala Lys Gly Met Ala Lys Asp Val His
                660                 665                 670

Arg Thr Leu His Thr Ile Val Gln Glu Gln Gly Ser Leu Asp Ser Ser
                675                 680                 685

Lys Ala Glu Leu Tyr Val Lys Asn Leu Gln Met Ser Gly Arg Tyr Leu
                690                 695                 700

Arg Asp Val Trp
705

<210> SEQ ID NO 33
<211> LENGTH: 705
<212> TYPE: PRT
<213> ORGANISM: Artemisia annua

<400> SEQUENCE: 33

Met Ala Gln Ser Thr Thr Ser Val Lys Leu Ser Pro Phe Asp Leu Met
1               5                   10                  15

Thr Ala Leu Leu Asn Gly Lys Val Ser Phe Asp Thr Ser Asn Thr Ser
                20                  25                  30

Asp Thr Asn Ile Pro Leu Ala Val Phe Met Glu Asn Arg Glu Leu Leu
            35                  40                  45

Met Ile Leu Thr Thr Ser Val Ala Val Leu Ile Gly Cys Val Val Val
        50                  55                  60

Leu Val Trp Arg Arg Ser Ser Ser Ala Ala Lys Lys Ala Ala Glu Ser
65                  70                  75                  80

Pro Val Ile Val Val Pro Lys Lys Val Thr Glu Asp Glu Val Asp Asp
                85                  90                  95

Gly Arg Lys Lys Val Thr Val Phe Phe Gly Thr Gln Thr Gly Thr Ala
            100                 105                 110

Glu Gly Phe Ala Lys Ala Leu Val Glu Glu Ala Lys Ala Arg Tyr Glu
        115                 120                 125

Lys Ala Val Phe Lys Val Ile Asp Leu Asp Asp Tyr Ala Ala Glu Asp
130                 135                 140

Asp Glu Tyr Glu Glu Lys Leu Lys Lys Glu Ser Leu Ala Phe Phe Phe
145                 150                 155                 160

Leu Ala Thr Tyr Gly Asp Gly Glu Pro Thr Asp Asn Ala Ala Arg Phe
                165                 170                 175

Tyr Lys Trp Phe Thr Glu Gly Glu Lys Gly Glu Trp Leu Asp Lys
            180                 185                 190

Leu Gln Tyr Ala Val Phe Gly Leu Gly Asn Arg Gln Tyr Glu His Phe
        195                 200                 205

Asn Lys Ile Ala Lys Val Val Asp Glu Lys Leu Val Glu Gln Gly Ala
210                 215                 220

Lys Arg Leu Val Pro Val Gly Met Gly Asp Asp Gln Cys Ile Glu
225                 230                 235                 240

Asp Asp Phe Thr Ala Trp Lys Glu Leu Val Trp Pro Glu Leu Asp Gln
                245                 250                 255

Leu Leu Arg Asp Glu Asp Asp Thr Ser Val Ala Thr Pro Tyr Thr Ala
            260                 265                 270

Ala Val Ala Glu Tyr Arg Val Val Phe His Asp Lys Pro Glu Thr Tyr
        275                 280                 285

Asp Gln Asp Gln Leu Thr Asn Gly His Ala Val His Asp Ala Gln His
290                 295                 300

Pro Cys Arg Ser Asn Val Ala Val Lys Lys Glu Leu His Ser Pro Leu
305                 310                 315                 320

Ser Asp Arg Ser Cys Thr His Leu Glu Phe Asp Ile Ser Asn Thr Gly
                325                 330                 335

Leu Ser Tyr Glu Thr Gly Asp His Val Gly Val Tyr Val Glu Asn Leu
            340                 345                 350

Ser Glu Val Val Asp Glu Ala Glu Lys Leu Ile Gly Leu Pro Pro His
        355                 360                 365

Thr Tyr Phe Ser Val His Ala Asp Asn Glu Asp Gly Thr Pro Leu Gly
370                 375                 380

Gly Ala Ser Leu Pro Pro Phe Pro Pro Cys Thr Leu Arg Lys Ala
385                 390                 395                 400

Leu Ala Ser Tyr Ala Asp Val Leu Ser Ser Pro Lys Lys Ser Ala Leu
                405                 410                 415

Leu Ala Leu Ala Ala His Ala Thr Asp Ser Thr Glu Ala Asp Arg Leu
            420                 425                 430

Lys Phe Leu Ala Ser Pro Ala Gly Lys Asp Glu Tyr Ala Gln Trp Ile

```
                435                 440                 445
Val Ala Ser His Arg Ser Leu Leu Glu Val Met Glu Ala Phe Pro Ser
    450                 455                 460

Ala Lys Pro Pro Leu Gly Val Phe Ala Ser Val Ala Pro Arg Leu
465                 470                 475                 480

Gln Pro Arg Tyr Tyr Ser Ile Ser Ser Pro Arg Phe Ala Pro Asn
                    485                 490                 495

Arg Ile His Val Thr Cys Ala Leu Val Tyr Glu Gln Thr Pro Ser Gly
                500                 505                 510

Arg Val His Lys Gly Val Cys Ser Thr Trp Met Lys Asn Ala Val Pro
                515                 520                 525

Met Thr Glu Ser Gln Asp Cys Ser Trp Ala Pro Ile Tyr Val Arg Thr
    530                 535                 540

Ser Asn Phe Arg Leu Pro Ser Asp Pro Lys Val Pro Val Ile Met Ile
545                 550                 555                 560

Gly Pro Gly Thr Gly Leu Ala Pro Phe Arg Gly Phe Leu Gln Glu Arg
                565                 570                 575

Leu Ala Gln Lys Glu Ala Gly Thr Glu Leu Gly Thr Ala Ile Leu Phe
                580                 585                 590

Phe Gly Cys Arg Asn Arg Lys Val Asp Phe Ile Tyr Glu Asp Glu Leu
                595                 600                 605

Asn Asn Phe Val Glu Thr Gly Ala Leu Ser Glu Leu Val Thr Ala Phe
610                 615                 620

Ser Arg Glu Gly Ala Thr Lys Glu Tyr Val Gln His Lys Met Thr Gln
625                 630                 635                 640

Lys Ala Ser Asp Ile Trp Asn Leu Leu Ser Glu Gly Ala Tyr Leu Tyr
                645                 650                 655

Val Cys Gly Asp Ala Lys Gly Met Ala Lys Asp Val His Arg Thr Leu
                660                 665                 670

His Thr Ile Val Gln Glu Gln Gly Ser Leu Asp Ser Ser Lys Ala Glu
                675                 680                 685

Leu Tyr Val Lys Asn Leu Gln Met Ala Gly Arg Tyr Leu Arg Asp Val
    690                 695                 700

Trp
705

<210> SEQ ID NO 34
<211> LENGTH: 706
<212> TYPE: PRT
<213> ORGANISM: Pelargonium graveolens

<400> SEQUENCE: 34

Met Ala Gln Ser Ser Gly Ser Met Ser Pro Phe Asp Phe Met Thr
1               5                   10                  15

Ala Ile Ile Lys Gly Lys Met Glu Pro Ser Asn Ala Ser Leu Gly Ala
            20                  25                  30

Ala Gly Glu Val Thr Ala Met Ile Leu Asp Asn Arg Glu Leu Val Met
        35                  40                  45

Ile Leu Thr Thr Ser Ile Ala Val Leu Ile Gly Cys Val Val Val Phe
    50                  55                  60

Ile Trp Arg Arg Ser Ser Ser Gln Thr Pro Thr Ala Val Gln Pro Leu
65              70                  75                  80

Lys Pro Leu Leu Ala Lys Glu Thr Glu Ser Glu Val Asp Asp Gly Lys
            85                  90                  95
```

```
Gln Lys Val Thr Ile Phe Phe Gly Thr Gln Thr Gly Thr Ala Glu Gly
                100                 105                 110

Phe Ala Lys Ala Leu Ala Asp Glu Ala Lys Ala Arg Tyr Asp Lys Val
            115                 120                 125

Thr Phe Lys Val Val Asp Leu Asp Asp Tyr Ala Ala Asp Asp Glu Glu
        130                 135                 140

Tyr Glu Glu Lys Leu Lys Lys Glu Thr Leu Ala Phe Phe Phe Leu Ala
145                 150                 155                 160

Thr Tyr Gly Asp Gly Glu Pro Thr Asp Asn Ala Ala Arg Phe Tyr Lys
                165                 170                 175

Trp Phe Leu Glu Gly Lys Glu Arg Gly Glu Trp Leu Gln Asn Leu Lys
            180                 185                 190

Phe Gly Val Phe Gly Leu Gly Asn Arg Gln Tyr Glu His Phe Asn Lys
        195                 200                 205

Ile Ala Ile Val Val Asp Glu Ile Leu Ala Glu Gln Gly Gly Lys Arg
    210                 215                 220

Leu Ile Ser Val Gly Leu Gly Asp Asp Gln Cys Ile Glu Asp Asp
225                 230                 235                 240

Phe Thr Ala Trp Arg Glu Ser Leu Trp Pro Glu Leu Asp Gln Leu Leu
                245                 250                 255

Arg Asp Glu Asp Asp Thr Thr Val Ser Thr Pro Tyr Thr Ala Ala Val
            260                 265                 270

Leu Glu Tyr Arg Val Val Phe His Asp Pro Ala Asp Ala Pro Thr Leu
        275                 280                 285

Glu Lys Ser Tyr Ser Asn Ala Asn Gly His Ser Val Val Asp Ala Gln
290                 295                 300

His Pro Leu Arg Ala Asn Val Ala Val Arg Arg Glu Leu His Thr Pro
305                 310                 315                 320

Ala Ser Asp Arg Ser Cys Thr His Leu Glu Phe Asp Ile Ser Gly Thr
                325                 330                 335

Gly Ile Ala Tyr Glu Thr Gly Asp His Val Gly Val Tyr Cys Glu Asn
            340                 345                 350

Leu Ala Glu Thr Val Glu Glu Ala Leu Glu Leu Leu Gly Leu Ser Pro
        355                 360                 365

Asp Thr Tyr Phe Ser Val His Ala Asp Lys Glu Asp Gly Thr Pro Leu
370                 375                 380

Ser Gly Ser Ser Leu Pro Pro Phe Pro Pro Cys Thr Leu Arg Thr
385                 390                 395                 400

Ala Leu Thr Leu His Ala Asp Leu Leu Ser Pro Lys Lys Ser Ala
                405                 410                 415

Leu Leu Ala Leu Ala Ala His Ala Ser Asp Pro Thr Glu Ala Asp Arg
            420                 425                 430

Leu Arg His Leu Ala Ser Pro Ala Gly Lys Asp Glu Tyr Ala Gln Trp
        435                 440                 445

Ile Val Ala Ser Gln Arg Ser Leu Leu Glu Val Met Ala Glu Phe Pro
450                 455                 460

Ser Ala Lys Pro Pro Leu Gly Val Phe Phe Ala Ser Val Ala Pro Arg
465                 470                 475                 480

Leu Gln Pro Arg Tyr Tyr Ser Ile Ser Ser Ser Pro Arg Ile Ala Pro
                485                 490                 495

Ser Arg Ile His Val Thr Cys Ala Leu Val Tyr Glu Lys Thr Pro Thr
            500                 505                 510

Gly Arg Val His Lys Gly Val Cys Ser Thr Trp Met Lys Asn Ser Val
```

```
                515                 520                 525
Pro Ser Glu Lys Ser Asp Glu Cys Ser Trp Ala Pro Ile Phe Val Arg
    530                 535                 540

Gln Ser Asn Phe Lys Leu Pro Ala Asp Ala Lys Val Pro Ile Ile Met
545                 550                 555                 560

Ile Gly Pro Gly Thr Gly Leu Ala Pro Phe Arg Gly Phe Leu Gln Glu
                565                 570                 575

Arg Leu Ala Leu Lys Glu Ala Gly Thr Glu Leu Gly Pro Ser Ile Leu
            580                 585                 590

Phe Phe Gly Cys Arg Asn Ser Lys Met Asp Tyr Ile Tyr Glu Asp Glu
        595                 600                 605

Leu Asp Asn Phe Val Gln Asn Gly Ala Leu Ser Glu Leu Val Leu Ala
    610                 615                 620

Phe Ser Arg Glu Gly Pro Thr Lys Glu Tyr Val Gln His Lys Met Met
625                 630                 635                 640

Glu Lys Ala Ser Asp Ile Trp Asn Leu Ile Ser Gln Gly Ala Tyr Leu
                645                 650                 655

Tyr Val Cys Gly Asp Ala Lys Gly Met Ala Arg Asp Val His Arg Thr
            660                 665                 670

Leu His Thr Ile Ala Gln Glu Gln Gly Ser Leu Asp Ser Ser Lys Ala
        675                 680                 685

Glu Ser Met Val Lys Asn Leu Gln Met Ser Gly Arg Tyr Leu Arg Asp
    690                 695                 700

Val Trp
705

<210> SEQ ID NO 35
<211> LENGTH: 282
<212> TYPE: PRT
<213> ORGANISM: Brachypodium distachyon

<400> SEQUENCE: 35

Met Ser Ala Ala Ala Val Ser Ser Ser Ser Pro Arg Leu Glu
1               5                   10                  15

Gly Lys Val Ala Leu Val Thr Gly Gly Ala Ser Gly Ile Gly Glu Ala
            20                  25                  30

Ile Val Arg Leu Phe Arg Gln His Gly Ala Lys Val Cys Ile Ala Asp
        35                  40                  45

Val Gln Asp Glu Ala Gly Gln Gln Val Arg Asp Ser Leu Gly Asp Asp
    50                  55                  60

Ala Gly Thr Asp Val Leu Phe Val His Cys Asp Val Thr Val Glu Glu
65                  70                  75                  80

Asp Val Ser Arg Ala Val Asp Ala Ala Glu Lys Phe Gly Thr Leu
                85                  90                  95

Asp Ile Met Val Asn Asn Ala Gly Ile Thr Gly Asp Lys Val Thr Asp
            100                 105                 110

Ile Arg Asn Leu Asp Phe Ala Glu Val Arg Lys Val Phe Asp Ile Asn
        115                 120                 125

Val His Gly Met Leu Leu Gly Met Lys His Ala Ala Arg Val Met Ile
    130                 135                 140

Pro Gly Lys Lys Gly Ser Ile Val Ser Leu Ala Ser Val Ala Ser Val
145                 150                 155                 160

Met Gly Gly Met Gly Pro His Ala Tyr Thr Ala Ser Lys His Ala Val
                165                 170                 175
```

-continued

Val Gly Leu Thr Lys Ser Val Ala Leu Glu Leu Gly Lys His Gly Ile
            180                 185                 190

Arg Val Asn Cys Val Ser Pro Tyr Ala Val Pro Thr Ala Leu Ser Met
            195                 200                 205

Pro His Leu Pro Gln Gly Glu His Lys Gly Asp Ala Val Arg Asp Phe
            210                 215                 220

Leu Ala Phe Val Gly Gly Glu Ala Asn Leu Lys Gly Val Asp Leu Leu
225                 230                 235                 240

Pro Lys Asp Val Ala Gln Ala Val Leu Tyr Leu Ala Ser Asp Glu Ala
            245                 250                 255

Arg Tyr Ile Ser Ala Leu Asn Leu Val Val Asp Gly Gly Phe Thr Ser
            260                 265                 270

Val Asn Pro Asn Leu Lys Ala Phe Glu Asp
            275                 280

<210> SEQ ID NO 36
<211> LENGTH: 280
<212> TYPE: PRT
<213> ORGANISM: Citrus sinensis

<400> SEQUENCE: 36

Met Ser Asn Ser Asn Ser Thr Asp Ser Ser Pro Ala Val Gln Arg Leu
1               5                   10                  15

Val Gly Arg Val Ala Leu Ile Thr Gly Gly Ala Thr Gly Ile Gly Glu
            20                  25                  30

Ser Thr Val Arg Leu Phe His Lys His Gly Ala Lys Val Cys Ile Ala
            35                  40                  45

Asp Val Gln Asp Asn Leu Gly Gln Gln Val Cys Gln Ser Leu Gly Gly
        50                  55                  60

Glu Pro Asp Thr Phe Phe Cys His Cys Asp Val Thr Lys Glu Glu Asp
65                  70                  75                  80

Val Cys Ser Ala Val Asp Leu Thr Val Glu Lys Phe Gly Thr Leu Asp
            85                  90                  95

Ile Met Val Asn Asn Ala Gly Ile Ser Gly Ala Pro Cys Pro Asp Ile
            100                 105                 110

Arg Glu Ala Asp Leu Ser Glu Phe Glu Lys Val Phe Asp Ile Asn Val
            115                 120                 125

Lys Gly Val Phe His Gly Met Lys His Ala Ala Arg Ile Met Ile Pro
            130                 135                 140

Gln Thr Lys Gly Thr Ile Ile Ser Ile Cys Ser Val Ala Gly Ala Ile
145                 150                 155                 160

Gly Gly Leu Gly Pro His Ala Tyr Thr Gly Ser Lys His Ala Val Leu
            165                 170                 175

Gly Leu Asn Lys Asn Val Ala Ala Glu Leu Gly Lys Tyr Gly Ile Arg
            180                 185                 190

Val Asn Cys Val Ser Pro Tyr Ala Val Ala Thr Gly Leu Ala Leu Ala
            195                 200                 205

His Leu Pro Glu Glu Glu Arg Thr Glu Asp Ala Met Val Gly Phe Arg
            210                 215                 220

Asn Phe Val Ala Arg Asn Ala Asn Met Gln Gly Thr Glu Leu Thr Ala
225                 230                 235                 240

Asn Asp Val Ala Asn Ala Val Leu Phe Leu Ala Ser Asp Glu Ala Arg
            245                 250                 255

Tyr Ile Ser Gly Thr Asn Leu Met Val Asp Gly Gly Phe Thr Ser Val
            260                 265                 270

```
Asn His Ser Leu Arg Val Phe Arg
        275                 280

<210> SEQ ID NO 37
<211> LENGTH: 280
<212> TYPE: PRT
<213> ORGANISM: Citrus sinensis

<400> SEQUENCE: 37

Met Ala Thr Pro Pro Ile Ser Ser Leu Ile Ser Gln Arg Leu Leu Gly
1               5                   10                  15

Lys Val Ala Leu Val Thr Gly Gly Ala Ser Gly Ile Gly Glu Gly Ile
            20                  25                  30

Val Arg Leu Phe His Arg His Gly Ala Lys Val Cys Phe Val Asp Val
        35                  40                  45

Gln Asp Glu Leu Gly Tyr Arg Leu Gln Glu Ser Leu Val Gly Asp Lys
    50                  55                  60

Asp Ser Asn Ile Phe Tyr Ser His Cys Asp Val Thr Val Glu Asp Asp
65                  70                  75                  80

Val Arg Arg Ala Val Asp Leu Thr Val Thr Lys Phe Gly Thr Leu Asp
                85                  90                  95

Ile Met Val Asn Asn Ala Gly Ile Ser Gly Thr Pro Ser Ser Asp Ile
            100                 105                 110

Arg Asn Val Asp Val Ser Glu Phe Glu Lys Val Phe Asp Ile Asn Val
        115                 120                 125

Lys Gly Val Phe Met Gly Met Lys Tyr Ala Ala Ser Val Met Ile Pro
    130                 135                 140

Arg Lys Gln Gly Ser Ile Ile Ser Leu Gly Ser Val Gly Ser Val Ile
145                 150                 155                 160

Gly Gly Ile Gly Pro His His Tyr Ile Ser Ser Lys His Ala Val Val
                165                 170                 175

Gly Leu Thr Arg Ser Ile Ala Ala Glu Leu Gly Gln His Gly Ile Arg
            180                 185                 190

Val Asn Cys Val Ser Pro Tyr Ala Val Pro Thr Asn Leu Ala Val Ala
        195                 200                 205

His Leu Pro Glu Asp Glu Arg Thr Glu Asp Met Phe Thr Gly Phe Arg
    210                 215                 220

Glu Phe Ala Lys Lys Asn Ala Asn Leu Gln Gly Val Glu Leu Thr Val
225                 230                 235                 240

Glu Asp Val Ala Asn Ala Val Leu Phe Leu Ala Ser Glu Asp Ala Arg
                245                 250                 255

Tyr Ile Ser Gly Asp Asn Leu Ile Val Asp Gly Gly Phe Thr Arg Val
            260                 265                 270

Asn His Ser Phe Arg Val Phe Arg
        275                 280

<210> SEQ ID NO 38
<211> LENGTH: 262
<212> TYPE: PRT
<213> ORGANISM: Citrus sinensis

<400> SEQUENCE: 38

Met Ser Lys Pro Arg Leu Gln Gly Lys Val Ala Ile Ile Met Gly Ala
1               5                   10                  15

Ala Ser Gly Ile Gly Glu Ala Thr Ala Lys Leu Phe Ala Glu His Gly
            20                  25                  30
```

```
Ala Phe Val Ile Ile Ala Asp Ile Gln Asp Glu Leu Gly Asn Gln Val
            35                  40                  45

Val Ser Ser Ile Gly Pro Glu Lys Ala Ser Tyr Arg His Cys Asp Val
 50                  55                  60

Arg Asp Glu Lys Gln Val Glu Thr Val Ala Tyr Ala Ile Glu Lys
 65                  70                  75                  80

Tyr Gly Ser Leu Asp Ile Met Tyr Ser Asn Ala Gly Val Ala Gly Pro
                85                  90                  95

Val Gly Thr Ile Leu Asp Leu Asp Met Ala Gln Phe Asp Arg Thr Ile
               100                 105                 110

Ala Thr Asn Leu Ala Gly Ser Val Met Ala Val Lys Tyr Ala Ala Arg
            115                 120                 125

Val Met Val Ala Asn Lys Ile Arg Gly Ser Ile Ile Cys Thr Thr Ser
            130                 135                 140

Thr Ala Ser Thr Val Gly Gly Ser Gly Pro His Ala Tyr Thr Ile Ser
145                 150                 155                 160

Lys His Gly Leu Leu Gly Leu Val Arg Ser Ala Ala Ser Glu Leu Gly
                165                 170                 175

Lys His Gly Ile Arg Val Asn Cys Val Ser Pro Phe Gly Val Ala Thr
                180                 185                 190

Pro Phe Ser Ala Gly Thr Ile Asn Asp Val Glu Gly Phe Val Cys Lys
            195                 200                 205

Val Ala Asn Leu Lys Gly Ile Val Leu Lys Ala Lys His Val Ala Glu
            210                 215                 220

Ala Ala Leu Phe Leu Ala Ser Asp Glu Ser Ala Tyr Val Ser Gly His
225                 230                 235                 240

Asp Leu Val Val Asp Gly Gly Phe Thr Ala Val Thr Asn Val Met Ser
                245                 250                 255

Met Leu Glu Gly His Gly
                260

<210> SEQ ID NO 39
<211> LENGTH: 263
<212> TYPE: PRT
<213> ORGANISM: Citrus sinensis

<400> SEQUENCE: 39

Met Ser Asn Pro Arg Met Glu Gly Lys Val Ala Leu Ile Thr Gly Ala
  1               5                  10                  15

Ala Ser Gly Ile Gly Glu Ala Ala Val Arg Leu Phe Ala Glu His Gly
                 20                  25                  30

Ala Phe Val Val Ala Ala Asp Val Gln Asp Glu Leu Gly His Gln Val
            35                  40                  45

Ala Ala Ser Val Gly Thr Asp Gln Val Cys Tyr His His Cys Asp Val
 50                  55                  60

Arg Asp Glu Lys Gln Val Glu Thr Val Arg Tyr Thr Leu Glu Lys
 65                  70                  75                  80

Tyr Gly Lys Leu Asp Val Leu Phe Ser Asn Ala Gly Ile Met Gly Pro
                85                  90                  95

Leu Thr Gly Ile Leu Glu Leu Asp Leu Thr Gly Phe Gly Asn Thr Met
               100                 105                 110

Ala Thr Asn Val Cys Gly Val Ala Ala Thr Ile Lys His Ala Ala Arg
            115                 120                 125

Ala Met Val Asp Lys Asn Ile Arg Gly Ser Ile Ile Cys Thr Thr Ser
```

```
            130                 135                 140
Val Ala Ser Ser Leu Gly Gly Thr Ala Pro His Ala Tyr Thr Thr Ser
145                 150                 155                 160

Lys His Ala Leu Val Gly Leu Val Arg Thr Ala Cys Ser Glu Leu Gly
                165                 170                 175

Ala Tyr Gly Ile Arg Val Asn Cys Ile Ser Pro Phe Gly Val Ala Thr
            180                 185                 190

Pro Leu Ser Cys Thr Ala Tyr Asn Leu Arg Pro Asp Glu Val Glu Ala
        195                 200                 205

Asn Ser Cys Ala Leu Ala Asn Leu Lys Gly Ile Val Leu Lys Ala Lys
    210                 215                 220

His Ile Ala Glu Ala Ala Leu Phe Leu Ala Ser Asp Glu Ser Ala Tyr
225                 230                 235                 240

Ile Ser Gly His Asn Leu Ala Val Asp Gly Gly Phe Thr Val Val Asn
                245                 250                 255

His Ser Ser Ser Ser Ala Thr
            260
```

<210> SEQ ID NO 40
<211> LENGTH: 278
<212> TYPE: PRT
<213> ORGANISM: Citrus sinensis

<400> SEQUENCE: 40

```
Met Thr Thr Ala Gly Ser Arg Asp Ser Pro Leu Val Ala Gln Arg Leu
1               5                   10                  15

Leu Gly Lys Val Ala Leu Val Thr Gly Gly Ala Thr Gly Ile Gly Glu
                20                  25                  30

Ser Ile Val Arg Leu Phe His Lys His Gly Ala Lys Val Cys Val Val
            35                  40                  45

Asp Ile Asn Asp Asp Leu Gly Gln His Leu Cys Gln Thr Leu Gly Pro
        50                  55                  60

Thr Thr Arg Phe Ile His Gly Asp Val Ala Ile Glu Asp Asp Val Ser
65                  70                  75                  80

Arg Ala Val Asp Phe Thr Val Ala Asn Phe Gly Thr Leu Asp Ile Met
                85                  90                  95

Val Asn Asn Ala Gly Met Gly Gly Pro Pro Cys Pro Asp Ile Arg Glu
            100                 105                 110

Phe Pro Ile Ser Thr Phe Glu Lys Val Phe Asp Ile Asn Thr Lys Gly
        115                 120                 125

Thr Phe Ile Gly Met Lys His Ala Ala Arg Val Met Ile Pro Ser Lys
130                 135                 140

Lys Gly Ser Ile Val Ser Ile Ser Ser Val Thr Ser Ala Ile Gly Gly
145                 150                 155                 160

Ala Gly Pro His Ala Tyr Thr Ala Ser Lys His Ala Val Leu Gly Leu
                165                 170                 175

Thr Lys Ser Val Ala Ala Glu Leu Gly Gln His Gly Ile Arg Val Asn
            180                 185                 190

Cys Val Ser Pro Tyr Ala Ile Leu Thr Asn Leu Ala Leu Ala His Leu
        195                 200                 205

His Glu Asp Glu Arg Thr Asp Asp Ala Arg Ala Gly Phe Arg Ala Phe
    210                 215                 220

Ile Gly Lys Asn Ala Asn Leu Gln Gly Val Asp Leu Val Glu Asp Asp
225                 230                 235                 240
```

```
Val Ala Asn Ala Val Leu Phe Leu Ala Ser Asp Asp Ala Arg Tyr Ile
                245                 250                 255

Ser Gly Asp Asn Leu Phe Val Asp Gly Gly Phe Thr Cys Thr Asn His
            260                 265                 270

Ser Leu Arg Val Phe Arg
        275
```

<210> SEQ ID NO 41
<211> LENGTH: 277
<212> TYPE: PRT
<213> ORGANISM: Rhodococcus erythropolis

<400> SEQUENCE: 41

```
Met Ala Arg Val Glu Gly Gln Val Ala Leu Ile Thr Gly Ala Ala Arg
1               5                   10                  15

Gly Gln Gly Arg Ser His Ala Ile Lys Leu Ala Glu Glu Gly Ala Asp
            20                  25                  30

Val Ile Leu Val Asp Val Pro Asn Asp Val Val Asp Ile Gly Tyr Pro
        35                  40                  45

Leu Gly Thr Ala Asp Glu Leu Asp Gln Thr Ala Lys Asp Val Glu Asn
    50                  55                  60

Leu Gly Arg Lys Ala Ile Val Ile His Ala Asp Val Arg Asp Leu Glu
65                  70                  75                  80

Ser Leu Thr Ala Glu Val Asp Arg Ala Val Ser Thr Leu Gly Arg Leu
                85                  90                  95

Asp Ile Val Ser Ala Asn Ala Gly Ile Ala Ser Val Pro Phe Leu Ser
            100                 105                 110

His Asp Ile Pro Asp Asn Thr Trp Arg Gln Met Ile Asp Ile Asn Leu
        115                 120                 125

Thr Gly Val Trp His Thr Ala Lys Val Ala Val Pro His Ile Leu Ala
    130                 135                 140

Gly Glu Arg Gly Gly Ser Ile Val Leu Thr Ser Ser Ala Ala Gly Leu
145                 150                 155                 160

Lys Gly Tyr Ala Gln Ile Ser His Tyr Ser Ala Ala Lys His Gly Val
                165                 170                 175

Val Gly Leu Met Arg Ser Leu Ala Leu Glu Leu Ala Pro His Arg Val
            180                 185                 190

Arg Val Asn Ser Leu His Pro Thr Gln Val Asn Thr Pro Met Ile Gln
        195                 200                 205

Asn Glu Gly Thr Tyr Arg Ile Phe Ser Pro Asp Leu Glu Asn Pro Thr
    210                 215                 220

Arg Glu Asp Phe Glu Ile Ala Ser Thr Thr Asn Ala Leu Pro Ile
225                 230                 235                 240

Pro Trp Val Glu Ser Val Asp Val Ser Asn Ala Leu Leu Phe Leu Val
                245                 250                 255

Ser Glu Asp Ala Arg Tyr Ile Thr Gly Ala Ala Ile Pro Val Asp Ala
            260                 265                 270

Gly Thr Thr Leu Lys
        275
```

<210> SEQ ID NO 42
<211> LENGTH: 279
<212> TYPE: PRT
<213> ORGANISM: Artificial Sequence
<220> FEATURE:
<223> OTHER INFORMATION: Synthetic Sequence

<400> SEQUENCE: 42

```
Met Ser Thr Ala Ser Ser Gly Asp Val Ser Leu Leu Ser Gln Arg Leu
1               5                   10                  15

Val Gly Lys Val Ala Leu Ile Thr Gly Gly Ala Thr Gly Ile Gly Glu
            20                  25                  30

Ser Ile Ala Arg Leu Phe Tyr Arg His Gly Ala Lys Val Cys Ile Val
            35                  40                  45

Asp Ile Gln Asp Asn Pro Gly Gln Asn Leu Cys Arg Glu Leu Gly Thr
        50                  55                  60

Asp Asp Ala Cys Phe Phe His Cys Asp Val Ser Ile Glu Ile Asp Val
65                  70                  75                  80

Ile Arg Ala Val Asp Phe Val Val Asn Arg Phe Gly Lys Leu Asp Ile
                85                  90                  95

Met Val Asn Asn Ala Gly Ile Ala Asp Pro Pro Cys Pro Asp Ile Arg
            100                 105                 110

Asn Thr Asp Leu Ser Ile Phe Glu Lys Val Phe Asp Val Asn Val Lys
        115                 120                 125

Gly Thr Phe Gln Cys Met Lys His Ala Ala Arg Val Met Val Pro Gln
    130                 135                 140

Lys Lys Gly Ser Ile Ile Ser Leu Thr Ser Val Ala Ser Val Ile Gly
145                 150                 155                 160

Gly Ala Gly Pro His Ala Tyr Thr Gly Ser Lys His Ala Val Leu Gly
                165                 170                 175

Leu Thr Lys Ser Val Ala Ala Glu Leu Gly Leu His Gly Ile Arg Val
            180                 185                 190

Asn Cys Val Ser Pro Tyr Ala Val Pro Thr Gly Met Pro Leu Ala His
        195                 200                 205

Leu Pro Glu Ser Glu Lys Thr Glu Asp Ala Met Met Gly Met Arg Ala
    210                 215                 220

Phe Val Gly Arg Asn Ala Asn Leu Gln Gly Ile Glu Leu Thr Val Asp
225                 230                 235                 240

Asp Val Ala Asn Ser Val Val Phe Leu Ala Ser Asp Glu Ala Arg Tyr
                245                 250                 255

Val Ser Gly Leu Asn Leu Met Leu Asp Gly Gly Phe Ser Cys Val Asn
            260                 265                 270

His Ser Leu Arg Val Phe Arg
        275
```

<210> SEQ ID NO 43
<211> LENGTH: 280
<212> TYPE: PRT
<213> ORGANISM: Vitis vinifera

<400> SEQUENCE: 43

```
Met Ala Ala Thr Ser Ile Asp Asn Ser Pro Leu Pro Ser Gln Arg Leu
1               5                   10                  15

Leu Gly Lys Val Ala Leu Val Thr Gly Gly Ala Thr Gly Ile Gly Glu
            20                  25                  30

Ser Ile Val Arg Leu Phe Leu Lys Gln Gly Ala Lys Val Cys Ile Val
            35                  40                  45

Asp Val Gln Asp Asp Leu Gly Gln Lys Leu Cys Asp Thr Leu Gly Gly
        50                  55                  60

Asp Pro Asn Val Ser Phe Phe His Cys Asp Val Thr Ile Glu Asp Asp
65                  70                  75                  80
```

Val Cys His Ala Val Asp Phe Thr Val Thr Lys Phe Gly Thr Leu Asp
            85                  90                  95

Ile Met Val Asn Asn Ala Gly Met Ala Gly Pro Pro Cys Ser Asp Ile
        100                 105                 110

Arg Asn Val Glu Val Ser Met Phe Glu Lys Val Phe Asp Val Asn Val
            115                 120                 125

Lys Gly Val Phe Leu Gly Met Lys His Ala Ala Arg Ile Met Ile Pro
        130                 135                 140

Leu Lys Lys Gly Thr Ile Ile Ser Leu Cys Ser Val Ser Ser Ala Ile
145                 150                 155                 160

Ala Gly Val Gly Pro His Ala Tyr Thr Gly Ser Lys Cys Ala Val Ala
            165                 170                 175

Gly Leu Thr Gln Ser Val Ala Ala Glu Met Gly Gly His Gly Ile Arg
        180                 185                 190

Val Asn Cys Ile Ser Pro Tyr Ala Ile Ala Thr Gly Leu Ala Leu Ala
            195                 200                 205

His Leu Pro Glu Asp Glu Arg Thr Glu Asp Ala Met Ala Gly Phe Arg
        210                 215                 220

Ala Phe Val Gly Lys Asn Ala Asn Leu Gln Gly Val Glu Leu Thr Val
225                 230                 235                 240

Asp Asp Val Ala His Ala Ala Val Phe Leu Ala Ser Asp Glu Ala Arg
            245                 250                 255

Tyr Ile Ser Gly Leu Asn Leu Met Leu Asp Gly Gly Phe Ser Cys Thr
        260                 265                 270

Asn His Ser Leu Arg Val Phe Arg
        275                 280

<210> SEQ ID NO 44
<211> LENGTH: 267
<212> TYPE: PRT
<213> ORGANISM: Zingiber zerumbet

<400> SEQUENCE: 44

Met Arg Leu Glu Gly Lys Val Ala Leu Val Thr Gly Gly Ala Ser Gly
1               5                   10                  15

Ile Gly Glu Ser Ile Ala Arg Leu Phe Ile Glu His Gly Ala Lys Ile
            20                  25                  30

Cys Ile Val Asp Val Gln Asp Glu Leu Gly Gln Gln Val Ser Gln Arg
        35                  40                  45

Leu Gly Gly Asp Pro His Ala Cys Tyr Phe His Cys Asp Val Thr Val
    50                  55                  60

Glu Asp Asp Val Arg Arg Ala Val Asp Phe Thr Ala Glu Lys Tyr Gly
65                  70                  75                  80

Thr Ile Asp Ile Met Val Asn Asn Ala Gly Ile Thr Gly Asp Lys Val
            85                  90                  95

Ile Asp Ile Arg Asp Ala Asp Phe Asn Glu Phe Lys Lys Val Phe Asp
        100                 105                 110

Ile Asn Val Asn Gly Val Phe Leu Gly Met Lys His Ala Ala Arg Ile
            115                 120                 125

Met Ile Pro Lys Met Lys Gly Ser Ile Val Ser Leu Ala Ser Val Ser
        130                 135                 140

Ser Val Ile Ala Gly Ala Gly Pro His Gly Tyr Thr Gly Ala Lys His
145                 150                 155                 160

Ala Val Val Gly Leu Thr Lys Ser Val Ala Ala Glu Leu Gly Arg His
            165                 170                 175

Gly Ile Arg Val Asn Cys Val Ser Pro Tyr Ala Val Pro Thr Arg Leu
                180                 185                 190

Ser Met Pro Tyr Leu Pro Glu Ser Glu Met Gln Glu Asp Ala Leu Arg
                195                 200                 205

Gly Phe Leu Thr Phe Val Arg Ser Asn Ala Asn Leu Lys Gly Val Asp
    210                 215                 220

Leu Met Pro Asn Asp Val Ala Glu Ala Val Leu Tyr Leu Ala Thr Glu
225                 230                 235                 240

Glu Ser Lys Tyr Val Ser Gly Leu Asn Leu Val Ile Asp Gly Phe
                245                 250                 255

Ser Ile Ala Asn His Thr Leu Gln Val Phe Glu
                260                 265

<210> SEQ ID NO 45
<211> LENGTH: 514
<212> TYPE: PRT
<213> ORGANISM: Nicotiana tomentosiformis

<400> SEQUENCE: 45

Met Asp Ala Ile Leu Asn Leu Gln Thr Val Pro Leu Gly Thr Ala Leu
1               5                   10                  15

Thr Ile Gly Gly Pro Ala Val Ala Leu Gly Gly Ile Ser Leu Trp Phe
                20                  25                  30

Leu Lys Glu Tyr Val Asn Asp Gln Lys Arg Lys Ser Ser Asn Phe Leu
            35                  40                  45

Pro Pro Leu Pro Glu Val Pro Gly Leu Pro Val Ile Gly Asn Leu Leu
    50                  55                  60

Gln Leu Thr Glu Lys Lys Pro His Lys Thr Phe Thr Asn Trp Ala Glu
65                  70                  75                  80

Thr Tyr Gly Pro Ile Tyr Ser Ile Lys Thr Gly Ala Asn Thr Ile Val
                85                  90                  95

Val Leu Asn Thr Asn Glu Leu Ala Lys Glu Ala Met Val Thr Arg Tyr
                100                 105                 110

Ser Ala Ile Ser Thr Arg Lys Leu Thr Asn Ala Leu Lys Ile Leu Thr
            115                 120                 125

Cys Asp Lys Ser Ile Val Ala Ile Ser Asp Tyr Asp Glu Phe His Lys
    130                 135                 140

Thr Val Lys Arg His Val Leu Thr Ser Val Leu Gly Pro Asn Ala Gln
145                 150                 155                 160

Lys Arg His Arg Ile His Arg Asp Thr Leu Ile Glu Asn Val Ser Lys
                165                 170                 175

Gln Leu His Asp Leu Val Arg Lys Tyr Pro Asn Glu Ala Val Asn Leu
                180                 185                 190

Arg Lys Ile Phe Gln Ser Glu Leu Phe Gly Leu Ala Leu Lys Gln Ala
            195                 200                 205

Leu Gly Lys Asp Ile Glu Ser Ile Tyr Val Gly Leu Asp Ala Thr
    210                 215                 220

Leu Pro Arg Glu Asp Val Leu Lys Thr Leu Val Leu Asp Ile Met Glu
225                 230                 235                 240

Gly Ala Ile Asp Val Asp Trp Arg Asp Phe Phe Pro Tyr Leu Lys Trp
                245                 250                 255

Val Pro Asn Lys Ser Phe Glu Asn Arg Ile Gln Arg Lys His Leu Arg
                260                 265                 270

Arg Glu Ala Val Met Lys Ala Leu Ile Met Glu Gln Arg Lys Arg Ile

```
            275                 280                 285
Asn Ser Gly Glu Lys Leu Asn Ser Tyr Ile Asp Tyr Leu Ser Ser Glu
        290                 295                 300

Ala Asn Thr Leu Thr Glu Lys Gln Ile Leu Met Leu Leu Trp Glu Ala
305                 310                 315                 320

Ile Ile Glu Thr Ser Asp Thr Thr Val Val Ser Thr Glu Trp Ala Met
                325                 330                 335

Tyr Glu Leu Ala Lys Asp Pro Lys Arg Gln Glu Gln Leu Phe Leu Glu
            340                 345                 350

Ile Gln Asn Val Cys Gly Ser Asn Lys Ile Thr Glu Glu Lys Leu Cys
        355                 360                 365

Gln Leu Pro Tyr Leu Cys Ala Val Phe His Glu Thr Leu Arg Lys His
    370                 375                 380

Ser Pro Val Pro Ile Val Pro Leu Arg Tyr Val His Glu Asp Thr Gln
385                 390                 395                 400

Leu Gly Gly Tyr His Ile Pro Lys Gly Ala Glu Ile Ala Ile Asn Ile
                405                 410                 415

Tyr Gly Cys Asn Arg Asp Lys Lys Val Trp Glu Ser Pro Glu Glu Trp
            420                 425                 430

Lys Pro Glu Arg Phe Leu Asp Gly Lys Tyr Asp Pro Val Glu Leu Gln
        435                 440                 445

Lys Thr Met Ala Phe Gly Gly Lys Arg Val Cys Ala Gly Ala Leu
    450                 455                 460

Gln Ala Met Thr Ile Thr Cys Thr Thr Ile Ala Arg Leu Ile Gln Glu
465                 470                 475                 480

Phe Glu Trp Ser Leu Lys Asp Gly Glu Glu Glu Asn Val Ala Thr Met
                485                 490                 495

Gly Leu Thr Thr His Lys Leu His Pro Met Gln Ala His Ile Lys Pro
            500                 505                 510

Arg Lys

<210> SEQ ID NO 46
<211> LENGTH: 512
<212> TYPE: PRT
<213> ORGANISM: Lactuca sativa

<400> SEQUENCE: 46

Met Asp Gly Val Ile Asp Met Gln Thr Ile Pro Leu Arg Thr Ala Ile
1               5                   10                  15

Ala Ile Gly Gly Thr Ala Val Ala Leu Val Val Ala Leu Tyr Phe Trp
                20                  25                  30

Phe Leu Arg Ser Tyr Ala Ser Pro Ser His Ser Asn His Leu Pro
            35                  40                  45

Pro Val Pro Glu Val Pro Gly Val Pro Val Leu Gly Asn Leu Leu Gln
        50                  55                  60

Leu Lys Glu Lys Lys Pro Tyr Met Thr Phe Thr Lys Trp Ala Glu Met
65                  70                  75                  80

Tyr Gly Pro Ile Tyr Ser Ile Arg Thr Gly Ala Thr Ser Met Val Val
                85                  90                  95

Val Ser Ser Asn Glu Ile Ala Lys Glu Val Val Thr Arg Phe Pro
            100                 105                 110

Ser Ile Ser Thr Arg Lys Leu Ser Tyr Ala Leu Lys Val Leu Thr Glu
        115                 120                 125

Asp Lys Ser Met Val Ala Met Ser Asp Tyr His Asp Tyr His Lys Thr
```

```
                    130                 135                 140
Val Lys Arg His Ile Leu Thr Ala Val Leu Gly Pro Asn Ala Gln Lys
145                 150                 155                 160

Lys Phe Arg Ala His Arg Asp Thr Met Met Glu Asn Val Ser Asn Glu
                    165                 170                 175

Leu His Ala Phe Phe Glu Lys Asn Pro Asn Gln Glu Val Asn Leu Arg
                180                 185                 190

Lys Ile Phe Gln Ser Gln Leu Phe Gly Leu Ala Met Lys Gln Ala Leu
                195                 200                 205

Gly Lys Asp Val Glu Ser Ile Tyr Val Lys Asp Leu Glu Thr Thr Met
            210                 215                 220

Lys Arg Glu Glu Ile Phe Glu Val Leu Val Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Ser Phe Glu Asn Ile Ile His Arg Met Tyr Thr Arg Arg
                260                 265                 270

Glu Ala Val Met Lys Ala Leu Ile Gln Glu His Lys Lys Arg Ile Ala
            275                 280                 285

Ser Gly Glu Asn Leu Asn Ser Tyr Ile Asp Tyr Leu Leu Ser Glu Ala
        290                 295                 300

Gln Thr Leu Thr Asp Lys Gln Leu Leu Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Asn Met Gln Asp Arg Leu Tyr Glu Glu Ile
                340                 345                 350

Gln Ser Val Cys Gly Ser Glu Lys Ile Thr Glu Glu Asn Leu Ser Gln
            355                 360                 365

Leu Pro Tyr Leu Tyr Ala Val Phe Gln Glu Thr Leu Arg Lys His Cys
        370                 375                 380

Pro Val Pro Ile Met Pro Leu Arg Tyr Val His Glu Asn Thr Val Leu
385                 390                 395                 400

Gly Gly Tyr His Val Pro Ala Gly Thr Glu Val Ala Ile Asn Ile Tyr
                405                 410                 415

Gly Cys Asn Met Asp Lys Lys Val Trp Glu Asn Pro Glu Glu Trp Asn
                420                 425                 430

Pro Glu Arg Phe Leu Ser Glu Lys Glu Ser Met Asp Leu Tyr Lys Thr
            435                 440                 445

Met Ala Phe Gly Gly Gly Lys Arg Val Cys Ala Gly Ser Leu Gln Ala
        450                 455                 460

Met Val Ile Ser Cys Ile Gly Ile Gly Arg Leu Val Gln Asp Phe Glu
465                 470                 475                 480

Trp Lys Leu Lys Asp Asp Ala Glu Glu Asp Val Asn Thr Leu Gly Leu
                485                 490                 495

Thr Thr Gln Lys Leu His Pro Leu Leu Ala Leu Ile Asn Pro Arg Lys
            500                 505                 510
```

<210> SEQ ID NO 47
<211> LENGTH: 513
<212> TYPE: PRT
<213> ORGANISM: Cynara cardunculus
<220> FEATURE:
<221> NAME/KEY: misc_feature
<222> LOCATION: (307)..(307)

```
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid

<400> SEQUENCE: 47
```

| | | | | | | | | | | | | | | |
|---|---|---|---|---|---|---|---|---|---|---|---|---|---|---|
| Met | Asp | Met | Gln | Ser | Ile | Pro | Ala | Ile | Ala | Ile | Gly | Ser | Thr | Ala | Val |
| 1 | | | | 5 | | | | | 10 | | | | | 15 | |
| Ala | Ile | Ala | Leu | Gly | Leu | Phe | Phe | Trp | Phe | Arg | Arg | His | Val | Pro |
| | | 20 | | | | | 25 | | | | | 30 | | |
| Asp | His | Ile | Asp | His | Pro | Asn | His | Leu | Pro | Ser | Val | Pro | Glu | Val | Pro |
| | | 35 | | | | | 40 | | | | 45 | | | | |
| Gly | Ile | Pro | Val | Leu | Gly | Asn | Leu | Leu | Gln | Leu | Lys | Glu | Lys | Lys | Pro |
| | 50 | | | | | 55 | | | | 60 | | | | | |
| Tyr | Met | Thr | Phe | Thr | Lys | Trp | Ala | Glu | Thr | Tyr | Gly | Pro | Ile | Tyr | Ser |
| 65 | | | | | 70 | | | | | 75 | | | | | 80 |
| Ile | Arg | Thr | Gly | Ala | Ile | Ser | Met | Val | Val | Ser | Ser | Asn | Ala | Ile |
| | | | | 85 | | | | | 90 | | | | | 95 |
| Ala | Lys | Glu | Ala | Leu | Val | Thr | Arg | Phe | Pro | Ser | Ile | Ser | Thr | Arg | Lys |
| | | | 100 | | | | | 105 | | | | | 110 | | |
| Leu | Ser | Lys | Ala | Leu | Glu | Val | Leu | Thr | Ala | Asp | Lys | Thr | Met | Val | Ala |
| | | 115 | | | | | 120 | | | | | 125 | | | |
| Met | Ser | Asp | Tyr | Asn | Asp | Tyr | His | Lys | Thr | Val | Lys | Arg | His | Ile | Leu |
| 130 | | | | | 135 | | | | | 140 | | | | | |
| Thr | Ala | Val | Leu | Gly | Pro | Asn | Ala | Gln | Lys | Lys | His | Arg | Val | His | Arg |
| 145 | | | | | 150 | | | | | 155 | | | | | 160 |
| Asp | Ile | Met | Met | Gln | Asn | Leu | Ser | Asn | Gln | Leu | His | Thr | Phe | Val | Gln |
| | | | | 165 | | | | | 170 | | | | | 175 | |
| Asn | Ser | Pro | Gln | Glu | Glu | Val | Asn | Leu | Arg | Lys | Val | Phe | Gln | Ser | Glu |
| | | | 180 | | | | | 185 | | | | | 190 | | |
| Leu | Phe | Gly | Leu | Ala | Met | Arg | Gln | Thr | Met | Gly | Lys | Asp | Val | Glu | Ser |
| | | 195 | | | | | 200 | | | | | 205 | | | |
| Ile | Tyr | Val | Glu | Asp | Leu | Gly | Thr | Thr | Met | Asn | Arg | Asp | Glu | Ile | Phe |
| | 210 | | | | | 215 | | | | | 220 | | | | |
| Gln | Val | Leu | Val | Val | Asp | Pro | Leu | Met | Gly | Ala | Ile | Glu | Val | Asp | Trp |
| 225 | | | | | 230 | | | | | 235 | | | | | 240 |
| Arg | Asp | Phe | Phe | Pro | Tyr | Leu | Lys | Trp | Ile | Pro | Asn | Arg | Asn | Phe | Glu |
| | | | 245 | | | | | 250 | | | | | 255 | | |
| Asn | Thr | Ile | Gln | Gln | Met | Tyr | Ile | Arg | Arg | Glu | Ala | Val | Met | Lys | Ala |
| | | | 260 | | | | | 265 | | | | | 270 | | |
| Leu | Ile | Gln | Glu | His | Arg | Lys | Arg | Ile | Ala | Ser | Gly | Glu | Asn | Leu | Asn |
| | | 275 | | | | | 280 | | | | | 285 | | | |
| Ser | Tyr | Ile | Asp | Tyr | Leu | Leu | Ser | Glu | Ala | Gln | Thr | Leu | Ser | Glu | Lys |
| | 290 | | | | | 295 | | | | | 300 | | | | |
| Gln | Leu | Xaa | Met | Ser | Leu | Trp | Glu | Pro | Ile | Ile | Glu | Ser | Ser | Asp | Thr |
| 305 | | | | | 310 | | | | | 315 | | | | | 320 |
| Thr | Met | Val | Thr | Thr | Glu | Trp | Ala | Met | Tyr | Glu | Leu | Ala | Lys | Asn | Pro |
| | | | | 325 | | | | | 330 | | | | | 335 | |
| Lys | Ile | Gln | Asp | Arg | Leu | Tyr | Arg | Glu | Ile | Gln | Gly | Val | Cys | Gly | Ser |
| | | | | 340 | | | | | 345 | | | | | 350 | |
| Asp | Lys | Ile | Xaa | Glu | Glu | Asn | Leu | Gly | Gln | Leu | Pro | Tyr | Leu | Ser | Ala |
| | | | 355 | | | | | 360 | | | | | 365 | | |
| Ile | Phe | Asn | Glu | Thr | Leu | Arg | Arg | His | Gly | Pro | Val | Pro | Ile | Ile | Pro |
| | | 370 | | | | | 375 | | | | | 380 | | | |

```
Leu Arg Tyr Val His Glu Asp Thr Glu Leu Gly Gly Tyr His Ile Pro
385                 390                 395                 400

Ala Gly Thr Gln Ile Ala Val Asn Ile Tyr Gly Cys Asn Met Glu Lys
            405                 410                 415

Ala Val Trp Glu Asn Pro Glu Glu Trp Asn Pro Glu Arg Phe Phe Glu
        420                 425                 430

Val Glu Gly Asp Gln Lys Thr Met Ala Phe Gly Gly Lys Arg Val
        435                 440                 445

Cys Ala Gly Ser Leu Gln Ala Met Leu Ile Ala Cys Ile Gly Ile Gly
450                 455                 460

Arg Met Val Gln Glu Phe Glu Trp Lys Leu Lys Asp Glu Ala Ala Gln
465                 470                 475                 480

Glu Asp Val Asn Thr Leu Gly Leu Thr Thr Gln Lys Leu Arg Pro Leu
            485                 490                 495

His Ala Ile Ile Tyr Pro Arg Lys Glu Asn Asp Ala Lys Val Trp Lys
                500                 505                 510

Cys

<210> SEQ ID NO 48

<400> SEQUENCE: 48

000

<210> SEQ ID NO 49
<211> LENGTH: 512
<212> TYPE: PRT
<213> ORGANISM: Artemisia annua

<400> SEQUENCE: 49

Met Asp Ala Leu Thr Asp Met Leu Gln Ile Pro Pro Ala Thr Pro Ile
1               5                   10                  15

Thr Val Ala Ile Thr Thr Val Thr Ile Ala Val Ala Ile Phe Leu Tyr
            20                  25                  30

Ile Lys Ser His Ala Ser Asn His Ser Arg Arg Ser Thr His Leu Pro
        35                  40                  45

Pro Val Pro Glu Val Pro Gly Val Pro Val Leu Gly Asn Leu Leu Gln
    50                  55                  60

Leu Lys Glu Lys Lys Pro Tyr Leu Thr Phe Thr Arg Trp Ala Gln Thr
65                  70                  75                  80

Tyr Gly Ala Ile Tyr Ser Ile Arg Thr Gly Ala Thr Ser Met Val Val
                85                  90                  95

Val Ser Ser Ser Glu Ile Ala Lys Glu Ala Met Val Thr Arg Phe Ser
            100                 105                 110

Ser Ile Ser Thr Arg Asn Leu Ser Lys Ala Leu Thr Ile Leu Thr Ala
        115                 120                 125

Asp Lys Thr Met Val Ala Met Ser Asp Tyr Asn Asp Tyr His Arg Thr
    130                 135                 140

Val Lys Arg His Ile Leu Thr Ala Met Leu Gly Pro Asn Ala Gln Arg
145                 150                 155                 160

Lys Gln Arg Val His Arg Asp Phe Met Ile Glu Asn Ile Ser Lys Gln
                165                 170                 175

Leu His Ala Phe Val Glu Asn Ser Pro Lys Glu Glu Val Asp Leu Arg
            180                 185                 190

Lys Ile Phe Gln Ser Glu Leu Phe Gly Leu Ala Met Lys Gln Ala Val
```

```
            195                 200                 205
Gly Lys Asp Val Glu Ser Leu Asn Val Glu Asp Leu Gly Val Thr Met
210                 215                 220

Lys Arg Asp Glu Ile Phe Gln Val Leu Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Lys Phe Glu Asn Thr Ile Gln Gln Met Tyr Ile Arg Arg
                260                 265                 270

Lys Ala Val Met Lys Ala Leu Ile Lys Glu His Lys Lys Arg Ile Ala
                275                 280                 285

Ser Gly Glu Asn Leu Asn Ser Tyr Ile Asp Tyr Leu Leu Ser Glu Ala
290                 295                 300

Gln Thr Phe Thr Asp Glu Gln Leu Ile Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Lys Met Gln Asp Arg Leu Tyr Arg Asp Ile
                340                 345                 350

Gln Ser Val Cys Gly Ser Asp Lys Ile Thr Glu Glu Asn Leu Ser Gln
                355                 360                 365

Leu Pro Tyr Leu Ser Ala Ile Phe His Glu Thr Leu Arg Arg His Ser
370                 375                 380

Pro Val Pro Ile Ile Pro Leu Arg His Val His Glu Asp Thr Val Leu
385                 390                 395                 400

Gly Gly Tyr His Val Pro Ala Gly Thr Glu Leu Ala Val Asn Ile Tyr
                405                 410                 415

Gly Cys Asn Met Glu Lys Asn Val Trp Glu Asn Pro Glu Glu Tyr Asn
                420                 425                 430

Pro Asp Arg Phe Met Lys Glu Asn Glu Thr Ile Asp Met Gln Arg Thr
                435                 440                 445

Met Ala Phe Gly Gly Gly Lys Arg Val Cys Ala Gly Ser Leu Gln Ala
450                 455                 460

Met Leu Ile Ser Cys Ile Gly Ile Gly Arg Met Val Gln Glu Phe Glu
465                 470                 475                 480

Trp Arg Phe Lys Asp Lys Ala Glu Glu Asp Ile Asn Thr Leu Gly Leu
                485                 490                 495

Thr Thr Gln Arg Leu Asn Pro Leu Arg Ala Ile Ile Lys Pro Arg Asn
                500                 505                 510

<210> SEQ ID NO 50
<211> LENGTH: 511
<212> TYPE: PRT
<213> ORGANISM: Helianthus annuus

<400> SEQUENCE: 50

Met Asp Ala Leu Thr Gly Met Leu Pro Ile Pro Pro Ala Thr Ala Leu
1               5                   10                  15

Ala Ile Gly Gly Thr Ala Ile Ala Leu Ala Val Ala Ile Ser Phe Trp
                20                  25                  30

Phe Leu Arg Ser Tyr Thr Ser Gly Glu Ser Asn Arg Leu Pro Arg Val
            35                  40                  45

Pro Glu Val Pro Gly Val Pro Val Leu Gly Asn Leu Leu Gln Leu Lys
50                  55                  60
```

```
Glu Lys Lys Pro Tyr Met Thr Phe Thr Arg Trp Ala Glu Thr Tyr Gly
 65                  70                  75                  80

Pro Ile Tyr Ser Ile Arg Thr Gly Ala Thr Ser Met Val Val Val Ser
                 85                  90                  95

Ser Asn Glu Ile Ala Lys Glu Ala Phe Val Thr Arg Phe Glu Ser Ile
            100                 105                 110

Ser Thr Arg Asn Leu Ser Lys Ala Leu Lys Ile Leu Thr Asp Asp Lys
            115                 120                 125

Thr Met Val Ala Met Ser Asp Tyr Asn Asp Tyr His Lys Thr Val Lys
            130                 135                 140

Arg His Ile Leu Thr Ala Met Leu Gly Pro Asn Ala Gln Lys Lys His
145                 150                 155                 160

Arg Ile Gln Arg Asp Ile Met Met Glu Asn Leu Ser Asn Arg Leu His
                165                 170                 175

Ala Phe Val Lys Thr Ser Thr Glu Gln Glu Glu Val Asp Leu Arg Glu
                180                 185                 190

Ile Phe Gln Ser Glu Leu Phe Gly Leu Ala Met Arg Gln Thr Met Gly
                195                 200                 205

Lys Asp Val Glu Ser Ile Tyr Val Glu Asp Leu Lys Ile Thr Met Lys
210                 215                 220

Arg Asp Glu Ile Phe Gln Val Leu Val Val Asp Pro Met Met Gly Ala
225                 230                 235                 240

Ile Asp Val Asp Trp Arg Asp Phe Phe Pro Tyr Leu Lys Trp Val Pro
                245                 250                 255

Asn Lys Lys Phe Glu Asn Thr Ile Gln Gln Met Tyr Ile Arg Arg Glu
                260                 265                 270

Ala Val Met Lys Ala Leu Ile Lys Gln His Lys Glu Arg Ile Ala Ser
                275                 280                 285

Gly Glu Lys Leu Asn Ser Tyr Ile Asp Tyr Leu Leu Ser Glu Ala Gln
                290                 295                 300

Ser Leu Thr Asp Arg Gln Leu Leu Met Ser Val Trp Glu Pro Ile Ile
305                 310                 315                 320

Glu Ser Ser Asp Thr Thr Met Val Thr Thr Glu Trp Ala Ile Tyr Glu
                325                 330                 335

Leu Ala Lys Asn Pro His Ile Gln Asp Arg Leu Tyr Arg Asp Ile Gln
                340                 345                 350

Ser Val Cys Gly Ser Asp Ile Ile Lys Glu Glu His Leu Ser Gln Leu
                355                 360                 365

Pro Phe Ile Thr Ala Ile Phe His Glu Thr Leu Arg Arg His Ser Pro
                370                 375                 380

Val Pro Ile Ile Pro Leu Arg Tyr Val His Glu Asp Thr Val Leu Gly
385                 390                 395                 400

Gly Tyr His Val Pro Ala Gly Thr Glu Leu Ala Ile Asn Ile Tyr Gly
                405                 410                 415

Cys Asn Met Glu Lys Ser Val Trp Glu Asn Pro Glu Gly Trp Asn Pro
                420                 425                 430

Glu Arg Phe Met Lys Glu Asn Glu Thr Ile Asp Phe Gln Lys Thr Met
                435                 440                 445

Ala Phe Gly Gly Gly Lys Arg Val Cys Ala Gly Ser Leu Gln Ala Met
                450                 455                 460

Leu Ile Ser Cys Val Gly Ile Gly Arg Met Val Gln Glu Phe Lys Trp
465                 470                 475                 480

Glu Leu Lys Asn Lys Ala Gln Glu Glu Val Asn Thr Ile Gly Leu Thr
```

485                 490                 495
Thr Gln Met Leu Arg Pro Leu Arg Ala Ile Ile Lys Pro Arg Asn
                500                 505                 510

<210> SEQ ID NO 51
<211> LENGTH: 505
<212> TYPE: PRT
<213> ORGANISM: Artificial Sequence
<220> FEATURE:
<223> OTHER INFORMATION: Synthetic Sequence

<400> SEQUENCE: 51

Met Ala Trp Glu Tyr Ala Leu Ile Gly Leu Val Val Gly Ile Ile
1               5                   10                  15

Gly Ala Val Ala Met Arg Trp Tyr Leu Lys Ser Tyr Thr Ser Ala Arg
                20                  25                  30

Arg Ser Gln Ser Asn His Leu Pro Arg Val Pro Glu Val Pro Gly Val
                35                  40                  45

Pro Leu Leu Gly Asn Leu Leu Gln Leu Glu Lys Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Leu Val Thr Arg Phe Gln Ser Ile Ser Thr Arg Asn Leu Ser
                100                 105                 110

Lys Ala Leu Lys Val Leu Thr Ala Asp Lys Gln Met Val Ala Met Ser
                115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
                180                 185                 190

Phe Gly Leu Ala Met Arg Gln Ala Leu Gly Lys Asp Val Glu Ser Leu
    195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
                260                 265                 270

Ile Lys Glu Gln Lys Lys Arg Ile Ala Ser Gly Glu Lys Leu Asn Ser
    275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu

```
                    340                 345                 350
Lys Ile Thr Glu Glu His Leu Ser Gln Leu Pro Tyr Ile Thr Ala Ile
                355                 360                 365
Phe His Glu Thr Leu Arg Lys His Ser Pro Val Pro Ile Leu Pro Leu
            370                 375                 380
Arg His Val His Glu Asp Thr Val Leu Gly Tyr His Val Pro Ala
385                 390                 395                 400
Gly Thr Glu Leu Ala Val Asn Ile Tyr Gly Cys Asn Met Asp Lys Asn
                405                 410                 415
Val Trp Glu Asn Pro Glu Glu Trp Asn Pro Glu Arg Phe Met Lys Glu
            420                 425                 430
Asn Glu Thr Ile Asp Phe Gln Lys Thr Met Ala Phe Gly Gly Gly Lys
                435                 440                 445
Arg Val Cys Ala Gly Ser Leu Gln Ala Leu Leu Ile Ala Ser Ile Gly
450                 455                 460
Ile Gly Arg Met Val Gln Glu Phe Glu Trp Lys Leu Lys Asp Met Thr
465                 470                 475                 480
Gln Glu Glu Val Asn Thr Ile Gly Leu Thr Asn Gln Met Leu Arg Pro
                485                 490                 495
Leu Arg Ala Ile Ile Lys Pro Arg Ile
            500                 505

<210> SEQ ID NO 52
<211> LENGTH: 492
<212> TYPE: PRT
<213> ORGANISM: Artificial Sequence
<220> FEATURE:
<223> OTHER INFORMATION: Synthetic Sequence

<400> SEQUENCE: 52

Met Ala Lys Pro Pro Leu Phe Phe Ile Val Ile Gly Leu Ile Val
1               5                   10                  15
Val Ala Ala Ser Phe Leu Tyr Lys Leu Leu Thr Arg Pro Thr Ser Ser
                20                  25                  30
Lys Asn Arg Leu Pro Glu Pro Trp Arg Leu Pro Ile Ile Gly His Met
            35                  40                  45
His His Leu Ile Gly Thr Met Pro His Arg Gly Val Met Asp Leu Ala
        50                  55                  60
Arg Lys Tyr Gly Ser Leu Met His Leu Gln Leu Gly Glu Val Ser Ala
65                  70                  75                  80
Ile Val Val Ser Ser Pro Lys Trp Ala Lys Glu Ile Leu Thr Thr Tyr
                85                  90                  95
Asp Ile Pro Phe Ala Asn Arg Pro Glu Thr Leu Thr Gly Glu Ile Ile
            100                 105                 110
Ala Tyr His Asn Thr Asp Ile Val Leu Ala Pro Tyr Gly Glu Tyr Trp
        115                 120                 125
Arg Gln Leu Arg Lys Leu Cys Thr Leu Glu Leu Leu Ser Val Lys Lys
    130                 135                 140
Val Lys Ser Phe Gln Ser Leu Arg Glu Glu Glu Cys Trp Asn Leu Val
145                 150                 155                 160
Gln Glu Ile Lys Ala Ser Gly Ser Gly Thr Pro Phe Asn Leu Ser Glu
                165                 170                 175
Gly Ile Phe Lys Val Ile Ala Thr Val Leu Ser Arg Ala Ala Phe Gly
            180                 185                 190
Lys Gly Ile Lys Asp Gln Lys Gln Phe Thr Glu Ile Val Lys Glu Ile
```

Leu Arg Glu Thr Gly Gly Phe Asp Val Ala Asp Ile Phe Pro Ser Lys
210                 215                 220

Lys Phe Leu His His Leu Ser Gly Lys Arg Gly Arg Leu Thr Ser Ile
225                 230                 235                 240

His Asn Lys Leu Asp Ser Leu Ile Asn Asn Leu Val Ala Glu His Thr
            245                 250                 255

Val Ser Lys Ser Ser Lys Val Asn Glu Thr Leu Leu Asp Val Leu Leu
                260                 265                 270

Arg Leu Lys Asn Ser Glu Glu Phe Pro Leu Thr Ala Asp Asn Val Lys
            275                 280                 285

Ala Ile Ile Leu Asp Met Phe Gly Ala Gly Thr Asp Thr Ser Ser Ala
290                 295                 300

Thr Val Glu Trp Ala Ile Ser Glu Leu Ile Arg Cys Pro Arg Ala Met
305                 310                 315                 320

Glu Lys Val Gln Ala Glu Leu Arg Gln Ala Leu Asn Gly Lys Glu Arg
                325                 330                 335

Ile Lys Glu Glu Glu Ile Gln Asp Leu Pro Tyr Leu Asn Leu Val Ile
            340                 345                 350

Arg Glu Thr Leu Arg Leu His Pro Pro Leu Pro Leu Val Met Pro Arg
                355                 360                 365

Glu Cys Arg Gln Ala Met Asn Leu Ala Gly Tyr Asp Val Ala Asn Lys
370                 375                 380

Thr Lys Leu Ile Val Asn Val Phe Ala Ile Asn Arg Asp Pro Glu Tyr
385                 390                 395                 400

Trp Lys Asp Ala Glu Ser Phe Asn Pro Glu Arg Phe Glu Asn Ser Asn
                405                 410                 415

Thr Thr Ile Met Gly Ala Asp Tyr Glu Tyr Leu Pro Phe Gly Ala Gly
            420                 425                 430

Arg Arg Met Cys Pro Gly Ser Ala Leu Gly Leu Ala Asn Val Gln Leu
                435                 440                 445

Pro Leu Ala Asn Ile Leu Tyr Tyr Phe Lys Trp Lys Leu Pro Asn Gly
450                 455                 460

Ala Ser His Asp Gln Leu Asp Met Thr Glu Ser Phe Gly Ala Thr Val
465                 470                 475                 480

Gln Arg Lys Thr Glu Leu Met Leu Val Pro Ser Phe
                485                 490

<210> SEQ ID NO 53
<211> LENGTH: 709
<212> TYPE: PRT
<213> ORGANISM: Camptotheca acuminata

<400> SEQUENCE: 53

Met Ala Gln Ser Ser Ser Val Lys Val Ser Thr Phe Asp Leu Met Ser
1               5                   10                  15

Ala Ile Leu Arg Gly Arg Ser Met Asp Gln Thr Asn Val Ser Phe Glu
                20                  25                  30

Ser Gly Glu Ser Pro Ala Leu Ala Met Leu Ile Glu Asn Arg Glu Leu
            35                  40                  45

Val Met Ile Leu Thr Thr Ser Val Ala Val Leu Ile Gly Cys Phe Val
        50                  55                  60

Val Leu Leu Trp Arg Arg Ser Ser Gly Lys Ser Gly Lys Val Thr Glu
65                  70                  75                  80

```
Pro Pro Lys Pro Leu Met Val Lys Thr Glu Pro Glu Pro Glu Val Asp
                85                  90                  95

Asp Gly Lys Lys Lys Val Ser Ile Phe Tyr Gly Thr Gln Thr Gly Thr
            100                 105                 110

Ala Glu Gly Phe Ala Lys Ala Leu Ala Glu Glu Ala Lys Val Arg Tyr
        115                 120                 125

Glu Lys Ala Ser Phe Lys Val Ile Asp Leu Asp Asp Tyr Ala Ala Asp
    130                 135                 140

Asp Glu Glu Tyr Glu Glu Lys Leu Lys Lys Glu Thr Leu Thr Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Met Glu Gly Lys Glu Arg Gly Asp Trp Leu Lys
            180                 185                 190

Asn Leu His Tyr Gly Val Phe Gly Leu Gly Asn Arg Gln Tyr Glu His
        195                 200                 205

Phe Asn Arg Ile Ala Lys Val Val Asp Asp Thr Ile Ala Glu Gln Gly
    210                 215                 220

Gly Lys Arg Leu Ile Pro Val Gly Leu Gly Asp Asp Asp Gln Cys Ile
225                 230                 235                 240

Glu Asp Asp Phe Ala Ala Trp Arg Glu Leu Leu Trp Pro Glu Leu Asp
                245                 250                 255

Gln Leu Leu Gln Asp Glu Asp Gly Thr Thr Val Ala Thr Pro Tyr Thr
            260                 265                 270

Ala Ala Val Leu Glu Tyr Arg Val Val Phe His Asp Ser Pro Asp Ala
        275                 280                 285

Ser Leu Leu Asp Lys Ser Phe Ser Lys Ser Asn Gly His Ala Val His
    290                 295                 300

Asp Ala Gln His Pro Cys Arg Ala Asn Val Ala Val Arg Arg Glu Leu
305                 310                 315                 320

His Thr Pro Ala Ser Asp Arg Ser Cys Thr His Leu Glu Phe Asp Ile
                325                 330                 335

Ser Gly Thr Gly Leu Val Tyr Glu Thr Gly Asp His Val Gly Val Tyr
            340                 345                 350

Cys Glu Asn Leu Ile Glu Val Val Glu Glu Ala Glu Met Leu Leu Gly
        355                 360                 365

Leu Ser Pro Asp Thr Phe Phe Ser Ile His Thr Asp Lys Glu Asp Gly
    370                 375                 380

Thr Pro Leu Ser Gly Ser Ser Leu Pro Pro Phe Pro Pro Cys Thr
385                 390                 395                 400

Leu Arg Arg Ala Leu Thr Gln Tyr Ala Asp Leu Leu Ser Ser Pro Lys
                405                 410                 415

Lys Ser Ser Leu Leu Ala Leu Ala His Cys Ser Asp Pro Ser Glu
            420                 425                 430

Ala Asp Arg Leu Arg His Leu Ala Ser Pro Ser Gly Lys Asp Glu Tyr
        435                 440                 445

Ala Gln Trp Val Val Ala Ser Gln Arg Ser Leu Leu Glu Val Met Ala
    450                 455                 460

Glu Phe Pro Ser Ala Lys Pro Pro Ile Gly Ala Phe Phe Ala Gly Val
465                 470                 475                 480

Ala Pro Arg Leu Gln Pro Arg Tyr Tyr Ser Ile Ser Ser Ser Pro Arg
                485                 490                 495

Met Ala Pro Ser Arg Ile His Val Thr Cys Ala Leu Val Phe Glu Lys
```

```
              500                 505                 510
Thr Pro Val Gly Arg Ile His Lys Gly Val Cys Ser Thr Trp Met Lys
            515                 520                 525

Asn Ala Val Pro Leu Asp Glu Ser Arg Asp Cys Ser Trp Ala Pro Ile
        530                 535                 540

Phe Val Arg Gln Ser Asn Phe Lys Leu Pro Ala Asp Thr Lys Val Pro
545                 550                 555                 560

Val Leu Met Ile Gly Pro Gly Thr Gly Leu Ala Pro Phe Arg Gly Phe
                565                 570                 575

Leu Gln Glu Arg Leu Ala Leu Lys Glu Ala Gly Ala Glu Leu Gly Pro
            580                 585                 590

Ala Ile Leu Phe Phe Gly Cys Arg Asn Arg Gln Met Asp Tyr Ile Tyr
        595                 600                 605

Glu Asp Glu Leu Asn Asn Phe Val Glu Thr Gly Ala Leu Ser Glu Leu
    610                 615                 620

Ile Val Ala Phe Ser Arg Glu Gly Pro Lys Lys Glu Tyr Val Gln His
625                 630                 635                 640

Lys Met Met Glu Lys Ala Ser Asp Ile Trp Asn Met Ile Ser Gln Glu
                645                 650                 655

Gly Tyr Ile Tyr Val Cys Gly Asp Ala Lys Gly Met Ala Arg Asp Val
            660                 665                 670

His Arg Thr Leu His Thr Ile Val Gln Glu Gly Ser Leu Asp Ser
        675                 680                 685

Ser Lys Thr Glu Ser Met Val Lys Asn Leu Gln Met Asn Gly Arg Tyr
    690                 695                 700

Leu Arg Asp Val Trp
705

<210> SEQ ID NO 54
<211> LENGTH: 516
<212> TYPE: PRT
<213> ORGANISM: Artificial Sequence
<220> FEATURE:
<223> OTHER INFORMATION: Synthetic Sequence

<400> SEQUENCE: 54

Met Ala Gln Asp Leu Arg Leu Ile Leu Ile Ile Val Gly Ala Ile Ala
1               5                   10                  15

Ile Ile Ala Leu Leu Val His Gly Phe Leu Leu Ile Lys Arg Ser Ser
            20                  25                  30

Arg Ser Ser Val His Lys Gln Gln Val Leu Leu Ala Ser Leu Pro Pro
        35                  40                  45

Ser Pro Pro Arg Leu Pro Leu Ile Gly Asn Ile His Gln Leu Val Gly
    50                  55                  60

Gly Asn Pro His Arg Ile Leu Gln Leu Ala Arg Thr His Gly Pro
65                  70                  75                  80

Leu Ile Cys Leu Arg Leu Gly Gln Val Asp Gln Val Val Ala Ser Ser
                85                  90                  95

Val Glu Ala Val Glu Glu Ile Ile Lys Arg His Asp Leu Lys Phe Ala
            100                 105                 110

Asp Arg Pro Arg Asp Leu Thr Phe Ser Arg Ile Phe Phe Tyr Asp Gly
        115                 120                 125

Asn Ala Val Val Met Thr Pro Tyr Gly Gly Glu Trp Lys Gln Met Arg
    130                 135                 140

Lys Ile Tyr Ala Met Glu Leu Leu Asn Ser Arg Arg Val Lys Ser Phe
```

```
            145                 150                 155                 160
        Ala Ala Ile Arg Glu Asp Val Ala Arg Lys Leu Thr Gly Glu Ile Ala
                        165                 170                 175

His Lys Ala Phe Ala Gln Thr Pro Val Ile Asn Leu Ser Glu Met Val
                        180                 185                 190

Met Ser Met Ile Asn Ala Ile Val Ile Arg Val Ala Phe Gly Asp Lys
                        195                 200                 205

Cys Lys Gln Gln Ala Tyr Phe Leu His Leu Val Lys Glu Ala Met Ser
                        210                 215                 220

Tyr Val Ser Ser Phe Ser Val Ala Asp Met Tyr Pro Ser Leu Lys Phe
        225                 230                 235                 240

Leu Asp Thr Leu Thr Gly Leu Lys Ser Lys Leu Glu Gly Val His Gly
                        245                 250                 255

Lys Leu Asp Lys Val Phe Asp Glu Ile Ile Ala Gln Arg Gln Ala Ala
                        260                 265                 270

Leu Ala Ala Glu Gln Ala Glu Glu Asp Leu Ile Ile Asp Val Leu Leu
                        275                 280                 285

Lys Leu Lys Asp Glu Gly Asn Gln Glu Phe Pro Ile Thr Tyr Thr Ser
                        290                 295                 300

Val Lys Ala Ile Val Met Glu Ile Phe Leu Ala Gly Thr Glu Thr Ser
        305                 310                 315                 320

Ser Ser Val Ile Asp Trp Val Met Ser Glu Leu Ile Lys Asn Pro Lys
                        325                 330                 335

Ala Met Glu Lys Val Gln Lys Glu Met Arg Glu Ala Met Gln Gly Lys
                        340                 345                 350

Thr Lys Leu Glu Glu Ser Asp Ile Pro Lys Phe Ser Tyr Leu Asn Leu
                        355                 360                 365

Val Ile Lys Glu Thr Leu Arg Leu His Pro Pro Gly Pro Leu Leu Phe
                        370                 375                 380

Pro Arg Glu Cys Arg Glu Thr Cys Glu Val Met Gly Tyr Arg Val Pro
        385                 390                 395                 400

Ala Gly Ala Arg Leu Leu Ile Asn Ala Phe Ala Leu Ser Arg Asp Glu
                        405                 410                 415

Lys Tyr Trp Gly Ser Asp Ala Glu Ser Phe Lys Pro Glu Arg Phe Glu
                        420                 425                 430

Gly Ile Ser Val Asp Phe Lys Gly Ser Asn Phe Glu Phe Met Pro Phe
                        435                 440                 445

Gly Ala Gly Arg Arg Ile Cys Pro Gly Met Thr Phe Gly Ile Ser Ser
        450                 455                 460

Val Glu Val Ala Leu Ala His Leu Leu Phe His Phe Asp Trp Gln Leu
        465                 470                 475                 480

Pro Gln Gly Met Lys Ile Glu Asp Leu Asp Met Met Glu Val Ser Gly
                        485                 490                 495

Met Ser Ala Thr Arg Arg Ser Pro Leu Leu Val Leu Ala Lys Leu Ile
                        500                 505                 510

Ile Pro Leu Pro
                515

<210> SEQ ID NO 55
<211> LENGTH: 510
<212> TYPE: PRT
<213> ORGANISM: Artificial Sequence
<220> FEATURE:
<223> OTHER INFORMATION: Synthetic Sequence
```

```
<400> SEQUENCE: 55

Met Ala Gln Asp Leu Arg Leu Ile Leu Ile Ile Val Gly Ala Ile Ala
1               5                   10                  15

Ile Ile Ala Leu Leu Val His Gly Phe Leu Lys Ser Ala Val Thr Lys
            20                  25                  30

Pro Lys Leu Asn Leu Pro Pro Gly Pro Trp Thr Leu Pro Leu Ile Gly
        35                  40                  45

Ser Ile His His Ile Val Ser Asn Pro Leu Pro Tyr Arg Ala Met Arg
    50                  55                  60

Glu Leu Ala His Lys His Gly Pro Leu Met Met Leu Trp Leu Gly Glu
65              70                  75                  80

Val Pro Thr Leu Val Val Ser Ser Pro Glu Ala Ala Gln Ala Ile Thr
                85                  90                  95

Lys Thr His Asp Val Ser Phe Ala Asp Arg His Ile Asn Ser Thr Val
            100                 105                 110

Asp Ile Leu Thr Phe Asn Gly Met Asp Met Val Phe Gly Ser Tyr Gly
        115                 120                 125

Glu Gln Trp Arg Gln Leu Arg Lys Leu Ser Val Leu Glu Leu Leu Ser
130                 135                 140

Ala Ala Arg Val Gln Ser Phe Gln Arg Ile Arg Glu Glu Glu Val Ala
145                 150                 155                 160

Arg Phe Met Arg Ser Leu Ala Ala Ser Ala Gly Ala Thr Val
                165                 170                 175

Asp Leu Ser Lys Met Ile Ser Ser Phe Ile Asn Asp Thr Phe Val Arg
            180                 185                 190

Glu Ser Ile Gly Ser Arg Cys Lys Tyr Gln Asp Glu Tyr Leu Ala Ala
        195                 200                 205

Leu Asp Thr Ala Ile Arg Val Ala Ala Glu Leu Ser Val Gly Asn Ile
    210                 215                 220

Phe Pro Ser Ser Arg Val Leu Gln Ser Leu Ser Thr Ala Arg Arg Lys
225                 230                 235                 240

Ala Ile Ala Ser Arg Asp Glu Met Ala Arg Ile Leu Gly Gln Ile Ile
                245                 250                 255

Arg Glu Thr Lys Glu Ser Met Asp Gln Gly Asp Lys Thr Ser Asn Glu
            260                 265                 270

Ser Met Ile Ser Val Leu Leu Arg Leu Gln Lys Asp Ala Gly Leu Pro
        275                 280                 285

Ile Glu Leu Thr Asp Asn Val Val Met Ala Leu Met Phe Asp Leu Phe
    290                 295                 300

Gly Ala Gly Ser Asp Thr Ser Ser Thr Thr Leu Thr Trp Cys Met Thr
305                 310                 315                 320

Glu Leu Val Arg Tyr Pro Ala Thr Met Ala Lys Ala Gln Ala Glu Val
                325                 330                 335

Arg Glu Ala Phe Lys Gly Lys Thr Thr Ile Thr Glu Asp Asp Leu Ser
            340                 345                 350

Thr Ala Asn Leu Arg Tyr Leu Lys Leu Val Val Lys Glu Ala Leu Arg
        355                 360                 365

Leu His Cys Pro Val Pro Leu Leu Pro Arg Lys Cys Arg Glu Ala
    370                 375                 380

Cys Gln Val Met Gly Tyr Asp Ile Pro Lys Gly Thr Cys Val Phe Val
385                 390                 395                 400

Asn Val Trp Ala Ile Cys Arg Asp Pro Arg Tyr Trp Glu Asp Ala Glu
                405                 410                 415
```

-continued

```
Glu Phe Lys Pro Glu Arg Phe Glu Asn Ser Asn Leu Asp Tyr Lys Gly
            420                 425                 430

Thr Tyr Tyr Glu Tyr Leu Pro Phe Gly Ser Gly Arg Arg Met Cys Pro
        435                 440                 445

Gly Ala Asn Leu Gly Val Ala Asn Leu Glu Leu Ala Leu Ala Ser Leu
450                 455                 460

Leu Tyr His Phe Asp Trp Lys Leu Pro Ser Gly Gln Glu Pro Lys Asp
465                 470                 475                 480

Val Asp Val Trp Glu Ala Ala Gly Leu Val Ala Lys Lys Asn Ile Gly
                485                 490                 495

Leu Val Leu His Pro Val Ser His Ile Ala Pro Val Asn Ala
                500                 505                 510
```

<210> SEQ ID NO 56
<211> LENGTH: 511
<212> TYPE: PRT
<213> ORGANISM: Artificial Sequence
<220> FEATURE:
<223> OTHER INFORMATION: Synthetic Sequence

<400> SEQUENCE: 56

```
Met Ala Gln Asp Leu Arg Leu Ile Leu Ile Ile Val Gly Ala Ile Ala
1               5                   10                  15

Ile Ile Ala Leu Leu Val His Gly Phe Phe Leu Leu Arg Lys Trp Lys
                20                  25                  30

Asn Ser Asn Ser Gln Ser Lys Lys Leu Pro Pro Gly Pro Trp Lys Leu
            35                  40                  45

Pro Leu Leu Gly Ser Met Leu His Met Val Gly Gly Leu Pro His His
    50                  55                  60

Val Leu Arg Asp Leu Ala Lys Lys Tyr Gly Pro Leu Met His Leu Gln
65                  70                  75                  80

Leu Gly Glu Val Ser Ala Val Val Val Thr Ser Pro Asp Met Ala Lys
                85                  90                  95

Glu Val Leu Lys Thr His Asp Ile Ala Phe Ala Ser Arg Pro Lys Leu
            100                 105                 110

Leu Ala Pro Glu Ile Val Cys Tyr Asn Arg Ser Asp Ile Ala Phe Cys
        115                 120                 125

Pro Tyr Gly Asp Tyr Trp Arg Gln Met Arg Lys Ile Cys Val Leu Glu
    130                 135                 140

Val Leu Ser Ala Lys Asn Val Arg Ser Phe Ser Ser Ile Arg Arg Asp
145                 150                 155                 160

Glu Val Leu Arg Leu Val Asn Phe Val Arg Ser Ser Thr Ser Glu Pro
                165                 170                 175

Val Asn Phe Thr Glu Arg Leu Phe Leu Phe Thr Ser Ser Met Thr Cys
            180                 185                 190

Arg Ser Ala Phe Gly Lys Val Phe Lys Glu Gln Glu Thr Phe Ile Gln
        195                 200                 205

Leu Ile Lys Glu Val Ile Gly Leu Ala Gly Gly Phe Asp Val Ala Asp
    210                 215                 220

Ile Phe Pro Ser Leu Lys Phe Leu His Val Leu Thr Gly Met Glu Gly
225                 230                 235                 240

Lys Ile Met Lys Ala His His Lys Val Asp Ala Ile Val Glu Asp Val
                245                 250                 255

Ile Asn Glu His Lys Lys Asn Leu Ala Met Gly Lys Thr Asn Gly Ala
            260                 265                 270
```

-continued

```
Leu Gly Gly Glu Asp Leu Ile Asp Val Leu Leu Arg Leu Met Asn Asp
            275                 280                 285

Gly Gly Leu Gln Phe Pro Ile Thr Asn Asp Asn Ile Lys Ala Ile Ile
    290                 295                 300

Phe Asp Met Phe Ala Ala Gly Thr Glu Thr Ser Ser Ser Thr Leu Val
305             310                 315                 320

Trp Ala Met Val Gln Met Met Arg Asn Pro Thr Ile Leu Ala Lys Ala
                325                 330                 335

Gln Ala Glu Val Arg Glu Ala Phe Lys Gly Lys Glu Thr Phe Asp Glu
                340                 345                 350

Asn Asp Val Glu Glu Leu Lys Tyr Leu Lys Leu Val Ile Lys Glu Thr
            355                 360                 365

Leu Arg Leu His Pro Pro Val Pro Leu Leu Val Pro Arg Glu Cys Arg
    370                 375                 380

Glu Glu Thr Glu Ile Asn Gly Tyr Thr Ile Pro Val Lys Thr Lys Val
385             390                 395                 400

Met Val Asn Val Trp Ala Leu Gly Arg Asp Pro Lys Tyr Trp Asp Asp
                405                 410                 415

Ala Asp Asn Phe Lys Pro Glu Arg Phe Glu Gln Cys Ser Val Asp Phe
                420                 425                 430

Ile Gly Asn Asn Phe Glu Tyr Leu Pro Phe Gly Gly Gly Arg Arg Ile
                435                 440                 445

Cys Pro Gly Ile Ser Phe Gly Leu Ala Asn Val Tyr Leu Pro Leu Ala
            450                 455                 460

Gln Leu Leu Tyr His Phe Asp Trp Lys Leu Pro Thr Gly Met Glu Pro
465                 470                 475                 480

Lys Asp Leu Asp Leu Thr Glu Leu Val Gly Ile Thr Ile Ala Arg Lys
                485                 490                 495

Ser Asp Leu Met Leu Val Ala Thr Pro Tyr Gln Pro Ser Arg Glu
                500                 505                 510
```